United States Patent
Akeson et al.

(10) Patent No.: US 10,344,327 B2
(45) Date of Patent: Jul. 9, 2019

(54) COMPOSITIONS, DEVICES, SYSTEMS, AND METHODS FOR USING A NANOPORE

(71) Applicant: The Regents of the University of California, Oakland, CA (US)

(72) Inventors: Mark A. Akeson, Santa Cruz, CA (US); David W. Deamer, Santa Cruz, CA (US); William B. Dunbar, Santa Cruz, CA (US); Roger Jinteh Arrigo Chen, Saratoga, CA (US); Noah A. Wilson, Felton, CA (US)

(73) Assignee: The Regents of the University of California, Oakland, CA (US)

( * ) Notice: Subject to any disclaimer, the term of this patent is extended or adjusted under 35 U.S.C. 154(b) by 488 days.

(21) Appl. No.: 15/087,734

(22) Filed: Mar. 31, 2016

(65) Prior Publication Data

US 2016/0209350 A1 Jul. 21, 2016

Related U.S. Application Data

(63) Continuation of application No. 14/919,315, filed on Oct. 21, 2015, now Pat. No. 10,196,688, which is a
(Continued)

(51) Int. Cl.
*C12Q 1/54* (2006.01)
*C25B 3/10* (2006.01)
(Continued)

(52) U.S. Cl.
CPC ............ *C12Q 1/6874* (2013.01); *C12Q 1/54* (2013.01); *C12Q 1/6869* (2013.01); *C25B 3/10* (2013.01);
(Continued)

(58) Field of Classification Search
CPC ...... C12Q 1/6874; C12Q 1/54; C12Q 1/6869; G01N 27/4166; G01N 27/3278; G01N 33/48721; C25B 3/10
(Continued)

(56) References Cited

U.S. PATENT DOCUMENTS 5,474,796 A 12/1995 Brennan
5,593,840 A 1/1997 Bhatnagar et al.
(Continued)

FOREIGN PATENT DOCUMENTS

EP 1486775 A1 12/2004
JP 2005/519622 A 7/2005
(Continued)

OTHER PUBLICATIONS

Andraos, N., et al.., "The Highly Processive DNA Polymerase of Bacteriophage T5," J. Bio. Chem. (2004) 279(48):50609-50618.
(Continued)

*Primary Examiner* — Farhana A Hoque
(74) *Attorney, Agent, or Firm* — Brian E. Davy; Bozicevic, Field & Francis LLP

(57) ABSTRACT

Devices and methods that can detect and control an individual polymer in a mixture is acted upon by another compound, for example, an enzyme, in a nanopore are provided. The devices and methods also determine (~>50 Hz) the nucleotide base sequence of a polynucleotide under feedback control or using signals generated by the interactions between the polynucleotide and the nanopore. The invention is of particular use in the fields of molecular biology, structural biology, cell biology, molecular switches, molecular circuits, and molecular computational devices, and the manufacture thereof.

10 Claims, 26 Drawing Sheets

Related U.S. Application Data continuation of application No. 14/300,453, filed on Jun. 10, 2014, which is a continuation of application No. 14/056,636, filed on Oct. 17, 2013, now Pat. No. 10,081,835, which is a continuation of application No. 13/615,183, filed on Sep. 13, 2012, now Pat. No. 10,059,988, which is a continuation of application No. 12/080,684, filed on Apr. 4, 2008, now abandoned.

(60) Provisional application No. 61/062,391, filed on Jan. 25, 2008, provisional application No. 60/967,539, filed on Sep. 4, 2007, provisional application No. 60/962,530, filed on Jul. 30, 2007, provisional application No. 60/931,115, filed on May 21, 2007, provisional application No. 60/921,787, filed on Apr. 4, 2007.

(51) Int. Cl.
  *C12Q 1/6869* (2018.01)
  *C12Q 1/6874* (2018.01)
  *G01N 27/327* (2006.01)
  *G01N 27/416* (2006.01)
  *G01N 33/487* (2006.01)

(52) U.S. Cl.
  CPC ..... *G01N 27/3278* (2013.01); *G01N 27/4166* (2013.01); *G01N 33/48721* (2013.01)

(58) Field of Classification Search
  USPC ......................................... 324/717; 435/6.12
  See application file for complete search history.

(56) References Cited

U.S. PATENT DOCUMENTS

| | | | |
|---|---|---|---|
| 5,605,662 A | 2/1997 | Heller et al. | |
| 5,795,782 A | 8/1998 | Church et al. | |
| 5,932,451 A | 8/1999 | Wang et al. | |
| 6,015,714 A | 1/2000 | Baldarelli et al. | |
| 6,114,121 A | 9/2000 | Fujiwara et al. | |
| 6,197,526 B1 | 3/2001 | Yu et al. | |
| 6,248,567 B1 | 6/2001 | Liles et al. | |
| 6,267,872 B1 | 7/2001 | Akeson et al. | |
| 6,362,002 B1 | 3/2002 | Denison et al. | |
| 6,428,959 B1 | 8/2002 | Deamer | |
| 6,464,842 B1 | 10/2002 | Golovchenko et al. | |
| 6,579,682 B1 | 6/2003 | Innerarity et al. | |
| 6,617,113 B2 | 9/2003 | Deamer | |
| 6,627,067 B1 | 9/2003 | Branton et al. | |
| 6,632,610 B2 | 10/2003 | Thill | |
| 6,673,615 B2 | 1/2004 | Denison et al. | |
| 6,746,594 B2 | 6/2004 | Akeson et al. | |
| 7,189,503 B2 | 3/2007 | Akeson et al. | |
| 7,238,485 B2 | 7/2007 | Akeson et al. | |
| 7,426,117 B2 | 9/2008 | Van Schuylenbergh et al. | |
| 7,501,279 B2 | 3/2009 | Folch et al. | |
| 8,324,914 B2 | 12/2012 | Chen et al. | |
| 8,500,982 B2 | 8/2013 | Akeson et al. | |
| 2001/0010913 A1 | 8/2001 | Hillman et al. | |
| 2003/0104428 A1 | 6/2003 | Branton et al. | |
| 2004/0023207 A1 | 2/2004 | Polansky | |
| 2004/0121525 A1 | 6/2004 | Chopra et al. | |
| 2004/0149580 A1 | 8/2004 | Flory | |
| 2005/0009004 A1 | 1/2005 | Xu et al. | |
| 2005/0053961 A1 | 3/2005 | Akeson et al. | |
| 2005/0127035 A1 | 6/2005 | Ling | |
| 2005/0136408 A1 | 6/2005 | Tom-Moy et al. | |
| 2005/0208574 A1 | 9/2005 | Bayley et al. | |
| 2006/0019247 A1 | 1/2006 | Su et al. | |
| 2006/0063171 A1 | 3/2006 | Akeson et al. | |
| 2006/0073489 A1 | 7/2006 | Li et al. | |
| 2006/0155483 A1 | 7/2006 | Antoniotti et al. | |
| 2007/0048745 A1 | 3/2007 | Joyce et al. | |
| 2007/0099191 A1* | 5/2007 | Nair .................... C12Q 1/68 435/6.12 |
| 2010/0035260 A1 | 2/2010 | Olasagasti et al. | |
| 2010/0121582 A1 | 5/2010 | Pan et al. | |
| 2010/0188109 A1 | 7/2010 | Edel et al. | |
| 2010/0331194 A1 | 12/2010 | Turner et al. | |
| 2011/0005918 A1 | 1/2011 | Akeson et al. | |
| 2011/0174625 A1 | 7/2011 | Akeson et al. | |
| 2011/0311965 A1 | 12/2011 | Maglia et al. | |
| 2013/0118902 A1 | 5/2013 | Akeson et al. | |
| 2014/0034517 A1 | 2/2014 | Akeson et al. | |
| 2014/0051068 A1 | 2/2014 | Cherf et al. | |
| 2014/0346059 A1 | 11/2014 | Akeson et al. | |
| 2016/0040230 A1 | 2/2016 | Akeson et al. | |

FOREIGN PATENT DOCUMENTS

| | | |
|---|---|---|
| WO | 94/25862 A1 | 11/1994 |
| WO | 95/25116 | 9/1995 |
| WO | 95/35505 | 12/1995 |
| WO | 0028312 A1 | 5/2000 |
| WO | 00/79257 A1 | 12/2000 |
| WO | 02/42496 A2 | 5/2002 |
| WO | 2003/078649 A2 | 9/2003 |
| WO | 2006/020775 A2 | 2/2006 |
| WO | 2006/028508 A2 | 3/2006 |
| WO | 2006100484 A2 | 9/2006 |
| WO | 2008/005674 A2 | 1/2008 |
| WO | 2008102121 A1 | 8/2008 |
| WO | 2008/124107 A1 | 10/2008 |
| WO | 2009035647 A1 | 3/2009 |
| WO | 2009/077734 A2 | 6/2009 |
| WO | 2010004265 A1 | 1/2010 |
| WO | 2010004273 A1 | 1/2010 |
| WO | 2010086603 A1 | 8/2010 |
| WO | 2010/122293 A1 | 10/2010 |
| WO | 2011067559 A1 | 6/2011 |
| WO | 2012173905 A1 | 12/2012 |

OTHER PUBLICATIONS

Brüggermann, A. et al., "Microchip Technology for Automated and Parallel Patch-Clam Recording," small (2006) 2(7):840.846.

Cockroft, et al., "A Single-Molecule Nanopore Device Detects DNA Polymerase Activity with Single-Nucleotide Resolution," J.Am.Chem.Soc. (2008) 130:818-820. (published on webJan. 1, 2008).

Cockroft, et al., "A Single-Molecule Nanopore Device Detects DNA Polymerase Activity with Single-Nucleotide Resolution," J.Am.Chem.Soc. (2008) 130:818-820. (article supporting material) 13 pp.

Davies, Kevin, "Nanopore sequencing takes more small steps", Bio-IT World, Dec. 3, 2010.

Deamer, et al., "Nanopores and nucleic acids: prospects for ultrarapid sequencing," TIBTECH, Apr. 2000, vol. 18, pp. 147-151.

Deamer, "Nanopore analysis of nucleic acids bound to exonucleases and polymerases", Annual Review of Biophysics, vol. 39, pp. 79-90, Jun. 9, 2010.

Fologea, et al., "Detecting single stranded DNA with a solid state nanopore", Nano Leters, 2005, vol. 5, No. 10, 1905-1909.

Gyarfas, et al., "Measuring single-molecule DNA hybridization by active control of DNA in a nanopore", Biophysical Journal, vol. 100, Mar. 2011, 1509-1516.

Jing, et al., "Robust properties of membrane-embedded connector channel of bacterial virus phi29 DNA packaging motor", Molecular Biosystems, vol. 6, No. 10, p. 1844, Jan. 1, 2010.

Lieberman, et al., "Processive replication of single NA molecules in a nanopore catalyzed by phi29 DNA polymerase", Journal of the American Chemical Society, vol. 132(50), pp. 17961-17972, Dec. 1, 2010.

Meller, et al., "Voltage-Driven DNA Translocations through a Nanopore," Physical Review Letters (2001) 86(15):3435-3438.

Nelson, et al., "TempliPhi, Φ29 DNA Polymerase Based Rolling Circle Amplification of Templates for DNA Sequencing," Biotechniques (2002) 32:S44-47.

(56) References Cited

OTHER PUBLICATIONS

Ogawa, et al., "Distinct Function of Conserved Amino Acids in the Fingers of *Saccharomyces cerevisiae* DNA Polymrase α*," J. Biol. Chem. (2003) 278(21):19071-19078.
Perkel, Jeffrey, "Making contact with sequencing's fourth generation", Biotechniques, vol. 50 No. 1, pp. 93-95, Feb. 9, 2011.
Rothwell, P., et al., "Structure and Mechanism of DNA Polymerases," Advances in Protein Chemistry. (2005) 71:401-440.
Subramanian, K., et al., "The enzymatic basis of processivity in λ exonuclease," Nucleic Acids Research. (2003) 31(6):1585-1596.
Suzuki, H., et al., "Ninety-six-well planar lipid bilayer chip for ion channel recording Fabricated by hybrid stereolithography," (2009) Biomed Microdevices 11:17-22.
Wendell, et al., "Translocation of double-stranded DNA through membrane-adapted phi29 motor protein nanopores,", Nature Nanotechnology (2009) 4(11):765-772.
Wendell, et al., Supplement Material (2009), 7 pp.
Wendell, et al., Supplemental Fig. (2009) 12 pp.
United States District Court, Northern District of California, Case No. 3:16-CV-07396-EMC, *The Regents of the University of California*, Plaintiff, v. *Roger Jinteh Arrigo Chen, et al.*, Defendants, First Amended Complaint, Mar. 20, 2017, 59 pp.
United States District Court, Northern District of California, Case No. 3:16-CV-07396-EMC, *The Regents of the University of California*, Plaintiff, v. *Roger Jinteh Arrigo Chen, et al.*, Defendants, Plaintiff's Response to Defendant Genia Technologies, Inc.'s First Set of Interrogatories (Nos. 1-8), Apr. 14, 2017, 28 pp.
United States District Court, Northern District of California, Case No. 3:16-CV-07396-EMC, *The Regents of the University of California*, Plaintiff, v. *Roger Jinteh Arrigo Chen, et al.*, Defendants, Defendant Roger Chen's Responses to Plaintiff's First Set of Interrogatories to Defendant Roger Chen, May 15, 2017, 15 pp.
United States District Court, Northern District of California, Case No. 3:16-CV-07396-EMC, *The Regents of the University of California*, Plaintiff, v. *Roger Jinteh Arrigo Chen, et al.*, Defendants, Defendant Roger Chen's Responses to Plaintiff's First Set of Requests for Admission, May 15, 2017, 19 pp.
Amendment and Response to Final Office Action Accompanying Request for Continued Examination (RCE) filed Dec. 22, 2016, U.S. Appl. No. 14/300,453, filed Jun. 10, 2014.
Declaration Under 37 CFR 1.132 of Andre Marziali dated Dec. 20, 2016 filed Dec. 22, 2016, U.S. Appl. No. 14/300,453, filed Jun. 10, 2014.
Curriculum Vitae of Andre Marziali dated May 17, 2016 filed Dec. 22, 2016, U.S. Appl. No. 14/300,453, filed Jun. 10, 2014.
Applicant-Initiated Interview Summary dated Aug. 31, 2016, U.S. Appl. No. 14/919,315, filed Oct. 21, 2015.
Amendment and Response to Non-Final Office Action filed Sep. 30, 2016, U.S. Appl. No. 14/919,315, filed Oct. 21, 2015.
Final Office Action dated Jan. 18, 2017; U.S. Appl. No. 14/919,315, filed Oct. 21, 2015.
Amendment and Response to Final Office Action Accompanying Request for Continued Examination (RCE) filed May 18, 2017, U.S. Appl. No. 14/919,315, filed Oct. 21, 2015.
Declaration Under 37 CFR 1.132 of Andre Marziali dated May 17, 2017 filed May 18, 2017, U.S. Appl. No. 14/919,315, filed Oct. 21, 2015.
Office Action (Restriction Requirement) dated Sep. 6, 2016, U.S. Appl. No. 15/162,225, filed May 23, 2016.
Preliminary Amendment and Response to Restriction Requirement filed Nov. 1, 2016, U.S. Appl. No. 15/162,225, filed May 23, 2016.
Non-Final Office Action dated Jan. 30, 2017, U.S. Appl. No. 15/162,225, filed May 23, 2016.
Amendment and Response to Non-Final Office Action filed Apr. 28, 2017, U.S. Appl. No. 15/162,225, filed May 23, 2016.
Notice of Allowance and Fee(s) Due dated Jun. 16, 207, U.S. Appl. No. 15/162,225, filed May 23, 2016.
Abbondanzieri et al., "Direct observation of base-pair stepping by RNA polymerase," Nature (Nov. 2005), pp. 460-465, vol. 438.
Andersson, et al., "Detection of Single Ion Channel Activity on a Chip Using Tethered Bilayer Membranes," American Chemical Society (Feb. 28, 2007), 4 pp.
Astier et al., "Stochastic detection of motor protein-RNA complexes by single-channel current recording", ChemPhysChem (2007), pp. 2189-2194, vol. 8.
Baaken et al., "Planar microelectrode-cavity array for high-resolution and parallel electrical recording of membrane ionic currents," Lab Chip, (2008) vol. 8, pp. 938-944.
Bates et al., "Dynamics of DNA molecules in a membrane channel probed by active control techniques," Biopyhsical Journal (Apr. 2003), pp. 2366-2372, vol. 84.
Bayley and Cremer, "Stochastic sensors inspired by biology," Nature, vol. 413, (Sep. 13, 2001), pp. 226-230.
Benner et al., "Sequence-specific detection of individual DNA polymerase complexes in real time using a nanopore," Nature Nanotechnology (Nov. 2007), pp. 718-724, vol. 2.
Bustamante et al., "Ten years of tension: single-molecule DNA mechanics," Nature (Jan. 2003), pp. 423-427, vol. 421.
Castellana and Cremer, "Solid supported lipid bilayers: From biophysical studies to sensor design," ScienceDirect, Surface Science Reports 61 (2006), pp. 429-444.
EESR, Application No. 08727306.6, Dated Jan. 20, 2014.
Gordon et al., "Consed: a graphical tool for sequence finishing," Genome Research (1998), pp. 195-202, vol. 8.
Greenleaf et al., "Single-molecule, motion-based DNA sequencing using RNA polymerase," Science (Aug. 2006), p. 801, vol. 313.
Heller, et al., "Discovery and analysis of inflamatory disease-related genes using cDNA miroarrays," Proc. Natl. Acad. Aci. USA (Mar. 1997), pp. 2150-2155, vol. 94.
Hornblower et al., "Single-molecule analysis of DNA-protein complexes using nanopores," Nature Methods (Apr. 2007), pp. 315-317, vol. 4.
Kashima et al., "Unique structure of murine interleukin-2 as deduced from cloned cDNAs," Nature (Jan. 31, 1985) pp. 402-404, vol. 313.
Kasianowicz, et al., "Characterization of individual polynucleotide molecules using a membrane channel," Proc. Natl. Acad. Sci. USA (Nov. 1996) pp. 13770-13773, vol. 93.
Metzker, "Emerging technologies in DNA sequencing," Genome Research (2005), pp. 1767-1776, vol. 15.
Nielsen et al., "An introduction to peptide nucleic acid", Current Issues Molec. Biol. (1999) 1(2); 89-104.
Patent Examination Report No. 1 Australia Patent Application No. 2008236694, dated Oct. 18, 2012, 3 pages.
Rhee et al., "Nanopore sequencing technology: research trends and applications," Trends in Biotechnology (Oct. 2006), pp. 580-586, vol. 24.
Sanger, et al., "A rapid method for determining sequences in DNA primed synthesis with DNA polymerase," Journal of Molecular Biology (1975), pp. 441-448, vol. 94.
Schena et al., "Parallel human genome analysis: Microarray-based expression monitoring of 1000 genes," Proc. Natl. Acad. Sci. USA (Oct. 1996), pp. 10614-10619, vol. 93.
Tanaka and Sackmann, "Polymer-supported membranes as models of the cell surface," Nature, vol. 437 (Sep. 29, 2005), pp. 656-663.
Vercoutere et al., "Discrimination among individual Watson-Crick base pairs at the termini of single DNA hairpin molecules," Nucleic Acids Research (2003), pp. 1311-1318, vol. 31.
Vercoutere et al., "Rapid discrimination among individual DNA hairpin molecules at single-nucleotide resolution using an ion channel," Nature Biotechnology (Mar. 2001) pp. 248-252, vol. 19.
Wilson et al., "Feedback control of a DNA molecule tethered in a nanopore to repeatedly probe DNA-binding enzymes," Conf. Proc. IEEE Eng. Med. Biol. Soc. (2008a), 30th Annual International IEEE EMBS Conference, pp. 5745-5748.
Wilson et al., "Rapid finite state machine control of individual DNA molecules in a nanopore," International Conference on Biomedical Electronics and Devices (2008b), pp. 94-98, Madeira, Portugal.
Winters-Hilt et al., "Highly accurate classification of Watson-Crick basepairs on termini of single DNA molecules", Biophysical Journal (Feb. 2003), pp. 967-976, vol. 84.
Office Action (English Translation), JP Patent Application No. 2014-225711, dated Oct. 27, 2015, 3 pp.

(56) References Cited

OTHER PUBLICATIONS

Non-Final Office Action dated Feb. 29, 2016, U.S. Appl. No. 14/300,453, filed Jun. 10, 2014.
Applicant-Initiated Interview Summary dated Mar. 15, 2016, U.S. Appl. No. 14/300,453, filed Jun. 10, 2014.
Amendment and Response to Non-Final Office Action dated Feb. 29, 2016 filed Jun. 9, 2016, U.S. Appl. No. 14/300,453, filed Jun. 10, 2014.
Declaration Under 37 CFR 1.132 of Andre Marziali dated Jun. 7, 2016 filed Jun. 9, 2016, U.S. Appl. No. 14/300,453, filed Jun. 10, 2014.
Curriculum Vitae of Andre Marziali dated May 17, 2016 filed Jun. 9, 2016, U.S. Appl. No. 14/300,453, filed Jun. 10, 2014.
Final Office Action dated Jun. 30, 2016, U.S. Appl. No. 14/300,453, filed Jun. 10, 2014.
Non-Final Office Action dated Feb. 18, 2016, U.S. Appl. No. 14/919,315, filed Oct. 21, 2015.
Appplicant-Initiated Interview Summary dated Mar. 14, 2016, U.S. Appl. No. 14/919,315, filed Oct. 21, 2015.
Third-Party Submission filed May 11, 2016, U.S. Appl. No. 14/919,315, filed Oct. 21, 2015.
Amendment and Response to Non-Final Office Action dated Feb. 18, 2016 filed May 17, 2016, U.S. Appl. No. 14/919,315, filed Oct. 21, 2015.
Declaration Under 37 CFR 1.132 of Andre Marziali dated May 16, 2016 filed May 17, 2016, U.S. Appl. No. 14/919,315, filed Oct. 21, 2015.
Curriculum Vitae of Andre Marziali dated May 17, 2016 filed May 17, 2016, U.S. Appl. No. 14/919,315, filed Oct. 21, 2015.
Response to Third Party Submission filed Jun. 30, 2016, U.S. Appl. No. 14/919,315, filed Oct. 21, 2015.
Non-Final Office Action dated Jun. 30, 2016, U.S. Appl. No. 14/919,315, filed Oct. 21, 2015.
Neugebauer, Sebastian, et al. "Characterization of Nanopore Electrode Structures as Basis for Amplified Electrochemical Assays." Electroanalysis, vol. 18 (2006): 1929-1936.†
Tropini, Carolina and Marziali, Andre, "Multi-Nanopore Force Spectroscopy for DNA Analysis." Biophysical Journal, vol. 92, Mar. 2007: 1632-1637.†
Bayley, Hagan and Cremer, Paul S., "Stochastic sensors inspired by biology." Nature, vol. 413 (2001): 226-230.†

\* cited by examiner
† cited by third party

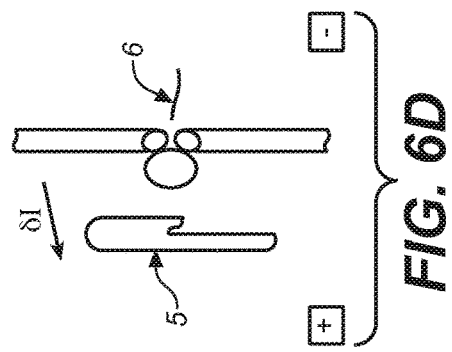
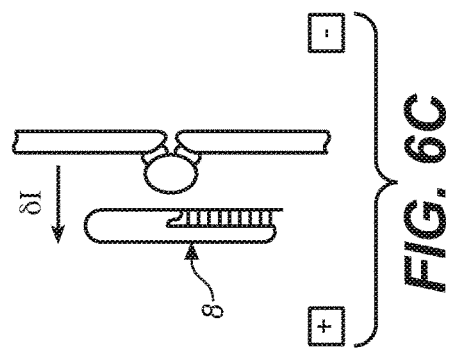
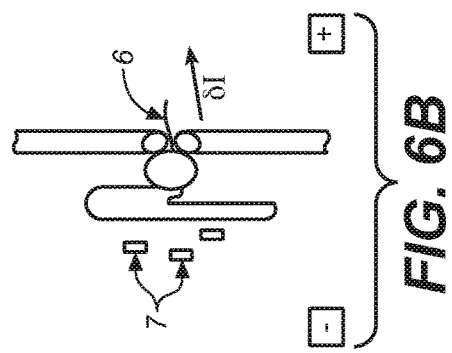
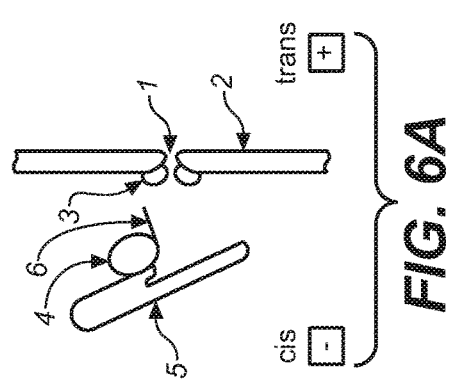
FIG. 6A  FIG. 6B  FIG. 6C  FIG. 6D
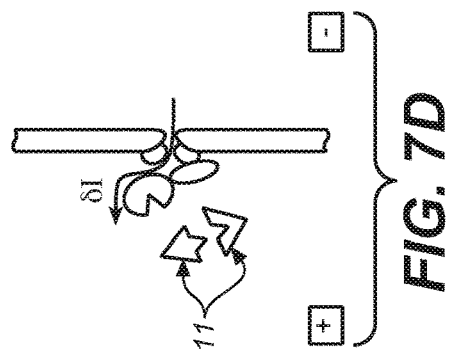
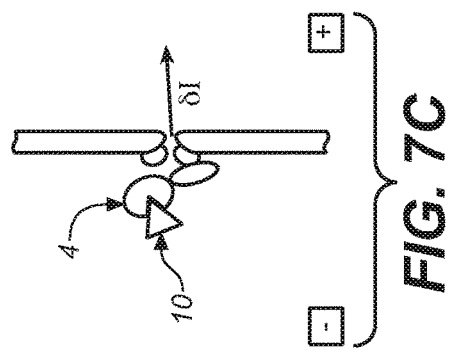
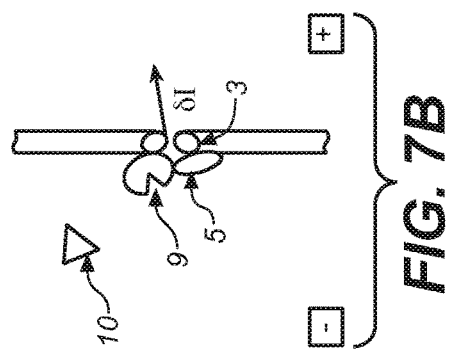
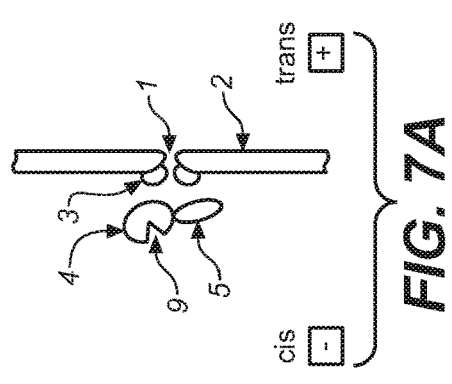
FIG. 7A  FIG. 7B  FIG. 7C  FIG. 7D

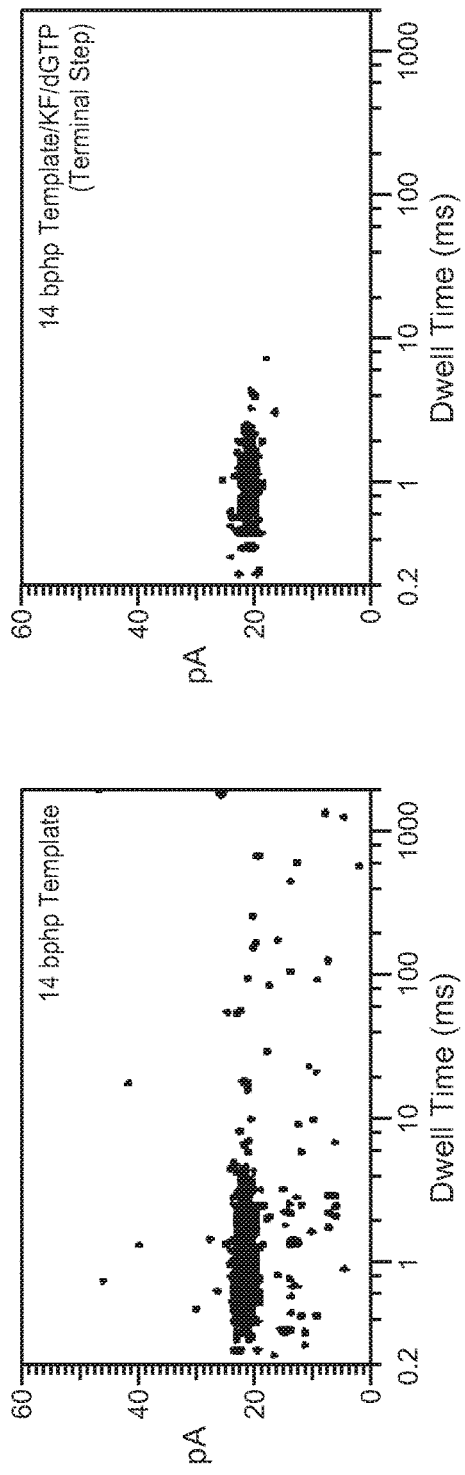
FIG. 19B
FIG. 19C
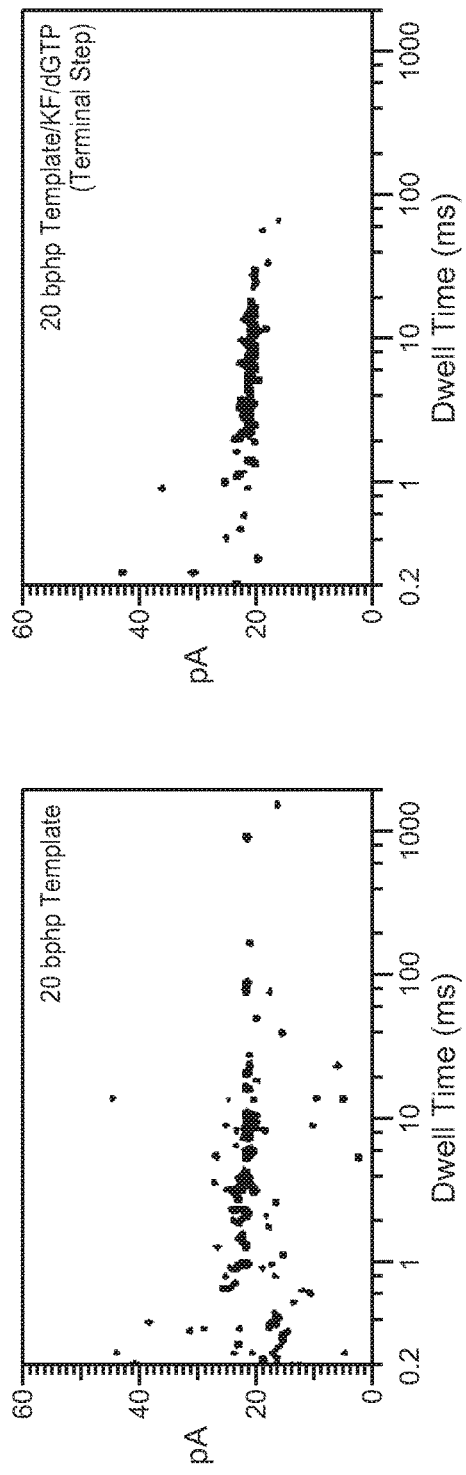
FIG. 19D
FIG. 19E

COMPOSITIONS, DEVICES, SYSTEMS, AND METHODS FOR USING A NANOPORE

CROSS-REFERENCE TO RELATED APPLICATIONS

The present application is a continuation application of U.S. patent application Ser. No. 14/919,315, filed 21 Oct. 2015, which claims priority from Ser. No. 14/300,453 filed 10 Jun. 2014, which claims priority from U.S. patent application Ser. No. 14/056,636 filed 17 Oct. 2013, which claims priority from U.S. patent application Ser. No. 13/615,183 filed 13 Sep. 2012, which claims priority from U.S. patent application Ser. No. 12/080,684 filed 4 Apr. 2008, which claims priority from U.S. Provisional Patent Application Ser. No. 60/921,787 entitled "Methods To Limit Enzyme Activity To One Molecule Or Complex Using A Nanopore", filed 4 Apr. 2007, U.S. Provisional Patent Application Ser. No. 60/931,115 entitled "Methods For Sequencing Polynucleotides By Synthesis Using A Nanopore", filed 21 May 2007, U.S. Provisional Patent Application Ser. No. 60/962,530 entitled "Methods For Positioning Single Molecules At A Defined Site" filed 30 Jul. 2007, U.S. Provisional Patent Application Ser. No. 60/967,539 entitled "Method For Manufacture Of Very Large Scale Arrays Of Independently Addressable Nanopores And Methods For Their Use", filed 4 Sep. 2007, and U.S. Provisional Patent Application Ser. No. 61/062,391 entitled "Feedback Control Of A Single Tethered Polynucleotide Suspended In A Nanopore To Repeatedly Probe Polynucleotide-Binding Proteins", filed 25 Jan. 2008, all of which are herein incorporated by reference in their entirety for all purposes.

STATEMENT OF GOVERNMENTAL SUPPORT

This invention was made partly using funds from the National Human Genome Research Institute grant numbers HG003703-01 and HG004035-01, and from the National Institute of General Medical Sciences grant number GM073617-01A1. The U.S. Federal Government has certain rights to the invention.

REFERENCE TO SEQUENCE LISTING, COMPUTER PROGRAM, OR COMPACT DISK

None.

BACKGROUND OF THE INVENTION

Field of the Invention

The invention herein disclosed provides for devices and methods that can regulate the time at which an individual polymer in a mixture is acted upon by another compound, for example, an enzyme. The invention is of particular use in the fields of molecular biology, structural biology, cell biology, molecular switches, molecular circuits, and molecular computational devices, and the manufacture thereof. The invention also relates to methods of using the compositions to diagnose whether a subject is susceptible to cancer, autoimmune diseases, cell cycle disorders, or other disorders.

Background

The invention relates to the field of compositions, methods, and apparatus for characterizing polynucleotides and other polymers.

Determining the nucleotide sequence of DNA and RNA in a rapid manner is a major goal of researchers in biotechnology, especially for projects seeking to obtain the sequence of entire genomes of organisms. In addition, rapidly determining the sequence of a polynucleotide is important for identifying genetic mutations and polymorphisms in individuals and populations of individuals.

Nanopore sequencing is one method of rapidly determining the sequence of polynucleotide molecules. Nanopore sequencing is based on the property of physically sensing the individual nucleotides (or physical changes in the environment of the nucleotides (that is, for example, an electric current)) within an individual polynucleotide (for example, DNA and RNA) as it traverses through a nanopore aperture. In principle, the sequence of a polynucleotide can be determined from a single molecule. However, in practice, it is preferred that a polynucleotide sequence be determined from a statistical average of data obtained from multiple passages of the same molecule or the passage of multiple molecules having the same polynucleotide sequence. The use of membrane channels to characterize polynucleotides as the molecules pass through the small ion channels has been studied by Kasianowicz et al. (Proc. Natl. Acad. Sci. USA. 93:13770-13773, 1996, incorporate herein by reference) by using an electric field to force single stranded RNA and DNA molecules through a 1.5 nanometer diameter nanopore aperture (for example, an ion channel) in a lipid bilayer membrane. The diameter of the nanopore aperture permitted only a single strand of a polynucleotide to traverse the nanopore aperture at any given time. As the polynucleotide traversed the nanopore aperture, the polynucleotide partially blocked the nanopore aperture, resulting in a transient decrease of ionic current. Since the length of the decrease in current is directly proportional to the length of the polynucleotide, Kasianowicz et al. (1996) were able to determine experimentally lengths of polynucleotides by measuring changes in the ionic current.

Baldarelli et al. (U.S. Pat. No. 6,015,714) and Church et al. (U.S. Pat. No. 5,795,782) describe the use of nanopores to characterize polynucleotides including DNA and RNA molecules on a monomer by monomer basis. In particular, Baldarelli et al. characterized and sequenced the polynucleotides by passing a polynucleotide through the nanopore aperture. The nanopore aperture is imbedded in a structure or an interface, which separates two media. As the polynucleotide passes through the nanopore aperture, the polynucleotide alters an ionic current by blocking the nanopore aperture. As the individual nucleotides pass through the nanopore aperture, each base/nucleotide alters the ionic current in a manner that allows the identification of the nucleotide transiently blocking the nanopore aperture, thereby allowing one to characterize the nucleotide composition of the polynucleotide and perhaps determine the nucleotide sequence of the polynucleotide.

One disadvantage of previous nanopore analysis techniques is controlling the rate at which the target polynucleotide is analyzed. As described by Kasianowicz, et al. (1996), nanopore analysis is a useful method for performing length determinations of polynucleotides. However, the translocation rate is nucleotide composition dependent and can range between $10^5$ to $10^7$ nucleotides per second under the measurement conditions outlined by Kasianowicz et al. (1996). Therefore, the correlation between any given polynucleotide's length and its translocation time is not straightforward. It is also anticipated that a higher degree of resolution with regard to both the composition and spatial relationship between nucleotide units within a polynucleotide can be obtained if the translocation rate is substantially reduced.

There is currently a need to provide compositions and methods that can be used in characterization of polymers, including polynucleotides and polypeptides, as well as diagnosis and prognosis of diseases and disorders.

BRIEF SUMMARY OF THE INVENTION

The invention provides thin film devices and methods for using the same. The subject devices comprise cis and trans chambers connected by an electrical communication means. The cis and trans chambers are separated by a thin film comprising at least one pore or channel. In one preferred embodiment, the thin film comprises a compound having a hydrophobic domain and a hydrophilic domain. In a more preferred embodiment, the thin film comprises a phospholipid. The devices further comprise a means for applying an electric field between the cis and the trans chambers. The pore or channel is shaped and sized having dimensions suitable for passaging a polymer. In one preferred embodiment the pore or channel accommodates a part but not all of the polymer. In one other preferred embodiment, the polymer is a polynucleotide. In an alternative preferred embodiment, the polymer is a polypeptide. Other polymers provided by the invention include polypeptides, phospholipids, polysaccharides, and polyketides.

In one embodiment, the thin film further comprises a compound having a binding affinity for the polymer. In one preferred embodiment the binding affinity ($K_a$) is at least $10^6$ l/mole. In a more preferred embodiment the $K_a$ is at least $10^8$ l/mole. In yet another preferred embodiment the compound is adjacent to at least one pore. In a more preferred embodiment the compound is a channel. In a yet more preferred embodiment the channel has biological activity. In a most preferred embodiment, the compound comprises the pore.

In one embodiment the compound comprises enzyme activity. The enzyme activity can be, for example, but not limited to, enzyme activity of proteases, kinases, phosphatases, hydrolases, oxidoreductases, isomerases, transferases, methylases, acetylases, ligases, lyases, and the like. In a more preferred embodiment the enzyme activity can be enzyme activity of DNA polymerase, RNA polymerase, endonuclease, exonuclease, DNA ligase, DNase, uracil-DNA glycosidase, ribosomes, kinase, phosphatase, methylase, acetylase, or the like.

In another embodiment the pore is sized and shaped to allow passage of an activator, wherein the activator is selected from the group consisting of ATP, $NAD^+$, $NADP^+$, diacylglycerol, phosphatidylserine, eicosinoids, retinoic acid, calciferol, ascorbic acid, neuropeptides, enkephalins, endorphins, 4-aminobutyrate (GABA), 5-hydroxytryptamine (5-HT), catecholamines, acetyl CoA, S-adenosylmethionine, and any other biological activator.

In yet another embodiment the pore is sized and shaped to allow passage of a cofactor, wherein the cofactor is selected from the group consisting of $Mg^{2+}$, $Mn^{2+}$, $Ca^{2+}$, ATP, $NAD^+$, $NADP^+$, and any other biological cofactor.

In a preferred embodiment the pore or channel is a pore molecule or a channel molecule and comprises a biological molecule, or a synthetic modified molecule, or altered biological molecule, or a combination thereof. Such biological molecules are, for example, but not limited to, an ion channel, a nucleoside channel, a peptide channel, a sugar transporter, a synaptic channel, a transmembrane receptor, such as GPCRs and the like, a nuclear pore, synthetic variants, chimeric variants, or the like. In one preferred embodiment the biological molecule is α-hemolysin.

In an alternative, the compound comprises non-enzyme biological activity. The compound having non-enzyme biological activity can be, for example, but not limited to, proteins, peptides, antibodies, antigens, nucleic acids, peptide nucleic acids (PNAs), locked nucleic acids (LNAs), morpholinos, sugars, lipids, glycophosphoinositols, lipopolysaccharides or the like. The compound can have antigenic activity. The compound can have selective binding properties whereby the polymer binds to the compound under a particular controlled environmental condition, but not when the environmental conditions are changed. Such conditions can be, for example, but not limited to, change in $[H^+]$, change in environmental temperature, change in stringency, change in hydrophobicity, change in hydrophilicity, or the like.

In another embodiment, the invention provides a compound, wherein the compound further comprises a linker molecule, the linker molecule selected from the group consisting of a thiol group, a sulfide group, a phosphate group, a sulfate group, a cyano group, a piperidine group, an Fmoc group, and a Boc group.

In one embodiment the thin film comprises a plurality of pores. In one embodiment the device comprises a plurality of electrodes.

Polymers

In another embodiment, the invention provides a method for controlling binding of an enzyme to a polymer, the method comprising: providing two separate, adjacent pools of a medium and an interface between the two pools, the interface having a channel so dimensioned as to allow sequential monomer-by-monomer passage from one pool to the other pool of only one polymer at a time; providing an enzyme having binding activity to a polymer; introducing the polymer into one of the two pools; introducing the enzyme into one of the two pools; applying a potential difference between the two pools, thereby creating a first polarity; reversing the potential difference a first time, thereby creating a second polarity; reversing the potential difference a second time to create the first polarity, thereby controlling the binding of the enzyme to the polymer. In a preferred embodiment, the medium is electrically conductive. In a more preferred embodiment, the medium is an aqueous solution. In another preferred embodiment, the method further comprises the steps of measuring the electrical current between the two pools; comparing the electrical current value ($I_1$) obtained at the first time the first polarity was induced with the electrical current value ($I_2$) obtained at the time the second time the first polarity was induced; and determining the difference between $I_1$ and $I_2$ thereby obtaining a difference value δI. In another preferred embodiment the method further comprises the steps of measuring the electrical current between the two pools; comparing the electrical current value ($I_1$) obtained at the first time the first polarity was induced with the electrical current value ($I_2$) obtained at a later time and determining the difference between $I_1$ and $I_2$ thereby obtaining a difference value δI. In a more preferred embodiment, the enzyme is selected from the group consisting of proteases, kinases, phosphatases, hydrolases, oxidoreductases, isomerases, transferases, methylases, acetylases, ligases, and lyases. In another alternative embodiment, the method further comprises the steps of providing reagents that initiate enzyme activity; introducing the reagents to the pool comprising the polynucleotide complex; and incubating the pool at a suitable temperature. In a more preferred embodiment, the reagents are selected from the group consisting of an activator and a cofactor. In a yet more preferred embodiment, the activator is introduced into the pool prior to introducing the cofactor. In a yet still further more preferred embodiment, the activator is selected from the group consisting of ATP, NAD$^+$, NADP$^+$, diacylglycerol, phosphatidylserine, eicosinoids, retinoic acid, calciferol, ascorbic acid, neuropeptides, enkephalins, endorphins, 4-aminobutyrate (GABA), 5-hydroxytryptamine (5-HT), catecholamines, acetyl CoA, and S-adenosylmethionine. In another still more preferred embodiment, the cofactor is selected from the group consisting of Mg$^{2+}$, Mn$^{2+}$, Ca$^{2+}$, ATP, NAD$^+$, and NADP$^+$. In another more preferred embodiment, the polymer is selected from the group consisting of polynucleotides, polypeptides, phospholipids, polysaccharides, and polyketides. In one embodiment the enzyme is introduced into the same pool as the polymer. In an alternative embodiment, the enzyme is introduced into the opposite pool.

Polynucleotides

In another embodiment, the invention provides a method for controlling binding of an enzyme to a partially double-stranded polynucleotide complex, the method comprising: providing two separate, adjacent pools of a medium and an interface between the two pools, the interface having a channel so dimensioned as to allow sequential monomer-by-monomer passage from one pool to the other pool of only one polynucleotide at a time; providing an enzyme having binding activity to a partially double-stranded polynucleotide complex; providing a polynucleotide complex comprising a first polynucleotide and a second polynucleotide, wherein a portion of the polynucleotide complex is double-stranded, and wherein the first polynucleotide further comprises a moiety that is incompatible with the second polynucleotide; introducing the polynucleotide complex into one of the two pools; introducing the enzyme into one of the two pools; applying a potential difference between the two pools, thereby creating a first polarity; reversing the potential difference a first time, thereby creating a second polarity; reversing the potential difference a second time to create the first polarity, thereby controlling the binding of the enzyme to the partially double-stranded polynucleotide complex. In a preferred embodiment, the medium is electrically conductive. In a more preferred embodiment, the medium is an aqueous solution. In a preferred embodiment, the moiety is selected from the group consisting of a peptide nucleic acid, a 2'-O-methyl group, a fluorescent compound, a derivatized nucleotide, and a nucleotide isomer. In another preferred embodiment, the method further comprises the steps of measuring the electrical current between the two pools; comparing the electrical current value obtained at the first time the first polarity was induced with the electrical current value obtained at the time the second time the first polarity was induced. In another preferred embodiment the method further comprises the steps of measuring the electrical current between the two pools; comparing the electrical current value obtained at the first time the first polarity was induced with the electrical current value obtained at a later time. In a more preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In another alternative embodiment, the method further comprises the steps of providing at least one reagent that initiates enzyme activity; introducing the reagent to the pool comprising the polynucleotide complex; and incubating the pool at a suitable temperature. In a more preferred embodiment, the reagent is selected from the group consisting of a deoxyribonucleotide and a cofactor. In a yet more preferred embodiment, the deoxyribonucleotide is introduced into the pool prior to introducing the cofactor. In another still more preferred embodiment, the cofactor is selected from the group consisting of Mg$^{2+}$, Mn$^{2+}$, Ca$^{2+}$, ATP, NAD$^+$, and NADP$^+$. In one embodiment the enzyme is introduced into the same pool as the polynucleotide. In an alternative embodiment, the enzyme is introduced into the opposite pool.

Polypeptides

In another embodiment, the invention provides a method for controlling binding of an enzyme to a polypeptide, the method comprising: providing two separate, adjacent pools of a medium and an interface between the two pools, the interface having a channel so dimensioned as to allow sequential monomer-by-monomer passage from one pool to the other pool of only one polypeptide at a time; providing an enzyme having binding activity to a polypeptide; providing a polypeptide comprising a modifiable amino acid residue; introducing the polypeptide into one of the two pools; introducing the enzyme into one of the two pools; applying a potential difference between the two pools, thereby creating a first polarity; reversing the potential difference a first time, thereby creating a second polarity; reversing the potential difference a second time to create the first polarity, thereby controlling the binding of the enzyme to the polypeptide. In a preferred embodiment, the medium is electrically conductive. In a more preferred embodiment, the medium is an aqueous solution. In a preferred embodiment, the moiety is selected from the group consisting of a peptide nucleic acid, a 2'-O-methyl group, a fluorescent compound, a derivatized nucleotide, and a nucleotide isomer. In another preferred embodiment, the method further comprises the steps of measuring the electrical current between the two pools; comparing the electrical current value obtained at the first time the first polarity was induced with the electrical current value obtained at the time the second time the first polarity was induced. In another preferred embodiment the method further comprises the steps of measuring the electrical current between the two pools; comparing the electrical current value obtained at the first time the first polarity was induced with the electrical current value obtained at a later time. In a more preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In another alternative embodiment, the method further comprises the steps of providing at least one reagent that initiates enzyme activity; introducing the reagent to the pool comprising the polynucleotide complex; and incubating the pool at a suitable temperature. In a more preferred embodiment, the reagent is selected from the group consisting of an activator and a cofactor. In a most preferred embodiment, the activator is selected from the group consisting of ATP, NAD$^+$, NADP$^+$, diacylglycerol, phosphatidylserine, acetyl CoA, and S-adenosylmethionine. In a yet more preferred embodiment, the activator is introduced into the pool prior to introducing the cofactor.

In another still more preferred embodiment, the cofactor is selected from the group consisting of Mg$^{2+}$, Mn$^{2+}$, Ca$^{2+}$, ATP, NAD$^+$, and NADP$^+$. In one embodiment the enzyme is introduced into the same pool as the polypeptide. In an alternative embodiment, the enzyme is introduced into the opposite pool.

The invention herein disclosed provides for devices and methods that can regulate the rate at which an individual polymer in a mixture is acted upon by another compound, for example, an enzyme. The devices and methods are also used to determine the nucleotide base sequence of a polynucleotide. The invention is of particular use in the fields of molecular biology, structural biology, cell biology, molecular switches, molecular circuits, and molecular computational devices, and the manufacture thereof.

In one alternative embodiment, the invention provides a method for controlling binding of an enzyme to a partially double-stranded polynucleotide complex and the method resulting in identifying the sequence of a polynucleotide, the method comprising the steps of: providing two separate adjacent pools comprising a medium, an interface between the two pools, the interface having a channel so dimensioned as to allow sequential monomer-by-monomer passage from the cis-side of the channel to the trans-side of the channel of only one polynucleotide strand at a time; providing an enzyme having binding activity to a partially double-stranded polynucleotide complex; providing at least one protected deoxyribonucleotide, the protection comprising using a protecting moiety; providing an annealing agent; providing a polynucleotide complex comprising a first polynucleotide and a second polynucleotide, wherein a portion of the polynucleotide complex is double-stranded and a portion is single-stranded; introducing the polynucleotide complex into one of the two pools; applying a potential difference between the two pools, thereby creating a first polarity, the first polarity causing the single stranded portion of the polynucleotide to transpose through the channel to the trans-side; introducing the enzyme and the protected deoxyribonucleotide into the same pool; introducing the annealing agent into the other pool; allowing the annealing agent to bind to the single-stranded polynucleotide; allowing the enzyme and the protected deoxyribonucleotide to bind to the polynucleotide; allowing the protected deoxyribonucleotide to be incorporated into the polynucleotide; reversing the potential difference a first time, thereby creating a second polarity; allowing the protected deoxyribonucleotide to release the protecting moiety and become deprotected; measuring the abundance of the protecting moiety; reversing the potential difference a second time to create the first polarity; repeating any one of the steps, thereby controlling the binding of the enzyme to the double-stranded polynucleotide complex and determining the sequence of the polynucleotide. In a preferred embodiment, the medium is electrically conductive. In a more preferred embodiment, the medium is an aqueous medium. In one preferred embodiment, the moiety is selected from the group consisting of a peptide nucleic acid, a 2'-O-methyl group, a fluorescent compound, anthocyanins, green fluorescent protein (GFP), β-glucuronidase, luciferase, Cy3, Cy5, a derivatized nucleotide, and a nucleotide isomer. In another preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In one alternative embodiment, the method further comprises the steps of measuring the electrical current between the two pools; comparing the electrical current value obtained at the first time the first polarity was induced with the electrical current value obtained at the time the second time the first polarity was induced. In another alternative embodiment, the method further comprises the steps of measuring the electrical current between the two pools; comparing the electrical current value obtained at the first time the first polarity was induced with the electrical current value obtained at a later time. In a yet further alternative embodiment, the method further comprises the steps of providing at least one reagent that initiates enzyme activity; introducing the reagent to the pool comprising the polynucleotide complex; and incubating the pool at a temperature sufficient to maintain enzyme activity. In a preferred embodiment, the reagent is a cofactor. In a more preferred embodiment, the cofactor is selected from the group consisting of $Mg^{2+}$, $Mn^{2+}$, $Ca^{2+}$, ATP, $NAD^+$, $NADP^+$, and S-adenosylmethionine. In another preferred embodiment, the protected deoxyribonucleotide comprises a deoxyribonucleotide selected from the group consisting of dATP, dGTP, dTTP, dCTP, and dUTP. In another more preferred embodiment, the reagent is selected from the group consisting of ddATP, ddGTP, ddTTP, ddCTP, and ddUTP. In a yet other preferred embodiment, the aqueous medium of at least one pool comprises an annealing agent. In a more preferred embodiment, the annealing agent selected from the group consisting of a complementary oligonucleotide and streptavidin.

The invention also provides a method for sensing the position of a molecule relative to a pore, the method comprising: providing two separate, adjacent pools of a medium and a structure between the two pools, the structure having an ion-permeable pore; providing a polyion; providing a molecule having binding activity to the polyion; introducing the polyion into one of the two pools; introducing the molecule into the same pool; applying a potential difference between the two pools, thereby creating a first polarity; measuring a first electrical current between the two pools, thereby sensing the position of a molecule relative to the pore. In a preferred embodiment, the molecule is a macromolecule, wherein the macromolecule selected from the group consisting of proteases, kinases, phosphatases, hydrolases, oxidoreductases, isomerases, transferases, methylases, acetylases, ligases, lyases, a transmembrane receptor, a receptor tyrosine kinase, a T-cell receptor, an MHC receptor, and a nuclear receptor. In another preferred embodiment the medium is electrically conductive. In a more preferred embodiment, the medium is an aqueous solution. In another preferred embodiment, the structure further comprises a compound, wherein the compound is selected from the group consisting of a thiol group, a sulfide group, a phosphate group, a sulfate group, a cyano group, a piperidine group, an Fmoc group, and a Boc group, silicon nitride, bifunctional alkyl sulfide, and gold. In another preferred embodiment, the polyion is selected from the group consisting of polynucleotides, polypeptides, phospholipids, polysaccharides, and polyketides. In alternative embodiment, the method further comprises the steps of reversing the potential difference a first time, thereby creating a second polarity; reversing the potential difference a second time to create the first polarity, measuring a second electrical current between the two pools, thereby further sensing the position of the molecule relative to the pore. In another alternative embodiment, the method further comprises the steps of measuring the electrical current between the two pools; comparing the electrical current value obtained at the first time the first polarity was induced with the electrical current value obtained at a later time. In a still further alternative embodiment, the method further comprises the steps of providing reagents that initiate enzyme activity; introducing the reagents to the pool comprising the polynucleotide complex; and incubating the pool at a suitable temperature. In a more preferred embodiment, the reagents are selected from the group consisting of an activator and a cofactor. In another more preferred embodiment, the activator is introduced into the pool prior to introducing the cofactor. In a still more preferred embodiment, the activator is selected from the group consisting of ATP, $NAD^+$, $NADP^+$, diacylglycerol, phosphatidylserine, eicosinoids, glycosyl phosphatidyl inositols, glycophosphoinositols, lipopolysaccharides, retinoic acid, calciferol, ascorbic acid, neuropeptides, enkephalins, endorphins, 4-aminobutyrate (GABA), 5-hydroxytryptamine (5-HT), catecholamines, acetyl CoA, and S-adenosylmethionine. In another still more preferred embodiment, the cofactor is selected from the group consisting of $Mg^{2+}$, $Mn^{2+}$, $Ca^{2+}$, ATP, $NAD^+$, and $NADP^+$.

In a preferred embodiment the pore or channel comprises a biological molecule, or a synthetic modified or altered biological molecule. Such biological molecules are, for example, but not limited to, an ion channel, such as α-hemolysin, a nucleoside channel, a peptide channel, a sugar transporter, a synaptic channel, a transmembrane receptor, such as GPCRs, a receptor tyrosine kinase, and the like, a T-cell receptor, an MHC receptor, a nuclear receptor, such as a steroid hormone receptor, a nuclear pore, or the like.

In an alternative embodiment, the compound comprises non-enzyme biological activity. The compound having non-enzyme biological activity can be, for example, but not limited to, proteins, peptides, antibodies, antigens, nucleic acids, peptide nucleic acids (PNAs), locked nucleic acids (LNAs), morpholinos, sugars, lipids, glycosyl phosphatidyl inositols, glycophosphoinositols, lipopolysaccharides, or the like. The compound can have antigenic activity. The compound can have ribozyme activity. The compound can have selective binding properties whereby the polymer binds to the compound under a particular controlled environmental condition, but not when the environmental conditions are changed. Such conditions can be, for example, but not limited to, change in $[H^+]$, change in environmental temperature, change in stringency, change in hydrophobicity, change in hydrophilicity, change in hydrophilicity, or the like.

In one embodiment the macromolecule comprises enzyme activity. The enzyme activity can be, for example, but not limited to, enzyme activity of proteases, kinases, phosphatases, hydrolases, oxidoreductases, isomerases, transferases, methylases, acetylases, ligases, lyases, and the like. In a more preferred embodiment the enzyme activity can be enzyme activity of DNA polymerase, RNA polymerase, endonuclease, exonuclease, DNA ligase, DNase, uracil-DNA glycosidase, kinase, phosphatase, methylase, acetylase, glucose oxidase, or the like. In an alternative embodiment, the macromolecule can comprise more than one enzyme activity, for example, the enzyme activity of a cytochrome P450 enzyme. In another alternative embodiment, the macromolecule can comprise more than one type of enzyme activity, for example, mammalian fatty acid synthase. In another embodiment the macromolecule comprises ribozyme activity.

In an alternative embodiment, the macromolecule comprises non-enzyme biological activity. The macromolecule having non-enzyme biological activity can be, for example, but not limited to, proteins, peptides, antibodies, antigens, nucleic acids, peptide nucleic acids (PNAs), locked nucleic acids (LNAs), morpholinos, sugars, phospholipids, lipids, glycosyl phosphatidyl inositols, glycophosphoinositols, lipopolysaccharides, or the like. The macromolecule can have polynucleotide-binding activity and/or polypeptide biosynthesis activity, such as, but not limited to, a ribosome or a nucleosome. The macromolecule can have antigenic activity. The macromolecule can have selective binding properties whereby the polymer binds to the macromolecule under a particular controlled environmental condition, but not when the environmental conditions are changed. Such conditions can be, for example, but not limited to, change in $[H^+]$, change in environmental temperature, change in stringency, change in hydrophobicity, change in hydrophilicity, or the like.

In another embodiment, the invention provides a compound, wherein the compound further comprises a linker molecule, the linker molecule selected from the group consisting of a thiol group, a sulfide group, a phosphate group, a sulfate group, a cyano group, a piperidine group, an Fmoc group, and a Boc group. In another embodiment the compound is selected from the group consisting of a bifunctional alkyl sulfide and gold.

In one embodiment the thin film comprises a plurality of pores. In one embodiment the device comprises a plurality of electrodes.

Single-channel thin film devices, systems, and methods for using the same are provided. The subject devices or systems comprise cis and trans chambers connected by an electrical communication means. At the cis end of the electrical communication means is a horizontal conical aperture sealed with a thin film that includes a single nanopore or channel. The devices further include a means for applying an electric field between the cis and trans chambers. The subject devices find use in applications in which the ionic current through a nanopore or channel is monitored, where such applications include the characterization of naturally occurring ion channels, the characterization of polymeric compounds, and the like.

The invention also provides a method for delivering a single macromolecule to a defined nanoscale site specified by a user.

The invention also provides a method for attaching a single macromolecule to a defined nanoscale site specified by a user.

The invention also provides a method for monitoring the function of a single macromolecule (or combination of single molecules) using ionic current through a nanoscopic pore.

The invention also provides a device or system for detecting binding of at least two compounds, the device comprising a mixed-signal semiconductor wafer, at least one electrochemical layer, the electrochemical layer comprising a semiconductor material, wherein the semiconductor material further comprises a surface modifier, wherein the electrochemical layer defines a plurality of orifices, the orifices comprising a chamber and a neck and wherein the chamber of the orifices co-localize with a metallization composition of the mixed-signal semiconductor wafer, wherein a portion of the orifice is plugged with a metal, wherein the metal is in electronic communication with the metallization composition, and wherein the orifice further comprises a thin film, the thin film forming a solvent-impermeable seal at the neck of the orifice, the thin film further comprising a pore, the pore further comprising a pore aperture. In a preferred embodiment, the compounds are biological compounds. In a more preferred embodiment, the biological compounds are selected from the group consisting of polynucleotides, polypeptides, phospholipids, polysaccharides, polyketides, proteases, kinases, phosphatases, hydrolases, oxidoreductases, isomerases, transferases, methylases, acetylases, ligases, and lyases. In another preferred embodiment, the semiconductor material is selected from the group consisting of silicon dioxide ($SiO_2$), silicon oxy nitride (SiON), silicon nitride (SiN), metal oxide, and metal silicate. In a more preferred embodiment, the semiconductor material is silicon dioxide. In another preferred embodiment, the surface modifier is a hydrocarbon. In a more preferred embodiment, the metallization composition is selected from the group consisting of nickel, gold, copper, and aluminum. In a most preferred embodiment, the metal is silver. In a preferred embodiment, the thin film is a molecular bilayer. In a more preferred embodiment, the thin film is a phospholipid bilayer. In one alternative embodiment, the orifice is between 0.5 and 3 µm in size. In a preferred embodiment, the orifice is between 1 and 2 µm in size. In a most preferred embodiment, the orifice is between 1.25 and 1.5 µm in size. In another preferred embodiment, the pore is a biological molecule. In a more preferred embodiment, the biological molecule is selected from the group consisting of an ion channel, a nucleoside channel, a peptide channel, a sugar transporter, a synaptic channel, a transmembrane receptor, and a nuclear pore. In a most preferred embodiment, the biological molecule is α-hemolysin. In a preferred embodiment, the pore aperture is between about 1 and 10 nm in size. In a more preferred embodiment, the pore aperture is between about 1 and 4 nm in size. In a most preferred embodiment, the pore aperture is between about 1 and 2 nm in size. In an alternative most preferred embodiment the pore aperture is between about 2 and 4 nm in size.

The invention also provides a finite state machine that can be used to detect and control binding of a molecule to a polymer. In one embodiment, the molecule is a protein. In a preferred embodiment, the protein is an enzyme. In one embodiment, the finite state machine can detect a polymer compound having a structural element that inhibits transposition of the polymer compound through a nanopore. In one preferred embodiment, the finite state machine can detect a polymer compound comprising a DNA hairpin structure in a nanopore, eject the compound comprising a DNA hairpin or DNA duplex structure from a nanopore after it has been detected but prior to unzipping the hairpin or DNA duplex structure. In an alternative embodiment the polymer compound comprises a derivatized nucleic acid. In yet another alternative embodiment, the polymer compound comprises a peptide nucleic acid.

In one embodiment the finite state machine can control binding of a molecule to a polymer at a rate of between about 5 Hz and 2000 Hz. The finite state machine can control binding of a molecule to a polymer at, for example, about 5 Hz, at about 10 Hz, at about 15 Hz, at about 20 Hz, at about 25 Hz, at about 30 Hz, at about 35 Hz, at about 40 Hz, at about 45 Hz, at about 50 Hz, at about 55 Hz, at about 60 Hz, at about 65 Hz, at about 70 Hz, at about 75 Hz, at about 80 Hz, at about 85 Hz, at about 90 Hz, at about 95 Hz, at about 100 Hz, at about 110 Hz, at about 120 Hz, at about 125 Hz, at about 130 Hz, at about 140 Hz, at about 150 Hz, at about 160 Hz, at about 170 Hz, at about 175 Hz, at about 180 Hz, at about 190 Hz, at about 200 Hz, at about 250 Hz, at about 300 Hz, at about 350 Hz, at about 400 Hz, at about 450 Hz, at about 500 Hz, at about 550 Hz, at about 600 Hz, at about 700 Hz, at about 750 Hz, at about 800 Hz, at about 850 Hz, at about 900 Hz, at about 950 Hz, at about 1000 Hz, at about 1125 Hz, at about 1150 Hz, at about 1175 Hz, at about 1200 Hz, at about 1250 Hz, at about 1300 Hz, at about 1350 Hz, at about 1400 Hz, at about 1450 Hz, at about 1500 Hz, at about 1550 Hz, at about 1600 Hz, at about 1700 Hz, at about 1750 Hz, at about 1800 Hz, at about 1850 Hz, at about 1900 Hz, at about 950 Hz, and at about 2000 Hz. In a preferred embodiment, the finite state machine can control binding of a molecule to a polymer at a rate of between about 25 Hz and about 250 Hz. In a more preferred embodiment the finite state machine can control binding of a molecule to a polymer at a rate of between about 45 Hz and about 120 Hz. In a most preferred embodiment the finite state machine can control binding of a molecule to a polymer at a rate of about 50 Hz.

The invention can be used to determine the nucleotide sequence of a polynucleotide. The invention can also be used to determine the relative affinity of an enzyme for binding a polynucleotide, thereby using the invention to identify novel enzyme compounds that bind to polynucleotides.

In one embodiment, the subject devices or systems comprise cis and trans chambers connected by an electrical communication means. The cis and trans chambers are separated by a thin film comprising at least one pore or channel. In one preferred embodiment, the thin film comprises a compound having a hydrophobic domain and a hydrophilic domain. In a more preferred embodiment, the thin film comprises a phospholipid. The devices further comprise a means for applying an electric field between the cis and the trans chambers. The devices further comprise a means for detecting the current between the cis and the trans chambers. The pore or channel is shaped and sized having dimensions suitable for passaging a polymer. In one preferred embodiment the pore or channel accommodates a substantial portion of the polymer. In a yet more preferred embodiment the pore or channel has biological activity. In another preferred embodiment, the polymer is a polynucleotide.

In one embodiment, the thin film further comprises a compound having a binding affinity for the polymer. In one preferred embodiment the binding affinity ($K_a$) is at least $10^6$ l/mole. In a more preferred embodiment the $K_a$ is at least $10^8$ l/mole. In yet another preferred embodiment the compound is adjacent to at least one pore. In a more preferred embodiment the compound comprises a polypeptide.

In one embodiment the compound comprises enzyme activity. The enzyme activity can be, for example, but not limited to, enzyme activity of proteases, kinases, phosphatases, hydrolases, oxidoreductases, isomerases, transferases, methylases, acetylases, ligases, lyases, and the like. In a more preferred embodiment the enzyme activity can be enzyme activity of DNA polymerase, RNA polymerase, endonuclease, exonuclease, DNA ligase, DNase, uracil-DNA glycosidase, kinase, phosphatase, methylase, acetylase, or the like.

In another embodiment the pore or channel is sized and shaped to allow passage of an activator, wherein the activator is selected from the group consisting of ATP, $NAD^+$, $NADP^+$, and any other biological activator.

In yet another embodiment the pore or channel is sized and shaped to allow passage of a cofactor, wherein the cofactor is selected from the group consisting of $Mg^{2+}$, $Mn^{2+}$, $Ca^{2+}$, ATP, $NAD^+$, $NADP^+$, and any other biological cofactor.

In a preferred embodiment the pore or channel comprises a biological molecule, or a synthetic modified or altered biological molecule. Such biological molecules are, for example, but not limited to, an ion channel, a nucleoside channel, a peptide channel, a sugar transporter, a synaptic channel, a transmembrane receptor, such as GPCRs and the like, a nuclear pore, or the like. In one preferred embodiment the biological molecule is α-hemolysin.

In an alternative, the compound comprises non-enzyme biological activity. The compound having non-enzyme biological activity can be, for example, but not limited to, proteins, peptides, antibodies, antigens, nucleic acids, peptide nucleic acids (PNAs), locked nucleic acids (LNAs), morpholinos, sugars, lipids, glycophosphoinositols, lipopolysaccharides, or the like. The compound can have antigenic activity. The compound can have selective binding properties whereby the polymer binds to the compound under a particular controlled environmental condition, but not when the environmental conditions are changed. Such conditions can be, for example, but not limited to, change in [H+], change in environmental temperature, change in stringency, change in hydrophobicity, change in hydrophilicity, or the like.

In yet another embodiment, the invention provides a method for controlling binding of an enzyme to a polynucleotide using voltage feedback control, the method resulting in repeated capture of and dissociation of the enzyme by the polynucleotide, the method comprising the steps of: providing two separate adjacent compartments comprising a medium, an interface between the two compartments, the interface having a channel so dimensioned as to allow sequential monomer-by-monomer passage from the cis-side of the channel to the trans-side of the channel of only one polynucleotide strand at a time; providing an enzyme having binding activity for a polynucleotide; providing a protected deoxyribonucleotide; providing a polynucleotide-binding compound; providing a polynucleotide complex, wherein a portion of the polynucleotide complex is double-stranded and a portion is single-stranded; introducing the polynucleotide complex into one of the two chambers; applying a potential difference between the two chambers, thereby creating a first polarity, the first polarity causing the single stranded portion of the polynucleotide to transpose through the channel to the trans-side; introducing the protected deoxyribonucleotide into the same chamber; introducing the enzyme into the same chamber; allowing the enzyme to bind to the polynucleotide; allowing the protected deoxyribonucleotide to bind to the polynucleotide; measuring the electrical current through the channel thereby detecting the binding of the enzyme and the protected deoxyribonucleotide to the polynucleotide; introducing the polynucleotide-binding compound into the other of the two chambers; decreasing the potential difference a first time, thereby creating a second polarity; allowing the polynucleotide-binding compound to bind to the single-stranded polynucleotide; reversing the potential difference, thereby creating a third polarity; reversing the potential difference a second time; measuring the electrical current through the channel, thereby detecting a polynucleotide alone or a polynucleotide bound to the enzyme and the protected deoxyribonucleotide; repeating any one of the steps, thereby controlling the binding of the enzyme to the polynucleotide. In a preferred embodiment, the method further comprises the steps of measuring the electrical current between the two chambers; comparing the electrical current value obtained at the first time the first polarity was induced with the electrical current value obtained at the time the second time the first polarity was induced. In another preferred embodiment, the method further comprises the steps of measuring the electrical current between the two chambers; comparing the electrical current value obtained at the first time the first polarity was induced with the electrical current value obtained at a later time. In a preferred embodiment, the polynucleotide-binding compound is selected from the group consisting of an oligonucleotide complementary to the polynucleotide, a peptide nucleic acid, a locked nucleic acid, a derivatized nucleotide, and a nucleotide isomer. In another preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In another preferred embodiment the medium is electrically conductive. In another preferred embodiment the medium is an aqueous medium. In another preferred embodiment the protected deoxyribonucleotide comprises a deoxyribonucleotide selected from the group consisting of dATP, dGTP, TTP, dCTP, UTP, and dUTP.

The method may further comprise the steps of providing at least one reagent that initiates enzyme activity; introducing the reagent to the chamber comprising the polynucleotide complex; and incubating the chamber at a temperature sufficient to maintain enzyme activity. In a preferred embodiment the reagent is a cofactor. In a more preferred embodiment, the cofactor is selected from the group consisting of $Mg^{2+}$, $Mn^{2+}$, $Ca^{2+}$, ATP, $NAD^+$, $NADP^+$, and S-adenosylmethionine. In another preferred embodiment, the reagent is selected from the group consisting of ddATP, ddGTP, ddTTP, ddCTP, and ddUTP.

In another embodiment of the invention, the invention provides a method for controlling binding of an enzyme to a polynucleotide using voltage feedback control, the method resulting in identifying the sequence of a polynucleotide, the method comprising the steps of: providing two separate adjacent chambers comprising a medium, an interface between the two chambers, the interface having a channel so dimensioned as to allow sequential monomer-by-monomer passage from the cis-side of the channel to the trans-side of the channel of only one polynucleotide strand at a time; providing an enzyme having binding activity for a polynucleotide; providing a protected deoxyribonucleotide; providing a polynucleotide-binding compound; providing a polynucleotide complex, wherein a portion of the polynucleotide complex is double-stranded and a portion is single-stranded; introducing the polynucleotide complex into one of the two chambers; applying a potential difference between the two chambers, thereby creating a first polarity, the first polarity causing the single stranded portion of the polynucleotide to transpose through the channel to the trans-side; introducing the protected deoxyribonucleotide into the same chamber; introducing the enzyme into the same chamber; allowing the enzyme to bind to the polynucleotide; allowing the protected deoxyribonucleotide to bind to the polynucleotide; measuring the electrical current through the channel thereby detecting the binding of the enzyme and the protected deoxyribonucleotide to the polynucleotide; introducing the polynucleotide-binding compound into the other of the two chambers; decreasing the potential difference a first time, thereby creating a second polarity; allowing the polynucleotide-binding compound to bind to the single-stranded polynucleotide; reversing the potential difference, thereby creating a third polarity; reversing the potential difference a second time; measuring the electrical current through the channel, thereby detecting a polynucleotide alone or a polynucleotide bound to the enzyme and the protected deoxyribonucleotide; repeating any one of the steps, thereby controlling the binding of the enzyme to the polynucleotide. In a preferred embodiment, the method further comprises the steps of measuring the electrical current between the two chambers; comparing the electrical current value obtained at the first time the first polarity was induced with the electrical current value obtained at the time the second time the first polarity was induced. In another preferred embodiment, the method further comprises the steps of measuring the electrical current between the two chambers; comparing the electrical current value obtained at the first time the first polarity was induced with the electrical current value obtained at a later time. In a preferred embodiment, the polynucleotide-binding compound is selected from the group consisting of an oligonucleotide complementary to the polynucleotide, a peptide nucleic acid, a locked nucleic acid, a derivatized nucleotide, and a nucleotide isomer. In another preferred embodiment, the enzyme is selected from the group consisting of DNA polymerase, RNA polymerase, endonuclease, exonuclease, DNA ligase, DNase, uracil-DNA glycosidase, kinase, phosphatase, methylase, and acetylase. In another preferred embodiment the medium is electrically conductive. In another preferred embodiment the medium is an aqueous medium. In another preferred embodiment the protected deoxyribonucleotide comprises a deoxyribonucleotide selected from the group consisting of dATP, dGTP, TTP, dCTP, UTP, and dUTP.

The method may further comprise the steps of providing at least one reagent that initiates enzyme activity; introducing the reagent to the chamber comprising the polynucleotide complex; and incubating the chamber at a temperature sufficient to maintain enzyme activity. In a preferred embodiment the reagent is a cofactor. In a more preferred embodiment, the cofactor is selected from the group consisting of $Mg^{2+}$, $Mn^{2+}$, $Ca^{2+}$, ATP, $NAD^+$, $NADP^+$, and S-adenosylmethionine. In another preferred embodiment, the reagent is selected from the group consisting of ddATP, ddGTP, ddTTP, ddCTP, and ddUTP.

In one embodiment the thin film comprises a plurality of pores. In one embodiment the device comprises a plurality of electrodes.

BRIEF DESCRIPTION OF THE DRAWINGS

FIG. 6A-6D illustrates an embodiment of the invention showing a method for positioning single molecules at a defined site.

FIG. 7A-7D illustrates an embodiment of the invention showing an alternative method for positioning single molecules at a defined site.

FIG. 14A depicts translocation through the nanopore of DNA alone (14 bp hairpin with a 36 nucleotide 5' overhang and 2'-3' dideoxycytidine terminus, template base at n=0 is C), while translocation of the 14bphp from complexes with KF, or from complexes with KF and dGTP, are shown in FIGS. 14B and 14C, respectively. For each of FIGS. 14A, 14B and 14C, a diagram of the nanopore with the associated complex (I), a current trace (II), and a dwell time event plot (III) are presented. In (IV), probability histograms of the base 10 logarithm of dwell time data are shown in solid. Close examination of the event plot in FIG. 14C(III) reveals that most long dwell time events are within 22 to 24 pA. An open bar subset histogram for the events within 22 to 24 pA is overlaid on probability histogram (FIG. 14C(IV)), revealing that the chosen range is dominated by long dwell time events.

FIG. 19A-19F illustrates a proposed mechanism for translocation of DNA/KF binary complex and DNA/KF/dGTP ternary complex through a nanopore. FIG. 19A shows a typical current trace when ternary complex is present. (I), (II) and (III) illustrate the configuration of the system for each section of the signal. FIGS. 19B and 19C show a dwell time event plot for a 14 bphp alone and the terminal step present in ternary complex events, respectively. The similarity of the dwell times in the two plots supports the perception that the terminal step is a result of KF dissociation. FIGS. 19D and 19E show the same as FIGS. 19B and 19C but for a 20 bphp. FIG. 19F shows a DNA only event (I) and a DNA/KF binary event (II) side by side. Note the absence of the terminal step in the DNA only event when compared to the enzyme-bound event.

FIG. 20A(I) shows that the FPGA diagnosed an enzyme event in the detection range [17.2 pA, 22.8 pA]. FIG. 20A(II) shows the FPGA continued to monitor the current to ensure it stayed within the detection range for at least 20 msec. Events lasting longer than 20 msec were diagnosed as a DNA/KF/dGTP ternary complex event. FIG. 20A(III) shows that upon diagnosis of a ternary complex, the FPGA reversed the voltage to −50 mV for 5 ms, ejecting the complex from the pore. The 180 mV capture voltage was then restored. FIG. 20B shows time probability histograms for 24±2.8 pA events with FPGA control (527 total events) and without FPGA control (155 total events).

FIG. 22A shows steps a)-c), and FIG. 22B shows step d). Step a) Captured hairpin or hairpin bound with KF at 180 mV. Step b) Hairpin was held in vestibule at 50 mV for trans-side primer to anneal (20 sec). Step c) Fished for KF at −20 mV for 5 sec. Step d) 180 mV applied to check for presence of KF. If enzyme binding does not occur, bare DNA was immediately detected in the pore. Otherwise, the FSM waited for KF to dissociate, leaving hairpin in vestibule (20 pA terminal step). In both cases, once bare DNA is present in the pore, the FSM reverses the voltage (−20 mV) before the hairpin unzips to fish for another KF. Steps c) through d) were repeated until the hairpin translocated.

DETAILED DESCRIPTION OF THE PREFERRED EMBODIMENT

Figure 1:
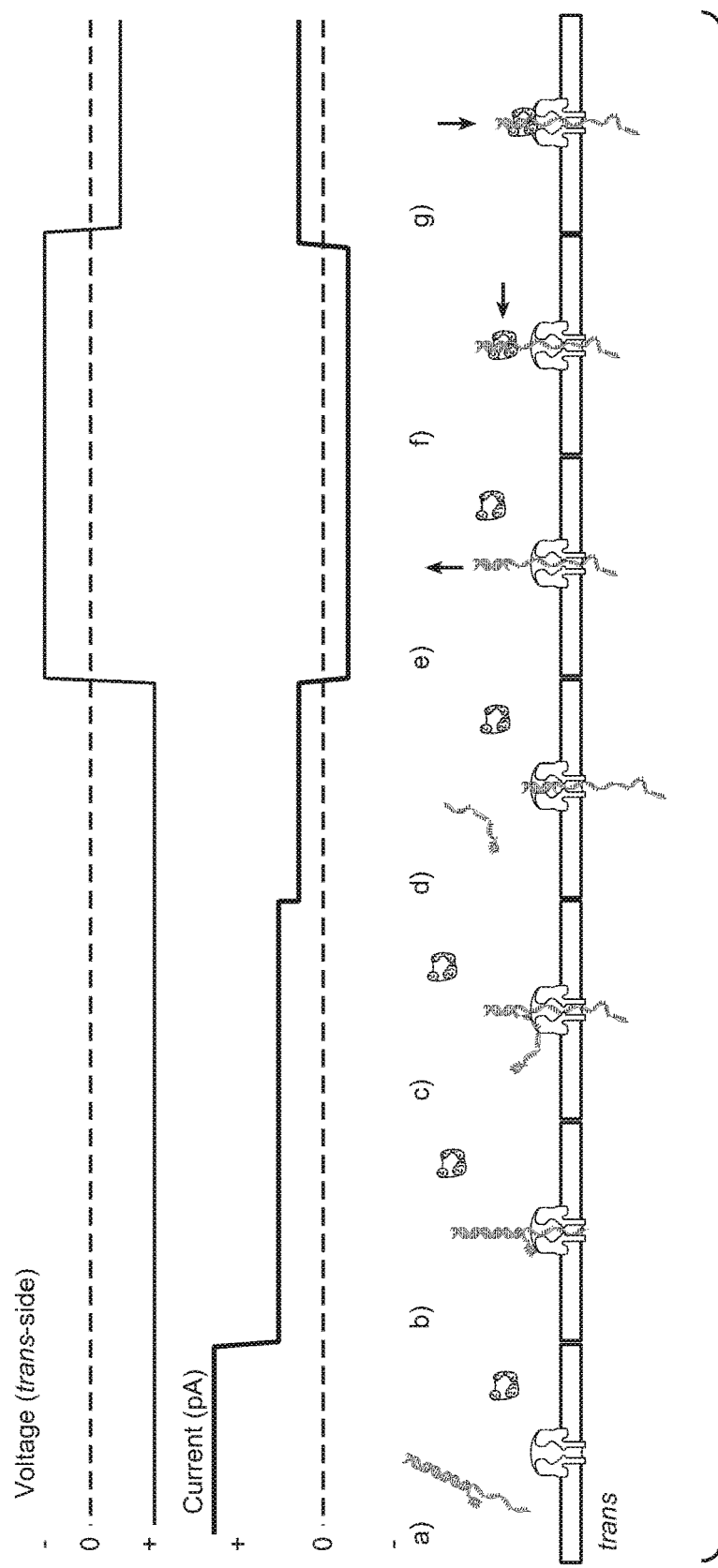
FIG. 1 illustrates an embodiment of the invention whereby enzyme binding to a polynucleotide is prevented by a blocking primer.

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "a nanopore" includes a plurality of such nanopores, and a reference to "a signal" is a reference to one or more signals and equivalents thereof, and so forth.

By "polynucleotide" is meant DNA or RNA, including any naturally occurring, synthetic, or modified nucleotide. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolo-pyrimidine triphosphate, 2-thiocytidine as well as the alpha-thiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

By "transport property" is meant a property measurable during polymer movement with respect to a nanopore. The transport property may be, for example, a function of the solvent, the polymer, a label on the polymer, other solutes (for example, ions), or an interaction between the nanopore and the solvent or polymer.

A "hairpin structure" is defined as an oligonucleotide having a nucleotide sequence that is about 6 to about 100 nucleotides in length, the first half of which nucleotide sequence is at least partially complementary to the second part thereof, thereby causing the polynucleotide to fold onto itself, forming a secondary hairpin structure.

A "hairpin shaped precursor" is defined as a hairpin structure that is processed by a Microprocessor complex and then by a Dicer enzyme complex, yielding an oligonucleotide that is about 16 to about 24 nucleotides in length.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences.

The term "incompatible" refers to the chemical property of a molecule whereby two molecules or portions thereof cannot interact with one another, physically, chemically, or both. For example, a portion of a polymer comprising nucleotides can be incompatible with a portion of a polymer comprising nucleotides and another chemical moiety, such as for example, a peptide nucleic acid, a 2'-O-methyl group, a fluorescent compound, a derivatized nucleotide, a nucleotide isomer, or the like. In another example, a portion of a polymer comprising amino acid residues can be incompatible with a portion of a polymer comprising amino acid residues and another chemical moiety, such as, for example, a sulfate group, a phosphate group, an acetyl group, a cyano group, a piperidine group, a fluorescent group, a sialic acid group, a mannose group, or the like.

"Alignment" refers to a number of DNA or amino acid sequences aligned by lengthwise comparison so that components in common (such as nucleotide bases or amino acid residues) may be visually and readily identified. The fraction or percentage of components in common is related to the homology or identity between the sequences. Alignments may be used to identify conserved domains and relatedness within these domains. An alignment may suitably be determined by means of computer programs known in the art, such as MACVECTOR software (1999) (Accelrys, Inc., San Diego, Calif.).

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Polynucleotide hybridization methods are disclosed in detail by Kashima et al. (1985) Nature 313: 402-404, and Sambrook et al. (1989) Molecular Cloning: A Laboratory Manual, 2nd Ed., Cold Spring Harbor Laboratory, Cold Spring Harbor, N.Y. ("Sambrook"); and by Haymes et al., "Nucleic Acid Hybridization: A Practical Approach", IRL Press, Washington, D.C. (1985), which references are incorporated herein by reference.

In general, stringency is determined by the incubation temperature, ionic strength of the solution, and concentration of denaturing agents (for example, formamide) used in a hybridization and washing procedure (for a more detailed description of establishing and determining stringency, see below). The degree to which two nucleic acids hybridize under various conditions of stringency is correlated with the extent of their similarity. Thus, similar polynucleotide sequences from a variety of sources, such as within an organism's genome (as in the case of paralogs) or from another organism (as in the case of orthologs) that may perform similar functions can be isolated on the basis of their ability to hybridize with known peptide-encoding sequences. Numerous variations are possible in the conditions and means by which polynucleotide hybridization can be performed to isolate sequences having similarity to sequences known in the art and are not limited to those explicitly disclosed herein. Such an approach may be used to isolate polynucleotide sequences having various degrees of similarity with disclosed sequences, such as, for example, sequences having 60% identity, or more preferably greater than about 70% identity, most preferably 72% or greater identity with disclosed sequences.

Single-channel thin film devices and methods for using the same are provided. The subject devices comprise cis and trans chambers connected by an electrical communication means. At the cis end of the electrical communication means is a horizontal conical aperture sealed with a thin film that includes a single nanopore or channel. The devices further include a means for applying an electric field between the cis and trans chambers. The subject devices find use in applications in which the ionic current through a nanopore or channel is monitored, where such applications include the characterization of naturally occurring ion channels, the characterization of polymeric compounds, and the like. Current sequencing methods are limited to read-lengths of about one kilobase (1000 base pairs identified), but the invention disclosed herein has potential for much longer read-lengths when compare with traditional bulk sequencing methods (Metzker (2005) Genome res. 15: 1767-1776; Rhee and Burns (2006) TIM 24: 580-586)

Devices that can be used to carry out the methods of the instant invention are described in for example, U.S. Pat. Nos. 5,795,782, 6,015,714, 6,267,872, 6,746,594, 6,428,959, and 6,617,113, each of which is hereby incorporated by reference in their entirety.

The invention is best understood by the examples and methods disclosed herein.

It is now understood that a means to control the time at which enzymatic activity begins for an individual polymer in a mixture would be an advantage. That is, absent such a control, initiation of enzyme activity (for example by addition of $Mg^{2+}$ cofactor to a bath containing enzyme and DNA) would begin at once and that enzyme-polynucleotide complexes would necessarily be at many points along the target strands when captured by the nanopore in a time series. At least five methods can be used to overcome these potential multiple interactions:

a) Microfluidics. A factor for inducing enzyme activity may be added only after an enzyme-polynucleotide complex is captured by the pore. After that polynucleotide is processed, the bath can be flushed and a new population of polynucleotide targets added absent the inducing factor. The cycle is then repeated.

b) Protein Engineering. By covalently linking an enzyme to a pore, it can be possible to have only one enzyme in the system and it will be immediately adjacent to the pore (some methods to achieve this are articulated in U.S. application Ser. No. 10/739,585).

c) Block Activity of Enzymes in Bulk Phase Using an Agent Released Only by Capture of a Complex in the Nanopore. This is illustrated by examples in the figures (FIGS. 1 and 2) and described herein.

Figure 2:
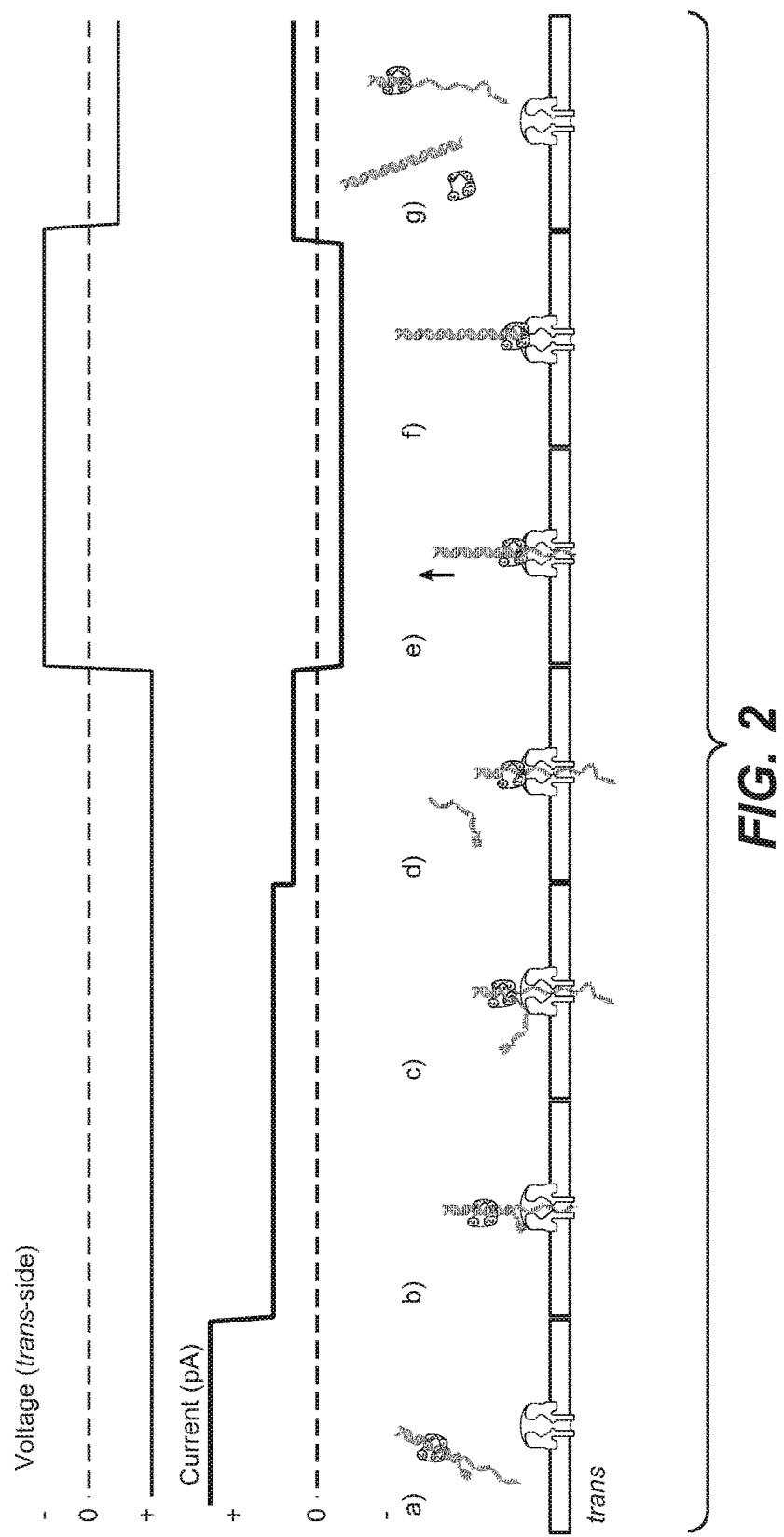
FIG. 2 illustrates an embodiment of the invention whereby enzyme catalytic activity upon a polynucleotide is prevented by a blocking primer.

Assume a DNA primer-template pair (at about 1 µM) in a solution that contains all required dNTPs (at about 200 µM each), $Mg^{2+}$ (at about 5 mM), and a processive DNA polymerase (at about 1 µM). The solution is in contact with a single nanopore (for example, αhemolysin) with an applied voltage such that negatively charged DNA is drawn into the pore. Each primer-template pair is also annealed to a sequence specific molecule at (or close to) the first base that will be added to the primer strand (position n=0). This molecule may have any of numerous structures but will likely be PNA or 2'-O-methyl substituted DNA in the early trials. This blocking molecule either inhibits binding of the polymerase at the initiation site (FIG. 1) or it allows binding but prevents strand synthesis (FIG. 2). The blocking molecule includes a loop that is sufficiently large that it cannot enter the nanopore. Thus, when the strand is pulled into the pore under applied voltage, this loop is hung-up at the pore orifice. This initiates unzipping of the block from the primer template and the blocking primer dissociates. Polymerase binding and polymerase-catalyzed strand synthesis can follow. The point of this method is that only the strand captured by the nanopore is unlocked from the blocking primer at the instant it is to be examined. When optimized, a 100 µl volume containing 1 µM of DNA primer/template represents one nanopore-activated molecule in $6 \times 10^{13}$ molecules total.

d) Deliver a Cofactor Through the Pore from the Trans-Side to the Cis-Side (Containing Enzyme). This can effectively restrict the required factor to the volume immediately adjacent to the pore. An example is $Mg^{2+}$. This is illustrated by examples in the figure (FIG. 3) and described herein.

Figure 3:
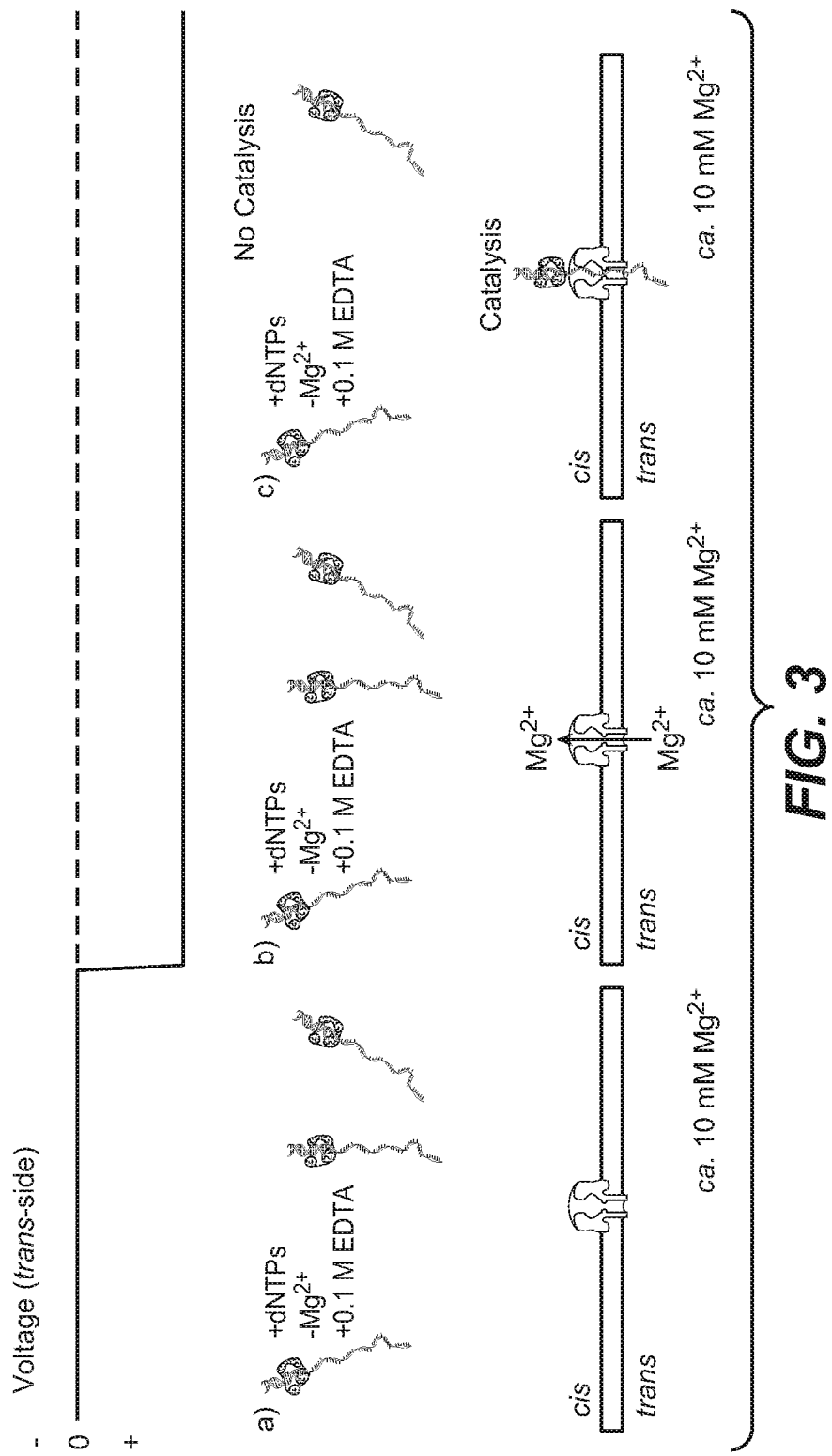
FIG. 3 illustrates an embodiment of the invention whereby enzyme catalytic activity upon a polynucleotide is activated by injection of $Mg^{2+}$ across the nanopore.

An example of this approach is illustrated in FIG. 3. $Mg^{2+}$ is a co-factor essential for catalytic activity by many DNA and/or RNA modifying enzymes including polynucleotide polymerases. In this scenario, $Mg^{2+}$ at greater than millimolar concentrations are added to the trans compartment. The cis compartment comprises all the other reagents, enzymes, and substrates necessary for catalysis. The cis compartment also comprises trace concentrations of EDTA (at about 0.1 mM) to ensure that free $[Mg^2]$ on the cis side is effectively zero in bulk phase. Since $Mg^{2+}$ is a divalent cation under physiological conditions, an applied voltage that attracts a polynucleotide into the nanopore (trans side+) would drive $Mg^{2+}$ in the opposite direction towards the cis compartment. Thus, in the volume (area of medium) immediately adjacent to the pore aperture, the free $[Mg^2]$ is a function of the voltage-driven flux from the trans side to the cis side across the nanopore minus the $Mg^{2+}$ fraction complexed by 0.1 mM EDTA and minus the rate of $Mg^{2+}$ diffusion away from the volume (area of medium) adjacent to the nanopore aperture. $[Mg^2]$ in the bulk volume remains effectively zero and is dominated by EDTA complexation of divalent metal(s).

e) Deliver ssDNA Template Through the Pore from the Trans Side to the Cis Side Containing Enzyme. This can effectively restrict enzyme processing of the template to the molecule captured in the pore. All other template strands are isolated from enzymes by the impermeable layer (a bilayer for example) supporting the channel.

Enzymes that interact with polynucleotides are known to those of skill in the art and can include, but are not limited to, DNA polymerase such as a DNA polymerase selected from *E. coli* DNA polymerase I, *E. coli* DNA polymerase I Large Fragment (Klenow fragment), phage T7 DNA polymerase, Phi-29 DNA polymerase, *Thermus aquaticus* (Taq) DNA polymerase, *Thermus flavus* (Tfl) DNA polymerase, *Thermus Thermophilus* (Tth) DNA polymerase, *Thermococcus litoralis* (Tli) DNA polymerase, *Pyrococcus furiosus* (Pfu) DNA polymerase, VENT DNA polymerase, *Bacillus stearothermophilus* (Bst) DNA polymerase, AMV reverse transcriptase, MMLV reverse transcriptase, and HIV-1 reverse transcriptase, RNA polymerase such as RNA polymerase selected from T7 RNA polymerase, T3 RNA polymerase, SP6 RNA polymerase, and *E. coli* RNA polymerase, and an exonuclease such as exonuclease Lambda, T7 Exonuclease, Exo III, $RecJ_1$ Exonuclease, Exo I, and Exo T.

Nanopore-Coupled Sequencing by Synthesis

This is a technique for sequencing of single DNA molecules. It combines features of conventional sequencing by synthesis (SBS) with novel nanopore analysis of single DNA molecules under electronic and biochemical feedback control. It relies upon 3' terminator technology, specifically reversible terminator technology.

Figure 4:
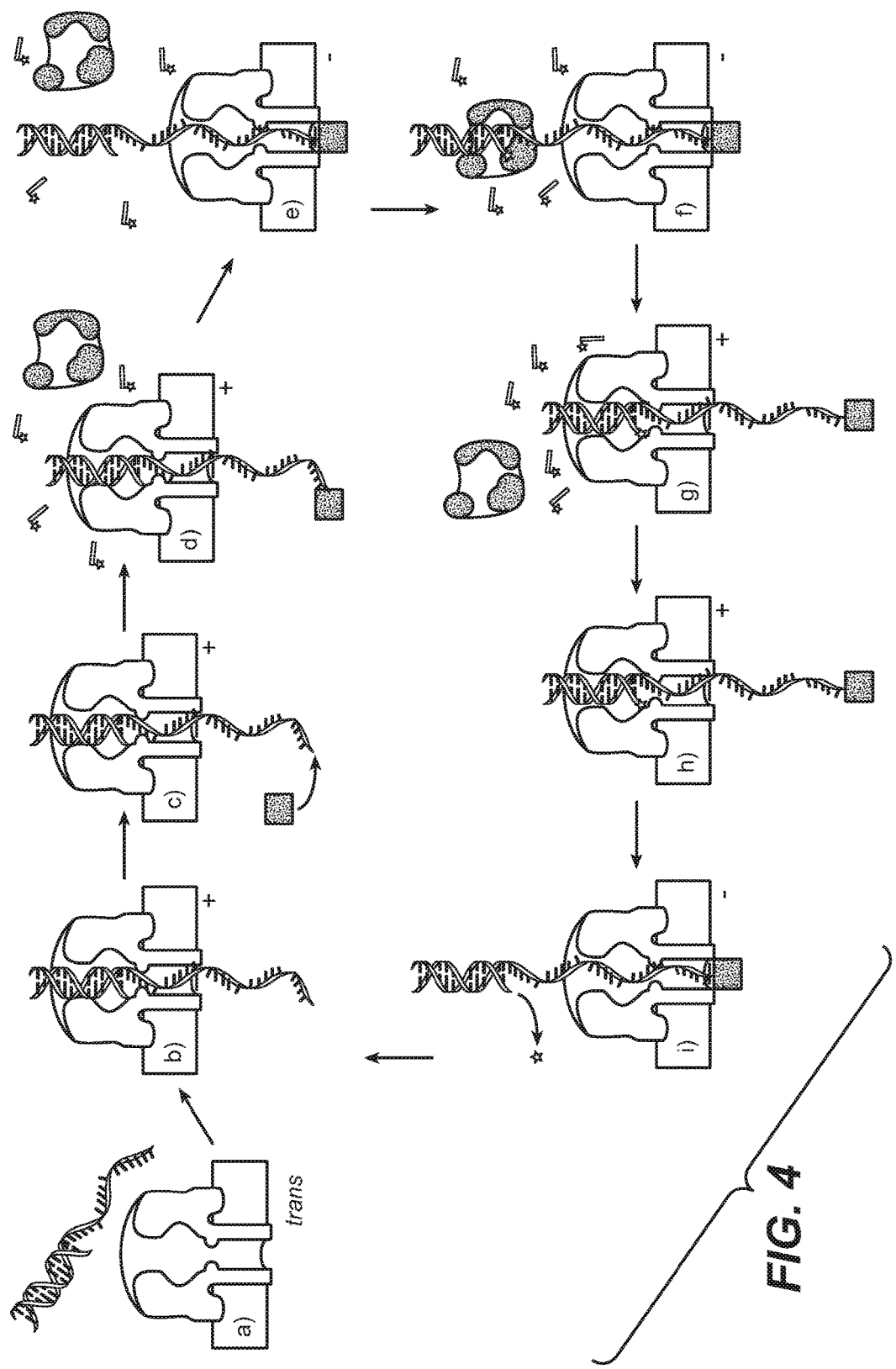
FIG. 4 illustrates an embodiment of the invention showing a method for sequencing single polynucleotide molecules.

The basic strategy is outlined in FIG. 4 for a single nanopore. Our laboratory has developed a strategy to perform this analysis on a chip with up to 400,000 pores. Design and fabrication of such a chip are disclosed below.

As illustrated in FIG. 4, A DNA molecule with both doubled-stranded and single-stranded segments is captured in a nanoscale pore under an applied voltage (trans side positive) (Step a: FIG. 4). DNA of this nature can be generated by timed exonuclease digestion of restriction fragments from genomic DNA or from BAC clones etc. The nanopore is large enough to permit translocation of the ssDNA segment, but the double-stranded segment cannot translocate because its diameter is too large to fit through the narrowest part of the pore. The α-hemolysin pore is ideal for this and is therefore used to illustrate the technique. Strand capture and entry of the duplex segment into the pore vestibule can be confirmed based on current amplitude. Once this is achieved, the voltage is reduced under feedback control (Step b: FIG. 4). At this point, the duplex terminus can be examined and identified by any of several techniques. For example, an earlier patent from this laboratory demonstrated that duplex termini can be identified based on DC current impedance alone. At the same time, the 5'-end of the ssDNA on the trans side of the channel is annealed to an agent (for example, a complementary oligonucleotide or streptavidin) that keeps the strand in the pore indefinitely.

Once the DNA strand is captured and the terminus identified, the cis compartment is perfused with a buffer containing $Mg^{2+}$, a DNA polymerase (for example, the Klenow fragment (KF) of DNA polymerase), and each of the four dNTPs protected with a distinct reversible terminator or by an identical reversible terminator (Step c: FIG. 4). The membrane potential is then reversed thus driving the duplex terminus of the target strand into the cis compartment containing the polymerase and substrates (Step c: FIG. 4). Sufficient time is then allowed for the correct protected dNTP to be added to the target (Step e: FIG. 4). When that time has elapsed, the voltage is reversed once again (trans-side positive; Step f: FIG. 4). The duplex terminus is pulled next to the pore's limiting-aperture where the identity of the added nucleotide is established. If no protected nucleotide has been added, the signal will be the same as in Step b. If this is the case, Steps d to f are repeated until the correct nucleotide is added and identified. Following confirmed addition of the protected nucleotide, the cis compartment is perfused and a deprotecting buffer is added (Step g: FIG. 4). Alternatively, we envision a scenario where a deprotecting agent located only near the nanopore is activated or deactivated under our control that would eliminate the need for perfusion. The deprotecting agent may be an enzyme (for example, alkaline phosphatase), light, or a solute (for example, palladium to catalyze deallylation). After perfusion, a trans-side negative potential is established, driving the duplex terminus into the cis compartment where the reversible terminator can be removed (Step h: FIG. 4). Following this reaction, a trans-side positive potential is re-established, drawing the duplex terminus back to the limiting aperture where it can be examined to determine if deprotection has been successfully achieved, and to confirm the identity of the last base (Step i: FIG. 4). In the event that deprotection is not successful, steps h and i are repeated. If deprotection was successful, the cycle is repeated at step b.

Figure 5:
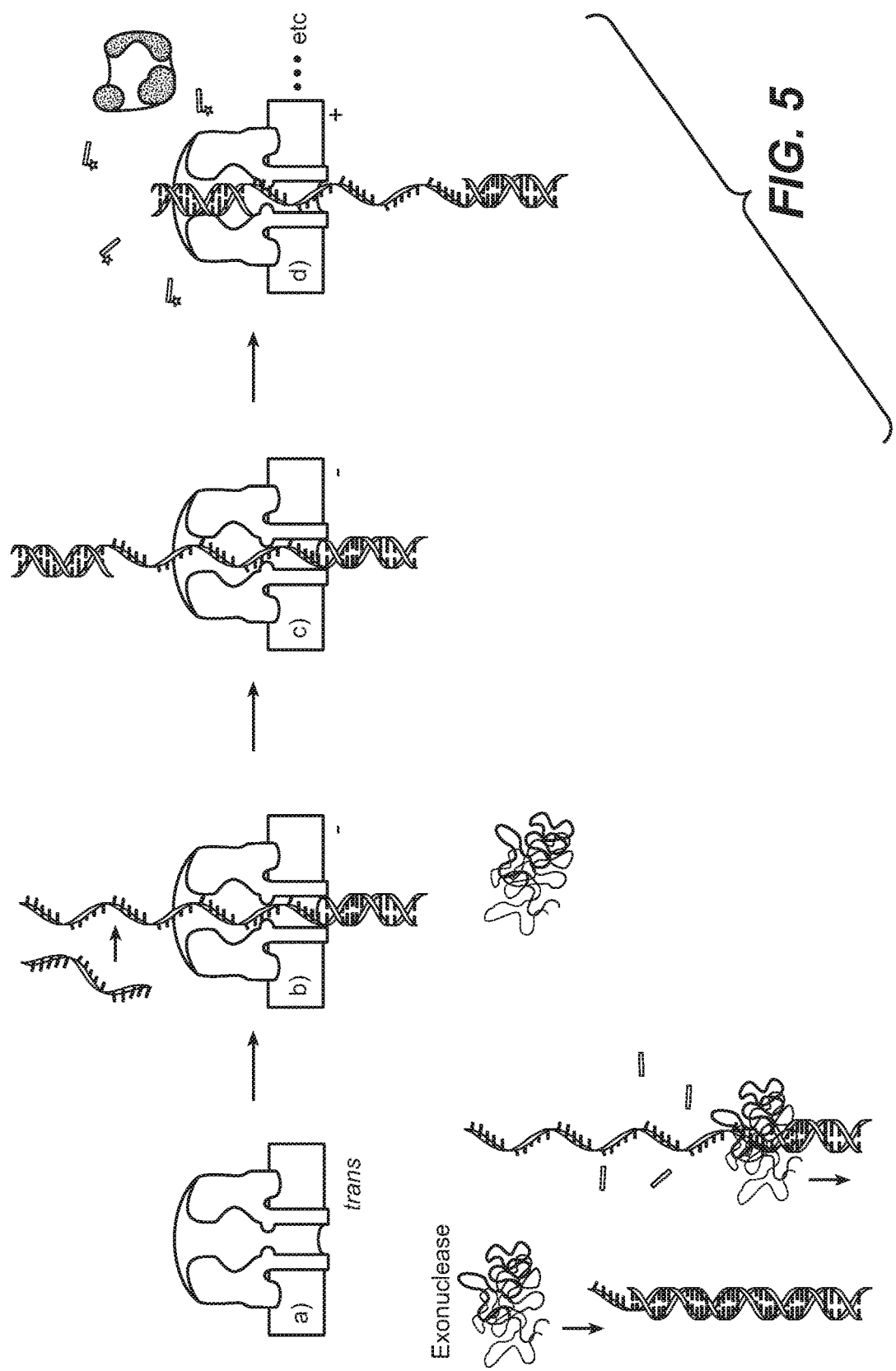
FIG. 5 illustrates an embodiment of the invention showing an alternative method for sequencing single polynucleotide molecules.

The scenario illustrated in FIG. 5 is similar to that illustrated in FIG. 4 except that exonuclease digestion takes place on the trans side of the channel and the DNA is captured in reverse orientation compared to FIG. 4. In this strategy, the template strand is held in place on the cis side by the primer from which strand synthesis originates. The advantage of this scenario is that ssDNA fed into to the nanopore can be generated in blocks by a series of timed exonuclease digestions in the trans compartment. Thus, most of the template would be as dsDNA. For example, if the exonuclease cut at 10 ms per base (on average), a 1000 base overhang could be generated at the end of a 20 kb dsDNA target. When about 1000 bases were successfully filled in by nanopore-coupled SBS, the exonuclease (or a required cofactor) could be re-added to the trans compartment and allowed to react for an additional 10 seconds. The newly generated ssDNA would be filled in base-by-base in the cis compartment as before. This would be repeated in approximately two rounds of 1000 bases to complete the 20 kb fragment.

The pore aperture can vary in dimensions, for example it can have a diameter of between about 0.5 nm and 10 nm in size. For example, the diameter can be about 0.5 nm, 1 nm, 1.25 nm, 1.5 nm, 1.75 nm, 2 nm, 2.25 nm, 2.5 nm, 2.75 nm, 3 nm, 3.5 nm, 4 nm, 4.5 nm, 5 nm, 6 nm, 7 nm, 8 nm, 9 nm, 10 nm, or any dimension therebetween.

Nanopore-coupled sequencing by synthesis has several advantages over conventional SBS, but the main advantages are these:

1) Nucleotide addition and reversible terminator removal can be directly measured on the individual target strand.

2) The system is controlled both electronically and biochemically so that nucleotide addition and deprotection steps can be repeated rapidly until they are successful.

3) A very long DNA molecule can be captured, manipulated, and quantitatively retained in the pore for an indefinite period.

4) The volume of reagents that are used can be very small (on the order of 100 µl), and it is possible that a given volume can be recycled hundreds of times. With further development, it may be possible to control activation and deactivation of the deprotection step at the nanopore orifice. This would completely eliminate the need for perfusion.

As is true with conventional SBS, this assay can be performed in parallel. We envision as many as 400,000 independently addressable pores on a 1 cm×1 cm chip that can be fabricated using conventional lithography (see separate disclosure below).

Here we propose polynucleotides that can be used to place and attach macromolecules and other polyanions/polycations at the nanopore aperture. Such macromolecules and polymers can be, for example, a polynucleotide-binding protein, such as, but not limited to a polynucleotide polymerase at the nanopore orifice. A nanopore has the useful property of bringing virtually any desired macromolecular structure to a defined site that can be specified by the user. After being placed at the nanopore site, macromolecular functions can be monitored by the user in a variety of ways. This method can be applied to macromolecules such as, but not limited to, enzymes, receptor proteins, ribozymes, and ribosomes. The method can be applied either to biological pores, or to solid state pores produced in thin inorganic membranes.

The basis of this invention is that a sufficiently long strand of an ionized polymer can be attached to the desired macromolecule, either by covalent or non-covalent bonds. The polymer is then drawn through the nanopore by an electrical voltage applied across the membrane. In some applications, it may be necessary to regulate the force on the macromolecule by varying the voltage acting across the pore. As a result, the macromolecule is placed at the site of the pore with sub-nanometer precision. The macromolecule is then maintained at the pore site either by the electrical force produced by the transmembrane voltage, or by a covalent bond that is engineered between the macromolecule and the pore, or the surface adjacent to the pore. More than one macromolecule can be attached in series if desired.

Functions of the single macromolecule can then be monitored by electrical effects produced at the pore. For instance, the ionic current through the pore can be measured and molecular functions are detected as modulations of the current. Alternatively, an electrode such as a carbon nanotube is placed across the pore and molecular functions are detected by modulations of the electronic current through the nanotube.

Exemplary Uses of the Invention (1) A nanopore device can be used to monitor the turnover of enzymes such as exonucleases and polymerases, which have important applications in DNA sequencing.

(2) A nanopore device can function as a biosensor to monitor the interaction between soluble substances such as enzyme substrates or signaling molecules. Examples include blood components such as glucose, uric acid and urea, hormones such as steroids and cytokines, and pharmaceutical agents that exert their function by binding to receptor molecules.

(3) A nanopore device can monitor in real time the function of important biological structures such as ribosomes, and perform this operation with a single functional unit.

FIGS. 6 through 8 illustrate exemplary embodiments of the invention.

FIG. 6

FIG. 6A illustrates a nanopore device comprising a pore aperture (1) in a substrate or structure (2) having a compound (3) bound adjacent to the pore aperture; the substrate or structure defining a cis side and a trans side. FIG. 6A further shows a molecule or macromolecule (4) bound to a polymer (5) to create a macromolecule/polymer complex, the polymer further comprising an incompletely synthesized portion (6).

As illustrated by FIG. 6B, a voltage gradient is applied to the device to draw the macromolecule/polymer complex to the cis side of the substrate or structure. The incompletely synthesized portion (6) has dimensions sufficient to pass through the pore aperture. Also illustrated are monomers (7) present on the cis side. The change in location of the macromolecule/polymer complex can be measured by the change in current (arrow; δI) across the pore aperture. The macromolecule then incorporates the monomers into the polymer to create a completely synthesized polymer (8) as shown in FIG. 6C.

The voltage gradient is then reversed, and as illustrated in FIG. 6C, the completely synthesized polymer is released from the macromolecule, thereby further creating a change in current (δI). This may be exemplified by using a DNA polymerase as the macromolecule.

In the alternative, as illustrated in FIG. 6D, the macromolecule excises the incompletely synthesized portion from the polymer, thereby releasing the incompletely synthesized portion (6) from the macromolecule/polymer complex. The voltage gradient is then reversed and the polymer (5) is released from the macromolecule. These events can also be measured by a change in the current (arrow; δI). This may be exemplified by using an endonuclease enzyme as the macromolecule.

FIG. 7

FIG. 7A illustrates a nanopore device comprising a pore aperture (1) in a substrate or structure (2) having a compound (3) bound adjacent to the pore aperture; the substrate or structure defining a cis side and a trans side. FIG. 7A further shows a molecule or macromolecule (4) bound to a polymer (5) to create a macromolecule/polymer complex, the macromolecule further comprising a high affinity binding site (9) for a ligand (10), FIG. 7B.

As illustrated by FIG. 7B, a voltage gradient is applied to the device to draw the macromolecule/polymer complex to the cis side of the substrate or structure. The polymer (5) is then covalently bound to the compound (3) thereby bringing adjacent to the pore aperture (1). The change in location of the macromolecule/polymer complex can be measured by the change in current (arrow; 61) across the pore aperture.

The ligand (10) is then allowed to bind to the high affinity binding site (9), and as illustrated in FIG. 7C, thereby further creating a change in current (arrow; δI). This may be exemplified by using a steroid hormone receptor as the macromolecule and a polyaspartic acid as the polymer.

In the alternative, as illustrated in FIG. 7D, the macromolecule metabolizes the ligand into two products (11), thereby releasing the products from the macromolecule/polymer complex. The voltage gradient is then reversed and the products are released from the macromolecule. These events can also be measured by a change in the current (δI). This may be exemplified by using a glucose oxidase enzyme or a protein phosphatase enzyme as the macromolecule.
FIG. 8

Figure 8A:
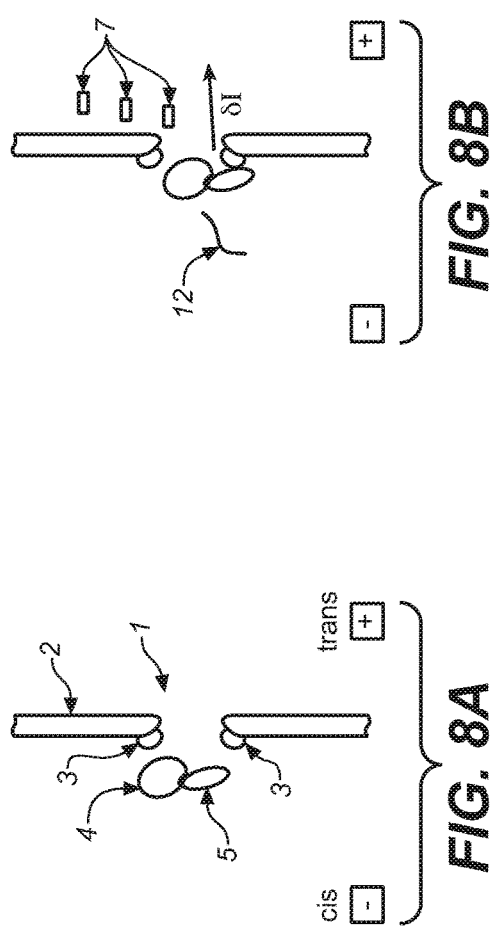
FIG. 8A-8D illustrates an embodiment of the invention showing another alternative method for positioning single molecules at a defined site.

FIG. 8A illustrates a nanopore device comprising a pore aperture (1) in a substrate or structure (2) having a compound (3) bound adjacent to the pore aperture; the substrate or structure defining a cis side and a trans side. FIG. 8A further shows a molecule or macromolecule (4) bound to a first polymer (5) to create a macromolecule/polymer complex.

Figure 8B:
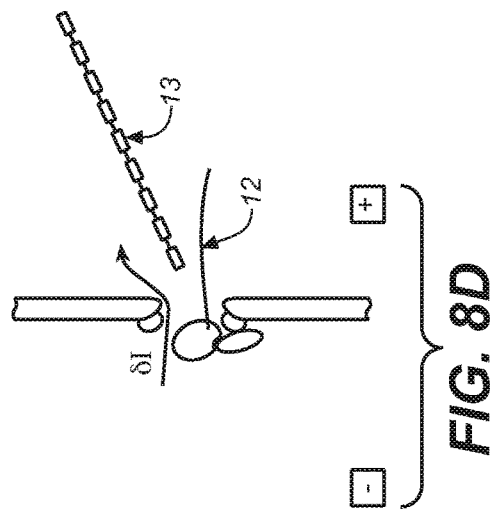

As illustrated by FIG. 8B, a voltage gradient is applied to the device to draw the macromolecule/polymer complex to the cis side of the substrate or structure. Also illustrated are a second polymer (12) present on the cis side and monomers (7) present on the trans side. In the alternative, the monomers (7) may be on the cis side (not shown). The polymer (5) is then covalently bound to the compound (3) thereby bringing adjacent to the pore aperture (1). The change in location of the macromolecule/polymer complex can be measured by the change in current (arrow; δI) across the pore aperture.

Figure 8C:
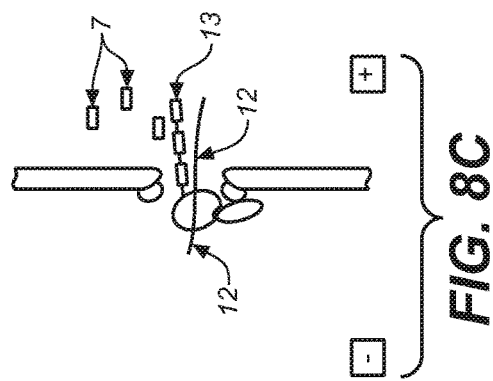
Figure 8D:
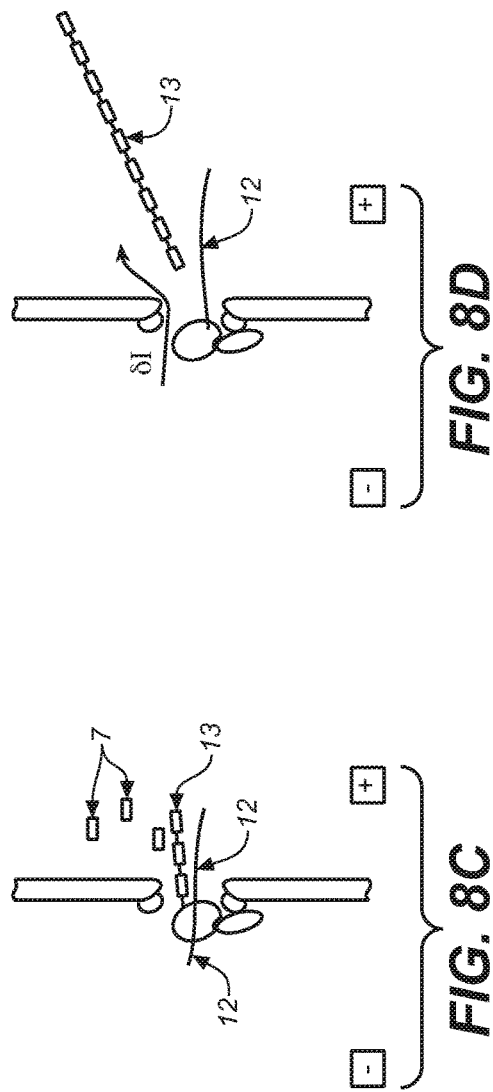

As illustrated in FIG. 8C, the second polymer (12) binds to the macromolecule (4) and is drawn by the potential difference though the aperture to the trans side. As the second polymer is drawn through the macromolecule co-ordinately synthesizes a third polymer (13) using the monomers (7), thereby further creating a change in current across the pore aperture (see FIG. 8D). In the alternative, the third polymer (13) can be synthesized on the cis side (not shown). These events can also be measured by a change in the current (δI). This may be exemplified by using a ribosome as the macromolecule and a messenger RNA as the first polymer. In an alternative, a ribosome may be used as the macromolecule and a polyaspartic acid as the third polymer.

Manufacture of Single Channel Thin Film Devices

Single-channel thin film devices and methods for using the same are provided. The subject devices comprise a mixed-signal semiconductor wafer, at least one electrochemical layer, the electrochemical layer comprising a semiconductor material, such as silicon dioxide or the like, wherein the semiconductor material further comprises a surface modifier, such as a hydrocarbon, wherein the electrochemical layer defines a plurality of orifices, the orifices comprising a chamber and a neck and wherein the chamber of the orifices co-localize with a first metal composition of the mixed-signal semiconductor wafer, wherein a portion of the orifice is plugged with a second metal, for example, silver, wherein the second metal is in electronic communication with the first metal, and wherein the orifice further comprises a thin film, such as a phospholipid bilayer, the thin film forming a solvent-impermeable seal at the neck of the orifice, the thin film further comprising a pore, and wherein the orifice encloses an aqueous phase and a gas phase. In a preferred embodiment the metallization layer comprises a metal, or metal alloy, such as, but not limited to, nickel, gold, copper, and aluminum.

FIG. 9 illustrates a side cutaway perspective of the invention.

Figure 10:
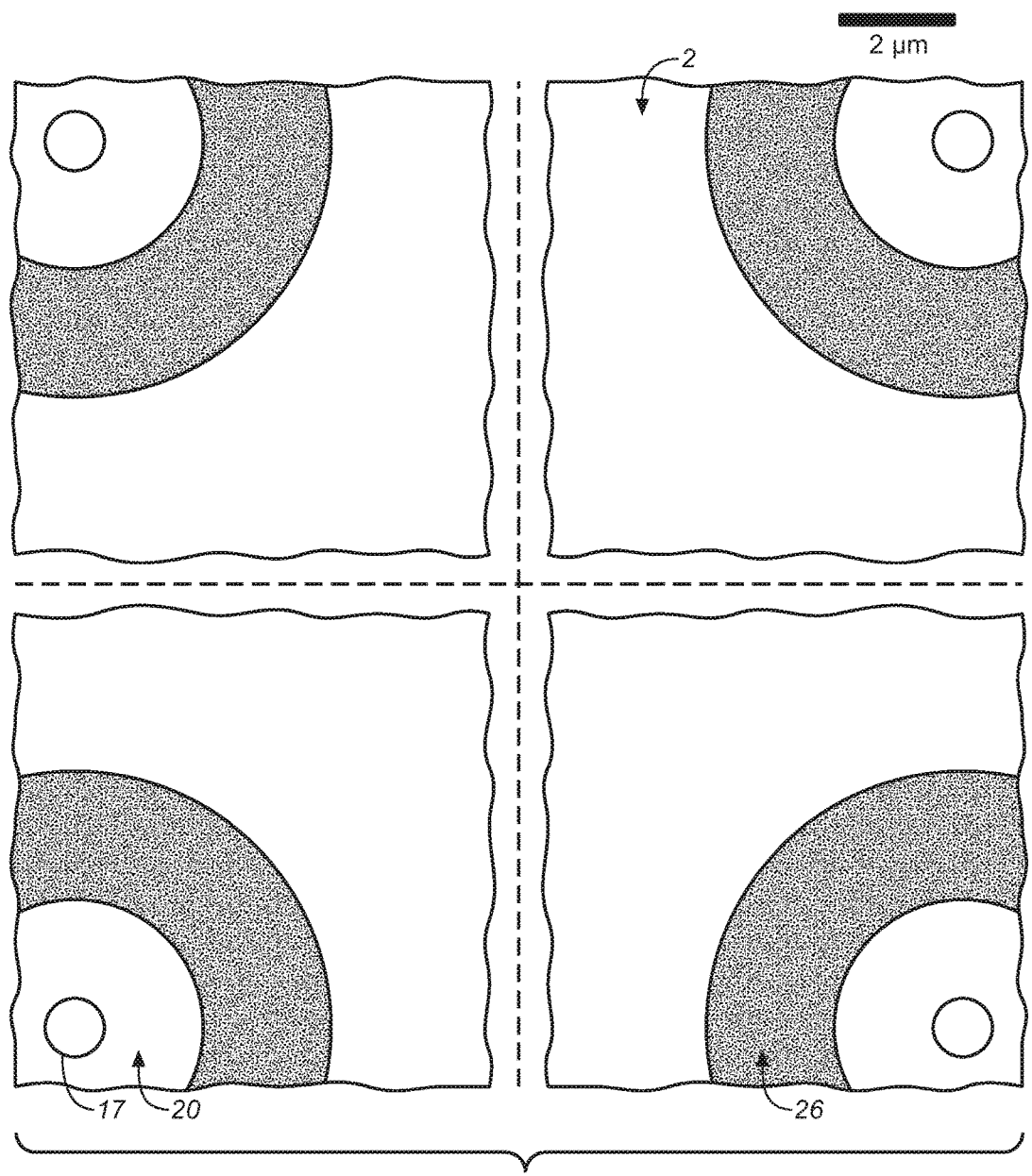
FIG. 10 illustrates an overhead perspective of the invention showing portions of four adjacent elements of the invention.

FIG. 10 illustrates an overhead perspective of the invention showing portions of four adjacent elements of the invention.

Figure 11:
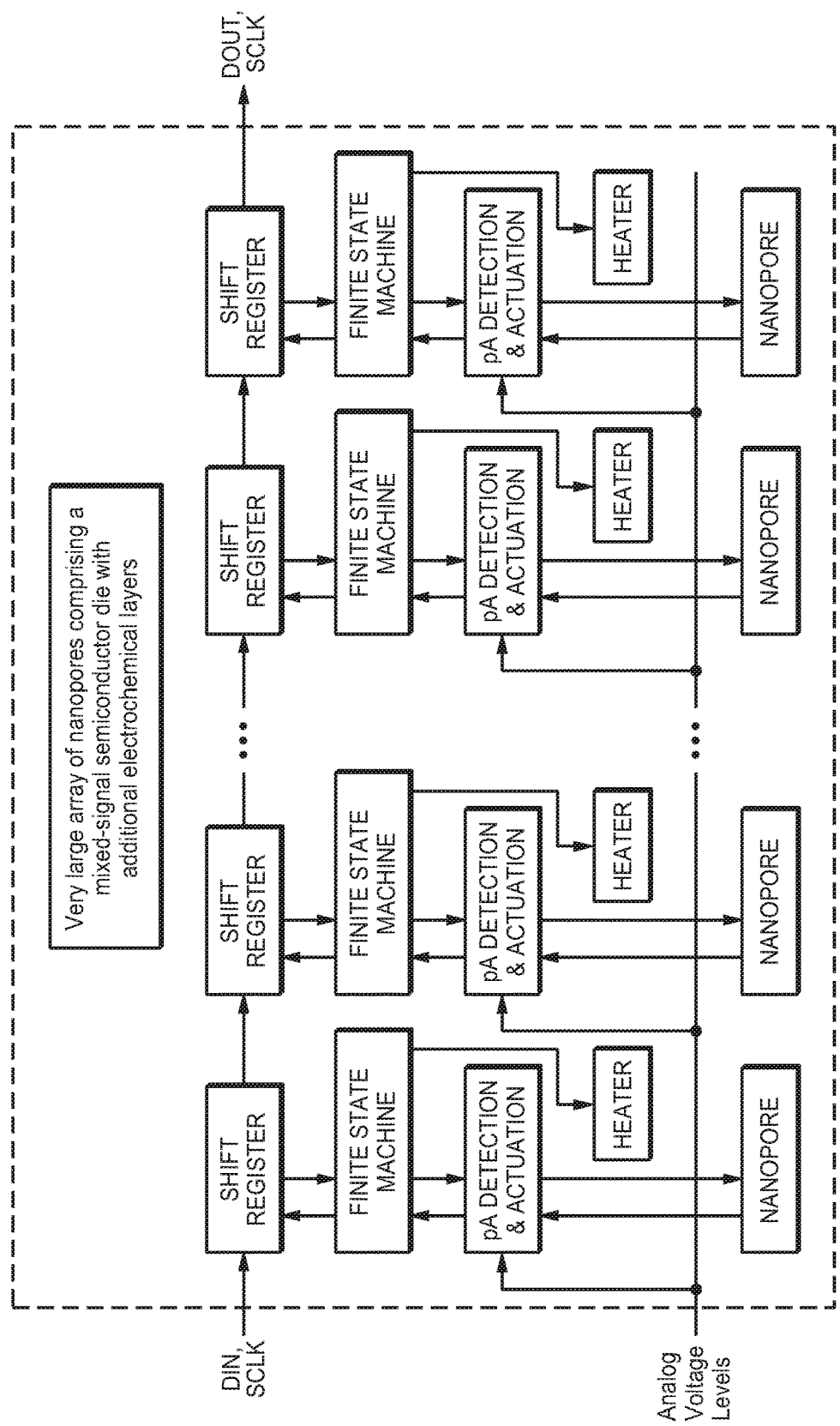
FIG. 11 illustrates a flow chart disclosing the system of one embodiment of the invention.

FIG. 11 illustrates a flow chart disclosing the method of using the invention as manufactured.

Biological nanopores have utility in sequencing of polynucleotides but, due to the low current used (approximately in the tens of picoamps), detection using high-throughput of a single nanopore sequencing device may be limited to approximately 1000 base pairs per second. Manufacturing arrays of biological nanopores that can operate independently of each other, such as used in the manufacture of very large arrays of integrated circuits, a very large scale array of nanopores may perform millions of biochemical reactions and analyses in a single second.

The array elements may be manufactured in a step-wise parallel manner, similar to the manufacture of transistors on integrated circuits. All, or most, of the similar layers of each array element are created in a sequence of single process steps that simultaneously take place on all. Or most, of the array elements.

There appears to be no simple way to synchronize the activities of separate molecules of biological reagents, so each element in the array should be able to act independently of the other elements. This may be accomplished by including a digital logic circuit with each single biological nanopore that implements a finite state machine that controls and senses the biochemical state of the complex off single (or multiple) molecules associated with the biological nanopore. The finite state machine allows low latency control of the complex of molecules associated with the biological nanopore and at the same time can store information gathered for retrieval at another time.

In order that the each of the hundreds of thousands of biological nanopore elements may be in communication with one another using a minimum number of wired connections, a serial interface and addressable logic can be used to multiplex the large amount of data entering and exiting the array (see flowchart on FIG. 11).

FIG. 9 illustrates a diagram of the manufactured array. An exemplary method of manufacture is herewith disclosed. A commercially available mixed-signal semiconductor wafer (15) comprising the analog and digital circuitry that is to be used serves as the base layer. Electrochemical layer(s) (16) may then be overlain. A metal (19), for example silver, is deposited on exposed metallization (18) to simultaneously create all or most of the electrodes for the nanopore system. As is well known to those of skill in the art, oxide (2) is growth to a thickness sufficient to encapsulate a volume equal to that of a volume of liquid that will occupy the area above the electrode. The surface of the oxide is chemically modified (16, 3) to allow wetting of the orifice and to improve lipid bilayer (thin film, 20) seal resistance. A small amount of gas (21), for example, nitrogen gas, is trapped in the areas adjacent to the electrodes that are not chemically modified. The gas is trapped because oxide that is not chemically modified repels water (or an aqueous solution). The trapped gas (21) can be used to apply suction to any one of the bilayers (20) via removal of controlled heating from the underlying electronic circuitry. The high thermal conductivity of the metallization and metal transfers the controlled heat from the electronic circuitry to the trapped gas.

The lipid layer(s), including both the monolayer (22) over the chemically modified oxide and the bilayer across the orifice (17), is applied by pressing the chemically modified wafer to a TEFLON film that has been coated on one surface with lipid. This can occur within a liquid or aqueous solution (23) present in the chamber or well (24). Removal of the overlaying TEFLON film leaves the lipid layer(s) (20, 22) overlying a first solution (23) as shown in FIGS. 9A, 9B, and 9C.

It is of note that, following the above recited method and procedure, not all of the array elements may have a thin film or bilayer across their respective orifice. The capacitance of lipid present in the orifice as measured by the finite state machine can be used to detect the presence of non-functional array elements. If it subsequently determined that a proportion of array elements lack a thin film or bilayer is greater when compared with a proportion that is preferred, then the step of overlaying the TEFLON film and lipid coat can be repeated.

Figure 9A:
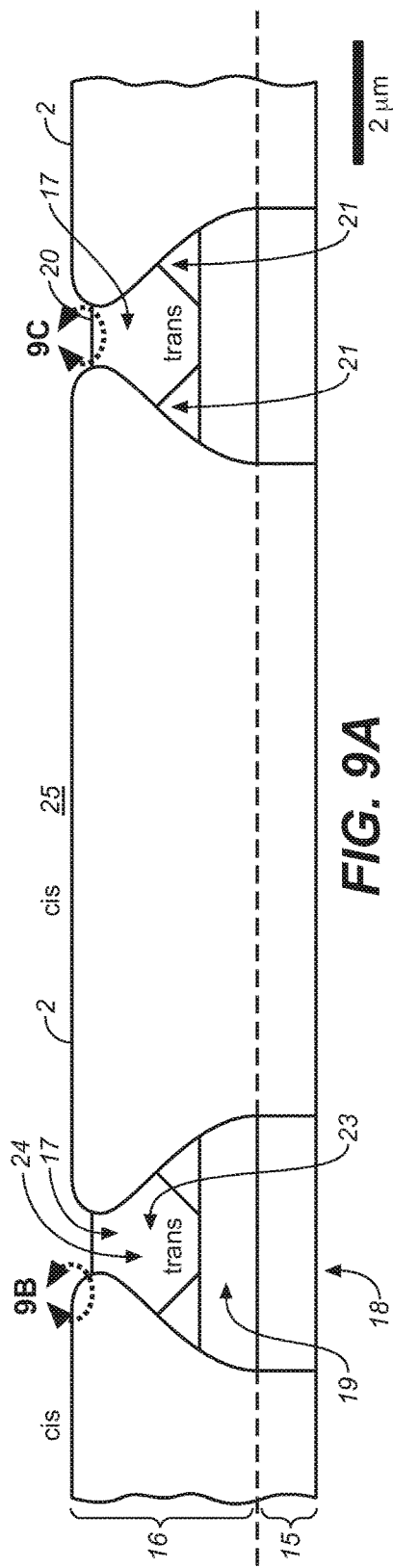
FIG. 9A-9C illustrates an exemplary embodiment of how the invention can be manufactured showing a side cutaway view of two array elements.
Figure 9B:
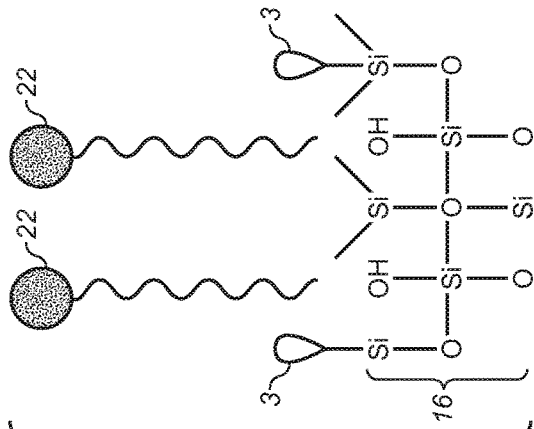
Figure 9C:
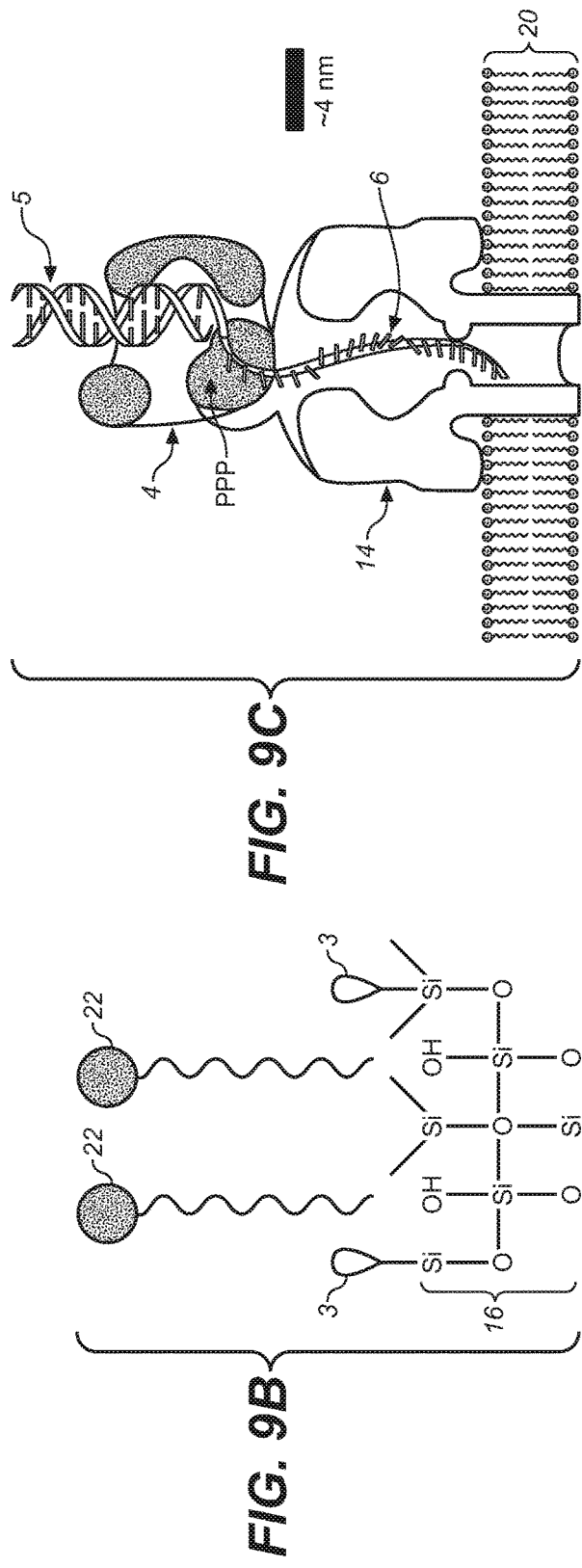

As shown in FIG. 9A, a second solution (25) that may comprise buffers that stabilizes pH for any biochemical reagents used and supporting electrolyte comprising between about 0.1M and about 5M KCl or other suitable salt. Second solution (25) covers the array elements as an unbroken drop of liquid. An electrode, for example a grounded macroscopic AgCl electrode, is placed in contact with second solution (25). When bilayers are positioned in place across all the functionable orifices, no ion current will flow from second solution (25) to first solution (23). A predetermined amount of pore molecule or channel molecule (14), such as for example, α-hemolysin toxin, is added to second solution (25). The concentration of pore molecule or channel molecule (14) is sufficient to form a single channel in any of the thin films or bilayers in approximately, for example, fifteen minutes. The time to form such channels can be for example, between one-half minute and one hour, for example, about one-half minute, one minute, two minutes, three minutes, four minutes, five minutes, seven minutes, ten minutes, fifteen minutes, twenty minutes, twenty five minutes, thirty minutes, thirty five minutes, forty minutes, forty five minutes, fifty minutes, fifty five minutes, sixty minutes, or any time therebetween. The time for formation can be altered by an operator by several factors or parameters, for example, increasing or decreasing the ambient or incubation temperature, increasing or decreasing the concentration of salt in second solution (25) or first solution (23), placing a potential difference between the first solution and the second solution that attracts the pore or channel molecule towards the thin film or bilayer, or other methods know to those of skill in the art. The finite state machine can detect and/or sense formation of a single channel in its corresponding bilayer by reacting to the flow of current (ions) through the circuit, the circuit comprising the macroscopic electrode, the second solution, the single nanopore or channel molecule, first solution, and the metal (19) electrode for any given array element.

Formation of biological channels is a stochastic process. Once a single channel has formed in a given array element bilayer, it is preferred that the chance that a second channel so forming therein is reduced or preferably, eliminated. The probability of second channel insertion can be modulated with applied potential, that is potential difference, across the bilayer. Upon sensing a single channel, the finite state machine adjusts the potential on the metal electrode to decrease the possibility of second channel insertion into the same bilayer.

Despite the precautions taken in the previous step(s) a second channel may form in a given bilayer. The finite state machine can detect the formation of the second channel. A pulse of suction from the nitrogen gas beneath the orifice may force one or more channels out from the bilayer. A heating element can be included proximal to the gas that is used to heat and thereby expand the gas under controlled conditions. A pulse of precisely controlled low pressure can force one out of two channels allowing a single channel to remain embedded in the bilayer. The finite state machine can remove one or more channels from the bilayer by inactivating the heating element and that results in contraction of the gas and applies suction to the bilayer.

In the course of using the biological nanopore for biochemical actuation and detection, the pore may become permanently obstructed. The finite state machine can detect and sense this obstructed state and can remove the blocked channel from the bilayer by inactivating the heating element thereby applying suction (reduced pressure) upon the bilayer.

In an alternative embodiment, each array element may comprise a gold electrode (26) surrounding the orifice. This gold electrode may serve to activate chemical reagents using reduction or oxidation reactions and that can act specifically at the location of a specific orifice. FIG. 10, for example, illustrates a vertical view of portions of four array elements showing the approximate spacing and placement of some of the components and elements of the invention, an orifice (17), optional gold electrode (26), and substrate or structure (2).

The finite state machine can be created using state-of-the-art commercially available 65 nm process technology, for example from Taiwan Semiconductor Manufacturing Company, Taiwan). A 600×600 array of nanopores can perform 360,000 biochemical reaction and detection/sensing steps at a rate of 1000 Hz. This may enable sequencing of polynucleotides, for example, to proceed at a rate of 360 million baser per second per 1 cm×1 cm die cut from the semiconductor wafer.

Exemplary means for applying an electric field between the cis- and trans-chambers are, for example, electrodes comprising an immersed anode and an immersed cathode, that are connected to a voltage source. Such electrodes can be made from, for example silver chloride, or any other compound having similar physical and/or chemical properties.

Detection

Time-dependent transport properties of the nanopore aperture may be measured by any suitable technique. The transport properties may be a function of the medium used to transport the polynucleotide, solutes (for example, ions) in the liquid, the polynucleotide (for example, chemical structure of the monomers), or labels on the polynucleotide. Exemplary transport properties include current, conductance, resistance, capacitance, charge, concentration, optical properties (for example, fluorescence and Raman scattering), and chemical structure. Desirably, the transport property is current.

Exemplary means for detecting the current between the cis and the trans chambers have been described in WO 00/79257, U.S. Pat. Nos. 6,746,594, 6,673,615, 6,627,067, 6,464,842, 6,362,002, 6,267,872, 6,015,714, and 5,795,782 and U.S. Publication Nos. 2004/0121525, 2003/0104428, and 2003/0104428, and can include, but are not limited to, electrodes directly associated with the channel or pore at or near the pore aperture, electrodes placed within the cis and the trans chambers, ad insulated glass micro-electrodes. The electrodes may be capable of, but not limited to, detecting ionic current differences across the two chambers or electron tunneling currents across the pore aperture or channel aperture. In another embodiment, the transport property is electron flow across the diameter of the aperture, which may be monitored by electrodes disposed adjacent to or abutting on the nanopore circumference. Such electrodes can be attached to an Axopatch 200B amplifier for amplifying a signal.

Applications and/or uses of the invention disclosed herein may include, but not be limited to the following:
1. Assay of relative or absolute gene expression levels as indicated by mRNA, rRNA, and tRNA. This includes natural, mutated, and pathogenic nucleic acids and polynucleotides.
2. Assay of allelic expressions.
3. Haplotype assays and phasing of multiple SNPs within chromosomes.
4. Assay of DNA methylation state.
5. Assay of mRNA alternate splicing and level of splice variants.
6. Assay of RNA transport.
7. Assay of protein-nucleic acid complexes in mRNA, rRNA, and DNA.
8. Assay of the presence of microbe or viral content in food and environmental samples via DNA, rRNA, or mRNA.
9. Identification of microbe or viral content in food and environmental samples via DNA, rRNA, or mRNA.
10. Identification of pathologies via DNA, rRNA, or mRNA in plants, human, microbes, and animals.
11. Assay of nucleic acids in medical diagnosis.
12. Quantitative nuclear run off assays.
13. Assay of gene rearrangements at DNA and RNA levels, including, but not limited to those found in immune responses.
14. Assay of gene transfer in microbes, viruses and mitochondria.
15. Assay of genetic evolution.
16. Forensic assays.

Filtered Derivative for Adaptive Terminal Step Detection Using a Finite-State Machine Constant voltage experiments with DNA alone and with DNA, Klenow fragment (KF) of DNA polymerase, and complementary dNTP, may be used to determine the thresholds used for detecting the terminal step, that is, dissociation of KF/dNTP from DNA. A filtered derivative of the ionic current amplitude, in addition to the filtered amplitude, may be used to detect the terminal step. In practice, the filtered amplitude is thresholded as disclosed herein, and the filtered derivative is monitored for deflections above a set threshold. Preliminary analysis using the exponentially weighted mean filter has shown that the filtered derivative, applied to the filtered amplitude, deflects by an order of magnitude in the presence of the terminal step. Experiments using both the filtered amplitude and filtered derivative are conducted, tuning the derivative filter and deflection threshold to ensure robust detection of KF dissociation.

Deflections of the derivative may be monitored for terminal step-level deflections, in principle, for any applied voltage in real time using a common (minimum) deflection threshold. In this approach, terminal step detection using only the filtered derivative, and not thresholding of the filtered amplitude is tested. Robust detection using only the filtered derivative may increase the range of voltages that can be used to probe the DNA for KF binding, without requiring identification of filtered current amplitude ranges for each probing voltage. In addition to monitoring the filtered derivative for deflections, logic that monitors the filtered amplitude for relative amplitude changes, without using preset thresholds is developed. The goal is a more adaptive ionic current filtering logic that can robustly detect KF dissociation for a broad range of (possibly varying) probing voltages, using the filtered amplitude and/or filtered derivative, without dependence on present amplitude thresholds.

Polynucleotides homologous to other polynucleotides may be identified by hybridization to each other under stringent or under highly stringent conditions. Single-stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited above.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

DNA-DNA: $T_m(° C.)=81.5+16.6(\log [Na^+])+ 0.41(\% \ G+C)-0.62(\% \ formamide)-500/L$  (I)

DNA-RNA: $T_m(° C.)=79.8+18.5(\log [Na^+])+ 0.58(\% \ G+C)+-0.12(\% \ G+C)^2-0.5(\% \ formamide)-820/L$  (II)

RNA-RNA: $T_m(° C.)=79.8+18.5(\log [Na^+])+ 0.58(\% \ G+C)+0.12(\% \ G+C)^2-0.35(\% \ formamide)-820/L$  (III)

where L is the length of the duplex formed, [$Na^+$] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between pH 6.8 to 7.4, although the rate of hybridization is nearly independent of pH at ionic strengths likely to be used in the hybridization buffer (Anderson and Young (1985) "Quantitative Filter Hybridisation." In: Hames and Higgins, editors, Nucleic Acid Hybridisation. A Practical Approach. Oxford, IRL Press, 73-111). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll, and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt (for example, NaCl) concentration, formamide concentration, hybridization temperature and probe lengths are variables that can be used to alter stringency (as described by the formula above). As a general guidelines high stringency is typically performed at $T_m$ −5° C. to $T_m$ −20° C., moderate stringency at $T_m$ −20° C. to $T_m$ −35° C. and low stringency at $T_m$ −35° C. to $T_m$ −50° C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m$ −25° C. for DNA-DNA duplex and $T_m$ −15° C. for RNA-DNA duplex. Optionally, the degree of dissociation may be assessed after each wash step to determine the need for subsequent, higher stringency wash steps.

High stringency conditions may be used to select for polynucleotide sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. polynucleotide molecules that hybridize under stringent conditions will typically hybridize to a probe based on either the entire DNA molecule or selected portions, for example, to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, for example, formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, for example, sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing the wash temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the polynucleotide sequences or their complements that encode the present transcription factors include, for example:

6×SSC at 65° C.;
50% formamide, 4×SSC at 42° C.; or
0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 min, or about 0.1×SSC, 0.1% SDS at 65° C. and washing twice for 30 min. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, for example, 50° C.

An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Even higher stringency wash conditions are obtained at 65° C. to 68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (for example, in US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a polynucleotide encoding a transcription factor known as of the filing date of the application. It may be desirable to select conditions for a particular assay such that a higher signal to noise ratio, that is, about 15× or more, is obtained. Accordingly, a subject polynucleotide will hybridize to a unique coding oligonucleotide with at least a 2× or greater signal to noise ratio as compared to hybridization of the coding oligonucleotide to a polynucleotide encoding known polypeptide. The particular signal will depend on the label used in the relevant assay, for example, a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to polynucleotides and fragments thereof under various conditions of stringency (for example, in Wahl and Berger (1987) Methods Enzymol. 152: 399-407, and Kimmel (1987) Methods Enzymol. 152: 507-511). Estimates of homology are provided by either DNA-DNA or DNA-RNA hybridization under conditions of stringency as is well understood by those skilled in the art (Hames and Higgins, Editors (1985) Nucleic Acid Hybridisation: A Practical Approach, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

Characterization and Uses of the Invention

Sequencing

In one embodiment, the invention may be used to perform sequence analysis of polynucleotides. The analyses have an advantage over the prior art and the current art in that a single analysis may be performed at a single site, thereby resulting in considerable cost savings for reagents, substrates, reporter molecules, and the like. Of additional import is the rapidity of the sequencing reaction and the signal generated, thereby resulting in an improvement over the prior art.

Other methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the HYDRA microdispenser (Robbins Scientific, Sunnyvale Calif.), MICROLAB 2200 system (Hamilton, Reno Nev.), and the DNA ENGINE thermal cycler (PTC200; MJ Research, Watertown Mass.). Machines used for sequencing include the ABI PRISM 3700, 377 or 373 DNA sequencing systems (PE Biosystems), the MEGABACE 1000 DNA sequencing system (Amersham Pharmacia Biotech), and the like. The sequences may be analyzed using a variety of algorithms that are well known in the art and described in Ausubel et al. (1997; Short Protocols in Molecular Biology, John Wiley & Sons, New York N.Y., unit 7.7) and Meyers (1995; Molecular Biology and Biotechnology, Wiley VCH, New York N.Y., pp. 856-853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative regions flanking the polynucleotide molecules of interest. Incomplete assembled sequences are inspected for identity using various algorithms or programs such as CONSED (Gordon (1998) Genome Res. 8: 195-202) that are well known in the art. Contaminating sequences including vector or chimeric sequences or deleted sequences can be removed or restored, respectively, organizing the incomplete assembled sequences into finished sequences.

Extension of a Polynucleotide Sequence

The sequences of the invention may be extended using various PCR-based methods known in the art. For example, the XL-PCR kit (PE Biosystems), nested primers, and commercially available cDNA or genomic DNA libraries may be used to extend the polynucleotide sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55° C. to about 68° C. When extending a sequence to recover regulatory elements, it is preferable to use genomic, rather than cDNA libraries.

Use of Polynucleotides with the Invention

Hybridization

Polynucleotides and fragments thereof can be used in hybridization technologies for various purposes. A probe may be designed or derived from unique regions such as the 5' regulatory region or from a conserved motif such as a receptor signature and used in protocols to identify naturally occurring molecules encoding the polynucleotide protein, allelic variants, or related molecules. The probe may be DNA or RNA, is usually single stranded and should have at least 50% sequence identity to any of the polynucleotide sequences. Hybridization probes may be produced using oligolabeling, nick translation, end-labeling, or PCR amplification in the presence of labeled nucleotide. A vector containing the polynucleotide or a fragment thereof may be used to produce an mRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between polynucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the polynucleotides are completely complementary. In some membrane-based hybridizations, preferably 35%, or most preferably 50%, formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra) and Sambrook et al. ((1989) Molecular Cloning. A Laboratory Manual, Cold Spring Harbor Press, Plainview N.Y.).

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, for example, Brennan et al. (1995) U.S. Pat. No. 5,474,796; Schena et al. (1996) Proc. Natl. Acad. Sci. 93:10614-10619; Baldeschweiler et al. (1995) PCT application WO95/251116; Shalon et al. (1995) PCT application WO95/35505; Heller et al. (1997) Proc. Natl. Acad. Sci. 94:2150-2155; and Heller et al. (1997) U.S. Pat. No. 5,605,662.)

Hybridization probes are also useful in mapping the naturally occurring genomic sequence. The probes may be hybridized to: (a) a particular chromosome, (b) a specific region of a chromosome, or (c) artificial chromosome construction such as human artificial chromosome (HAC), yeast artificial chromosome (YAC), bacterial artificial chromosome (BAC), bacterial P1 construction, or single chromosome cDNA libraries.

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP or amino acid such as $^{35}$S-methionine. Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Feedback Control of Single Tethered Polymers to Repeatedly Probe Polymer-Binding Macromolecules This section explains the basic mechanisms of Klenow Fragment (KF) polymerase and how dissociation of KF from its DNA template can be detected by monitoring the pore current amplitude and event dwell times. Furthermore, the identity of the next base to be added by KF can be found through the presence of long dwell time events (such as, for example, but not limited to >20 msec). The long dwell time events can then be detected and reacted to using dynamic voltage control using a finite state machine (FSM).

It has been shown that KF bound to a DNA hairpin captured in a nanopore can be differentiated from DNA hairpin alone based on current amplitude. Also, the identity the next base to be added the to a DNA hairpin can be identified based on event dwell time. The ability to detect and react to different DNA/enzyme configurations and identify the base being catalyzed by KF is a strong motivator for the control of enzyme function and development of a nanopore-based sequencing method, though further detection and control precision is necessary.

The automated detection and control of single DNA hairpin molecules using the nanopore system is now described. Precise control of single DNA molecules is necessary to make multiple sequential base identifications as would be employed in nanopore-based sequencing. DNA hairpin events are detected and it is shown that their dwell time can be regulated. The results presented demonstrate the level of control necessary for regulation of repeated enzyme binding events with a single piece of DNA captured in a nanopore.

It has been shown that individual DNA hairpins can be detected and controlled based on the amplitude of the nanopore current signal. The DNA hairpin's dwell time can be extended by reducing the applied voltage upon detection of a hairpin in the pore. Longer dwell times provide more signal that can be used to identify the terminal base pair of the hairpin using machine learning methods (See for example, Vercoutere, et al. (2001) Nat. Biotechnol, 19(3): 248-252; and Akeson (2003) Nucleic acids research, 31: 1311-1318). An extension of the control demonstrated here allows for the use of a single DNA hairpin to capture multiple enzymes, as shown in the next chapter.

In Examples XX through XXX, the repeated capture of enzymes with a single DNA hairpin is demonstrated. Multiple enzyme experiments can be performed rapidly, offering higher throughput compared to atomic force spectroscopy (AFM) and optical tweezer methods, which require manual attachment to the molecules to be measured (See Elio et al. (2005) Nature, 438(7067): 460-465; and Greenleaf and Block (2006) Science, 313(5788): 801). The ability to rapidly probe DNA/enzyme interactions provides further motivation for nanopore-based sequencing.

Basic detection and control of a single DNA hairpin for repeated capture of KF has been demonstrated. Real time detection of enzyme dissociation can be made by recognizing the terminal step present in the nanopore current signal of binary and ternary complex translocation events. Repeatedly probing an enzyme using a single piece of DNA achieves the mechanical action necessary for quick reading of long sequences of DNA using a nanopore. More work needs to be done to regulate single base additions by KF, which is also necessary for sequencing using a nanopore. The terminal step detection methods presented here offer satisfactory results, but fewer false detects are necessary for sequencing using enzyme fishing to be practical.

Improvements to the enzyme fishing mechanism have been proposed. The exponentially weighted moving average filter replace the moving average filter used previously to reduce computational complexity and improve signal smoothing. An enzyme dissociation check that can confirm fishing is performed with a bare DNA hairpin to ensure each detected enzyme event is a new enzyme binding event. This is important for use of statistical models for sequencing because models assume new enzyme binding events. Higher signal-to-noise can be achieved through use of a longer DNA hairpins that would allow the use of higher control voltages. Reliable detection and reaction to DNA/enzyme unbinding will allow for accurate base identification from repeated enzyme event data.

Diagnostics

The polynucleotides, fragments, oligonucleotides, complementary RNA and DNA molecules, and PNAs may be used to detect and quantify altered gene expression, absence/presence versus excess, expression of mRNAs or to monitor mRNA levels during therapeutic intervention. Conditions, diseases or disorders associated with altered expression include idiopathic pulmonary arterial hypertension, secondary pulmonary hypertension, a cell proliferative disorder, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis; acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, hemodialysis, extracorporeal circulation, viral, bacterial, fungal, parasitic, protozoal, and helminthic infection; a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, benign prostatic hyperplasia, prostatitis, Peyronie's disease, impotence, gynecomastia; actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, complications of cancer, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In another aspect, the polynucleotide of the invention.

The polynucleotides, fragments, oligonucleotides, complementary RNA and DNA molecules, and PNAs, or fragments thereof, may be used to detect and quantify altered gene expression; absence, presence, or excess expression of mRNAs; or to monitor mRNA levels during therapeutic intervention. Disorders associated with altered expression include akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain. These cDNAs can also be utilized as markers of treatment efficacy against the diseases noted above and other brain disorders, conditions, and diseases over a period ranging from several days to months. The diagnostic assay may use hybridization or amplification technology to compare gene expression in a biological sample from a patient to standard samples in order to detect altered gene expression. Qualitative or quantitative methods for this comparison are well known in the art.

The diagnostic assay may use hybridization or amplification technology to compare gene expression in a biological sample from a patient to standard samples in order to detect altered gene expression. Qualitative or quantitative methods for this comparison are well known in the art.

For example, the polynucleotide or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate the level that is observed in a normal subject. The results obtained from successive assays may be used to show the efficacy of treatment over a period ranging from several days to months.

Purification of Ligand

The polynucleotide or a fragment thereof may be used to purify a ligand from a sample. A method for using a polynucleotide or a fragment thereof to purify a ligand would involve combining the polynucleotide or a fragment thereof with a sample under conditions to allow specific binding, detecting specific binding, recovering the bound protein, and using an appropriate agent to separate the polynucleotide from the purified ligand.

In additional embodiments, the polynucleotides may be used in any molecular biology techniques that have yet to be developed, provided the new techniques rely on properties of polynucleotides that are currently known, including, but not limited to, such properties as the triplet genetic code and specific base pair interactions.

REFERENCE NUMERALS

1. Pore or pore aperture
2. Substrate or structure
3. Compound
4. Macromolecule
5. First polymer
6. Incompletely synthesized portion of polymer
7. Monomer
8. Substantially completely synthesized polymer
9. High affinity binding site
10. Ligand
11. Product 12. Second polymer
13. Third monomer
14. Pore molecule or channel molecule
15. Mixed-signal wafer
16. Electrochemical layer
17. Orifice
18. Metallization composition
19. Metal
20. Thin film or lipid bilayer
21. Trapped gas (for example, nitrogen)
22. Lipid monolayer
23. Liquid or aqueous solution (first)
24. Chamber or well
25. Liquid or aqueous solution (second)
26. Gold electrode (optional)

To our knowledge, we are the first researchers to use an FPGA to control and measure complexes in a nanopore. (See Hornblower et al. (2007) Nature Meth. 4: 315-317.) We believe that similar functionality could be achieved with an appropriate microprocessor. FSM logic has been used as part of a machine learning approach used to identify the terminal base pair of the blunt end of DNA hairpins (see Vercoutere, et al. (2001) Nat. Biotechnol, 19(3): 248-252; Winters-Hilt et al. (2003) Biophys. J., 84(2): 967-976). This is a much different application of an FSM in which its primary role was for training the machine learning models offline; our FSM functionality is used for online voltage control.

Direct control of ssDNA in a nanopore (no enzymes) has been demonstrated (Bates et al (2003) Biophysical Journal, 84: 2366-2372) in which detection of DNA is based on monitoring the raw amplitude relative to a threshold level. Voltage level changes, comparable to those employed in Wilson et al. ((2008) ibid), were commanded to explore the zero and low voltage effects on ssDNA-pore interactions. In contrast to thresholding the raw ionic current amplitude, our approach filters the current in real time (details given in the Examples).

Alternative methods for single-molecule sensing and manipulation include optical tweezers and atomic force microscopy (see Bustamante et al. (2003) Nature, 421: 423-427). For example, optical trapping has been used to sequence DNA by attaching a processive enzyme to a polystyrene bead (see Abbondanzieri et al (2005) Nature, 438(24):460-465; and Greenleaf and Block (2006) Science, 313:801). At present, greater spatial and temporal resolution of single DNA molecule polymerization has been achieved than with nanopores. However, these methods generally require more preparative steps, and far fewer molecules can be analyzed over a common time period.

Our invention uses feedback control of a single tethered DNA molecule suspended in a nanopore for repeated capture and subsequent dissociation of individual DNA-binding enzymes. There are two phases to our implementation.

First, a single DNA molecule with single and double stranded segments is captured, by the single-stranded end, and then tethered, by making the single-stranded segment double-stranded on the trans side. In this configuration, with double-stranded segments on both cis and trans sides of the channel, the DNA will remain in the channel until a sufficient voltage force unzips the double-stranded segments from the cis or trans side. The length of the single-stranded segment in the channel is chosen such that, under negative voltages, exposure of the single-to-double stranded (ss-ds) junction in the cis chamber is sufficiently available for KF binding.

In the second phase, the tethered DNA is used for repeated capture and dissociation of KF enzymes in the cis chamber of the nanopore. By analogy with fishing, the DNA is the line and bait (with the ss-ds junction as the hook), and the enzymes are the fish (which can be caught only one at a time). Details are now given on our setup, control logic, related approaches in the literature, and our initial demonstration of repeated KF binding to a tethered DNA molecule in a nanopore.

Impact and Refinement of Tethered DNA Capability

For the purpose of exploring the interaction of enzymes that bind or modify DNA or RNA (exonucleases, kinases, and other polymerases), with DNA or RNA captured in a nanopore, we consider that the invention disclosed herein will have the following technological impacts:

Substantial increase in data throughput. In the tethered configuration, a negative voltage is used in fishing mode, and a positive voltage is used for probing mode. In probing mode, all information contained in the ionic current can be used for characterization of the polymer alone or polymer-enzyme interactions, at any desired probing voltage. In non-tethered configuration, independent events (including capture, blockage of nanopore, and eventual translocation of polymer) contain the information relevant for analysis of polymer alone or polymer-enzyme interactions. A sufficient voltage is required for capture of each molecule, the time between events is not controllable, and lower capture voltages increase the time between events. Thus, the tethered configuration increases the throughput of analyzable data, by increasing the number of analyzable events over a common period and by increasing the range of probing voltages.

Reduction in non-analyzable data. In probing mode, the ionic current contains information about the tethered polymer alone or the interaction of an enzyme bound to the tethered polymer. In non-tethered configuration, up to 50% of events recorded within an experiment can be unrelated to the kinetics of interest. For example, brief blockades caused by the ds-end of a DNA hairpin contacting the cis-side of the pore would be included in data in the non-tethered configuration, but not in the tethered configuration.

Substantial increase in sensitivity of nanopore sensor for real-time detection of the addition of biological components in cis chamber. Post-experiment analysis demonstrates the sensitivity of nanopore sensors for detection of the presence of $Mg^{2+}$ cofactor and complementary dNTP of KF. In both cases, detection is based on the increase in dwell time for the KF-bound portion of binary/ternary events. By monitoring the dwell time of KF-bound portions of events in real time, the tethered configuration offers a new capability for online detection of addition of $Mg^{2+}$ and complementary dNTP components to the cis-chamber. The same capability can be utilized with other enzymes and their corresponding event-sensitive components. In our future tethered DNA experiments with KF, real-time detection capabilities will be explored as a function of fishing time, dNTP concentration, $Mg^{2+}$ concentration, and probing voltage.

The invention will be more readily understood by reference to the following examples, which are included merely for purposes of illustration of certain aspects and embodiments of the present invention and not as limitations.

EXAMPLES

Herein are described several examples to demonstrate the capability of measuring macromolecules and polanions or polycations.

Example I

Enzyme Binding is Prevented by a Blocking Primer

For an illustration of this method, see FIGS. 1(a) through 1(g). (a) In this scenario, the blocking primer is bound to the primer/template in bulk phase. Structure of the ternary complex prevents binding of the enzyme to the junction between the dsDNA and ssDNA segments of the target DNA where the first nucleotide would be incorporated. (b) Capture of a blocked primer/template under an applied voltage (trans side positive) threads the ssDNA into the pore and perches the dsDNA above the vestibule. This occurs because the loop at the end of the blocking primer is too large to enter the vestibule. The current reports capture of the complex in this state. (c) Under the applied voltage, the ssDNA segment advances in the pore toward the trans-side and processively unzips base-pairs between the blocking primer and the template. The energy cost of releasing each base pair independently is small (about 2.5 kcal/mol), so it proceeds rapidly under force. During this unzipping process the current is the same as in (b) because the dsDNA segment cannot enter the vestibule. (d) Release of the blocking primer following unzipping. Absent the blocking primer, the dsDNA segment of the target DNA can enter the pore vestibule. This results in a measurable reduction in current that signals release of the blocking primer and activation of the target DNA. (e) Voltage reversal exposes the activated dsDNA/ssDNA junction for enzyme binding. By reversing voltage, the negatively charged DNA is driven back into the cis compartment. (f) Absent the blocking primer, enzymes can bind to the DNA at the targeted position (the dsDNA/ssDNA junction in this example). (g) Probing for bound enzyme or DNA modification. Following a defined amount of time (typically hundreds of microseconds to seconds), the voltage can be reversed once again to its original polarity, thus pulling the DNA back into the nanopore. Current readout can be used to determine if an enzyme has been bound (shown) or if the DNA duplex terminus has been modified (not shown). If the result is negative, steps (e)-(g) can be repeated.

Example II

Enzyme Catalysis is Prevented by a Blocking Primer

For an illustration of this method, see FIGS. 2(a) through 2(g). (a) In this scenario, the blocking primer is bound to the primer/template in bulk phase. Structure of the ternary complex permits binding of the enzyme to the target DNA but catalysis and processing along the template are prevented. (b) Capture of a blocked primer/template under an applied voltage (trans-side positive) threads the ssDNA into the pore and perches the dsDNA above the vestibule. This occurs because the loop at the end of the blocking primer is too large to enter the vestibule. The current reports capture of the complex in this state. (c) Under the applied voltage, the ssDNA segment advances in the pore toward the trans-side and processively unzips base-pairs between the blocking primer and the template. The energy cost of releasing each base pair independently is small (about 2.5 kcal/mol), so it proceeds rapidly under force. During this unzipping process the current is the same as in (b) because the dsDNA segment cannot enter the vestibule. (d) Release of the blocking primer following unzipping results in activation of the complex. Unlike the scenario disclosed in FIG. 1, the dsDNA segment of the target DNA cannot enter the pore vestibule when the block dissociates because the bound enzyme is too large to enter. Thus the average current does not change. (e) Reducing the applied voltage permits the enzyme to proceed. There remains sufficient ionic current for analysis. (f) The template strand is copied to completion. (g) The complex dissociates and the nanopore is now ready to capture and activate another DNA target (see step a).

Example III

Enzyme Catalysis is Activated by Injection of $Mg^{2+}$ Across a Nanopore

For an illustration of this method, see FIGS. 3(a) through 3(c). (a) In this example scenario, the cis compartment contains all components necessary for DNA polymerase activity except for $Mg^{2+}$. Thus, no catalysis can take place. (b) When voltage is applied (trans-side+), $Mg^{2+}$ is driven across the pore into the cis compartment. (c) When a DNA-polymerase complex is captured by the pore, the $Mg^{2+}$ concentration in the volume immediately adjacent to the pore is sufficiently high to permit $Mg^{2+}$ occupation of the two critical loci in the enzyme's catalytic site. Polymerization of the copied strand can then occur. Ternary complexes in the bulk phase cannot catalyze DNA synthesis because the $Mg^{2+}$ concentration distal from the pore is essentially zero. This scenario could be applied to other substances that are required for DNA synthesis and that are small enough to permeate the nanopore under controlled conditions.

Example IV

Measuring Polymerase Activity Using a Biological Nanopore, α-Hemolysin

The polymerase activity of DNA polymerase I is largely contained in a smaller structure called the Klenow fragment. In this application, the Klenow fragment is allowed to bind to a strand of DNA (the template) that has undergone complementary base pairing with a primer of defined base sequence. The protein is drawn to the pore and the ionic current through the pore is thereby reduced. Two different enzymatic functions can be monitored. 1) When the protein is released from its binding site on the primer-template complex, a characteristic transient reduction of ionic current is produced. 2) When the enzyme is supplied by the appropriate dNTP substrate, a characteristic lengthening of the residence time of the enzyme in the pore is produced. Incorrect dNTP substrates do not alter the residence time.

Example V

Detecting Ligand Binding to a Receptor Protein

The cytoplasmic estradiol receptor is covalently linked to a 100 mer of polyaspartic acid by formation of an appropriate covalent bond, such as that produced by a cross-linking agent. The receptor is positioned at a 3 nm diameter silicon nitride pore by the electric field acting on the polyaspartic acid in its anionic form. The pore has a monolayer of a bifunctional alkyl sulfide attached to a gold layer on the pore. After positioning, the receptor is covalently bonded to the pore by formation of disulfide bonds between the alkyl groups on the pore and cysteine groups on the receptor. When estradiol is present, it binds to the high affinity site on the receptor and alters ionic current though the pore, thereby providing a means of detecting this steroid hormone with single-molecule sensitivity.

Example VI

Detecting Glucose Oxidase Activity

Following the procedure outlined in Example 2, a glucose oxidase molecule is attached to a silicon nitride pore. When glucose is present, the enzymatic action produces detectable transient changes in the ionic current through the pore as the glucose binds to the active site, oxidation, and release of products.

Example VII

Monitoring Ribosome Function

A ribosome preparation is exposed to a specific mRNA in the presence of a commonly used translation system such as cytosolic extract of E. coli. The system is maintained near 0° C. in order to inhibit ribosome function. Alternatively ribosomes may be inactivated by excluding a required cofactor such as an elongation factor or tRNAs. When a single ribosome attaches to the mRNA, it can be positioned at the pore by drawing the mRNA through the pore by the action of a transmembrane voltage of 100 mV or more. The mixture is then rapidly warmed to 25° C. to initiate protein synthesis or addition of a required cofactor. The individual steps of protein synthesis are then monitored by the combined effects on ionic current that are produced by mRNA being drawn through the pore by the ribosome action, and cyclic conformational changes of the ribosome as it proceeds through the steps of translation.

Example VIII

Positioning an α-hemolysin Channel in a Solid State Pore

Alpha hemolysin channels in the form of heptamers are assembled in liposome membranes. After assembly is complete, DNA 100mers having a streptavidin molecule at one end are added and a transient membrane potential is produced across the liposome membrane, positive inside. One way to do this is to add a salt having a cation that can permeate the hemolysin channel and an anion that is impermeable due to its size. The membrane potential draws the free end of the hairpin into the pore. Because of the streptavidin structure, the DNA cannot pass through the pore, but instead forms a complex with the hemolysin. The heptamer with its attached DNA strand is then isolated by published procedures, and added to the cis side of a silicon nitride membrane with a 5 nm pore. A voltage of 100 mV or more is applied, and electrophoresis draws the DNA strand protruding from the stem of the hemolysin heptamer into the pore. The hemolysin heptamer is then covalently attached to the pore as described in the Examples. The guiding DNA strand is then removed by reversing the polarity of the applied potential, and the hemolysin-silicon nitride membrane can then be used as a high resolution nanopore for biosensor applications.

Example IX

Figure 12:
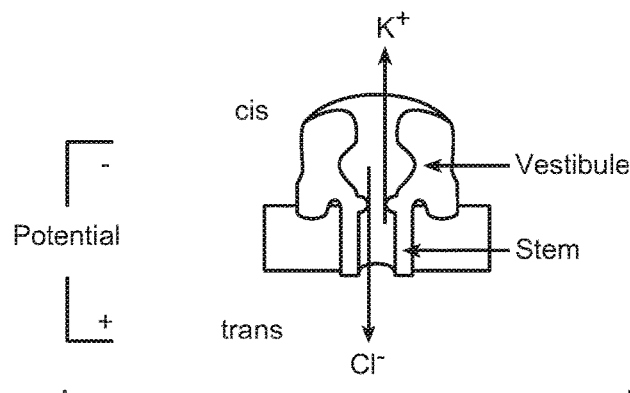
FIG. 12 illustrates a single α-hemolysin protein channel (mushroom shape) inserted into lipid bilayer. Under applied potential (trans-side positive), $K^+$ ions flow to the cis side, and Cl ions flow to the trans side. The vestibule and stem of the pore channel are shown.
Figure 13:
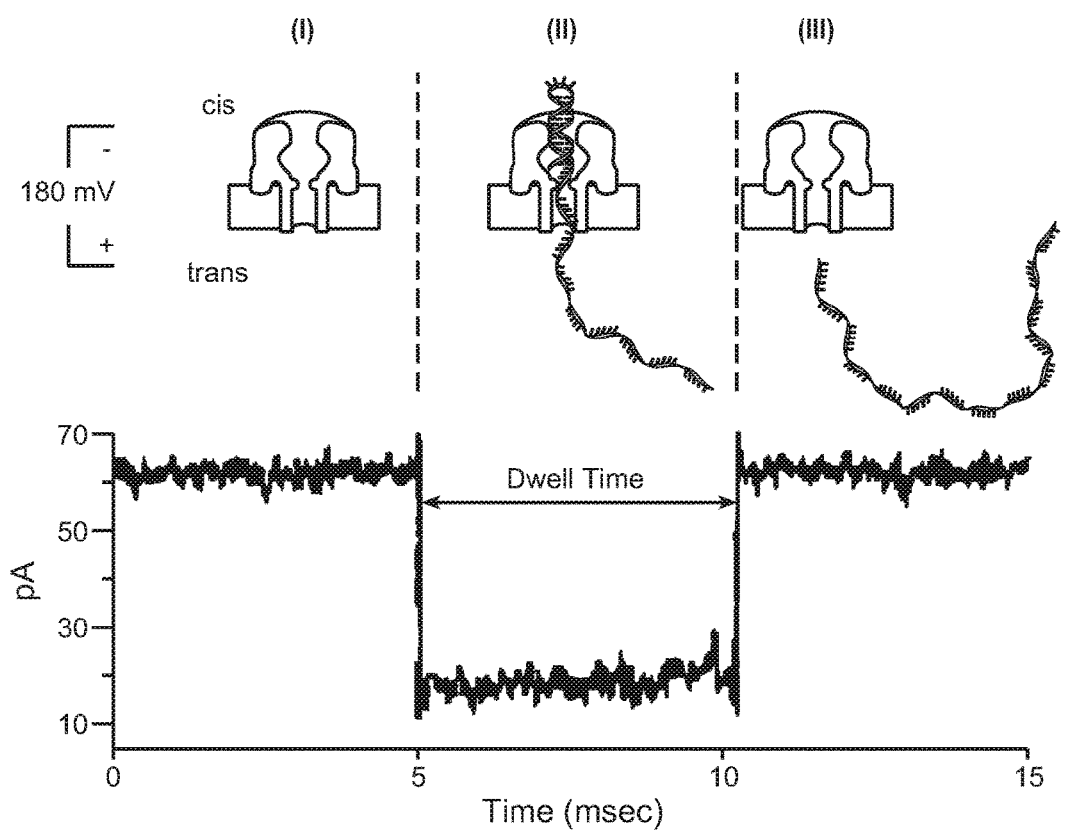
FIG. 13 illustrates a schematic of nanopore and DNA (top), and plot of representative ionic current signal (bottom) during a 20 base pair hairpin DNA translocation event under 180 mV applied potential. (I) At 180 mV, KCl ions pass through the open channel resulting in ~64 pA current. (II) Upon capture of the single-stranded end of the DNA molecule into the cis opening of the pore, the flow of ions is reduced to ~20 pA. (III) After ~5 msec, the voltage unzips the hairpin, causing ssDNA to pass through the pore into the trans chamber, completing the measured blockaded event. The duration of the event is referred to as dwell time.

Feedback Control of a Single Tethered DNA Molecule Suspended in a Nanopore to Repeatedly Probe DNA-binding Enzymes In the biological nanopore setup, a planar lipid bilayer is created across a 50-100 μm teflon aperture in a KCl solution, and a single α-hemolysin protein channel self-inserts into the planar lipid. The channel (pore) is 15 nm in length and varies in diameter. The cis-opening of the pore is 2.6 nm wide, opening to a 3.6 nm vestibule before narrowing to a limiting 1.5 nm width at the beginning of the stem. The remainder of the stem up to the trans-opening is 2 nm wide. The vestibule is large enough for double-stranded DNA (dsDNA) to enter, but the limiting stem is just wide enough for single-stranded DNA (ssDNA) to pass through. AgCl electrodes are used to apply a potential across the bilayer that produces an ionic current through the pore (FIG. 12). The field created by this voltage pulls the negatively charged phosphate backbone of the ssDNA or RNA through the pore, passing from the cis side to the trans side of the pore with the trans-side voltage positive. As molecules translocate, the pore becomes partially blocked by the translocating molecule, causing a drop in current. These translocation events can be characterized by the amplitude of the attenuated (blockade) current and the time the molecule spends in the pore, defined as the dwell time. A schematic of the nanopore system and an example DNA translocation event is shown in FIG. 13. The DNA shown in FIG. 13 has single and double-stranded segments, with the double-stranded segment as a 20 base pair hairpin (20 bphp). The DNA is captured by the single-stranded end into the nanopore, and translocates once the voltage field force causes the hairpin to unzip within the vestibule. This configuration has utility towards a part of the instant invention. The utility of the double-stranded segment is that it extends the dwell time (by stopping translocation) of the DNA, briefly, until the voltage shears the segment into single stranded DNA and the DNA translocates. Additionally, longer double-stranded segments yield longer dwell times at a given voltage. In contrast, for ssDNA or RNA, translocation rates reach up to 2 nucleotides/μsec with no pauses in translocation under capture-level voltages.

We note that the double-stranded segment may alternatively be formed by annealing a primer DNA segment, with the complementary bases, to the end of single-stranded DNA. The key is that, in our configuration, the captured DNA molecule must have single and double-stranded segments. This structure facilitates capture and retention: the single-stranded end is captured, and the double-stranded end increases the dwell time, providing time to detect capture and react by reducing the voltage to a hold level (explained in more detail below). Another key reason for using this DNA structure is that the enzyme exploited in our proposed approach binds to the DNA precisely at the single-to-double stranded junction of the DNA.

Example X

Nanopores and Enzymes

Recently, we have used biological nanopores to probe the interaction of enzyme with a captured DNA molecule. Under an applied voltage, the ssDNA end of enzyme-bound DNA is captured in the nanopore, with the enzyme residing on top of the nanopore being too large to translocate through it. Kinetics of *Escherichia coli* exonuclease I (ExoI) binding to ssDNA has been quantified using voltage ramps for nanopore-based force spectroscopy. Specifically, upon detection of capture of ssDNA, voltage is automated to briefly hold the ssDNA-ExoI complex, then implement a voltage ramp until ExoI dissociates and the ssDNA translocates through the pore. The time-to-dissociation under the applied voltage ramp is in turn used to estimate binding rate constants.

Figure 14A:
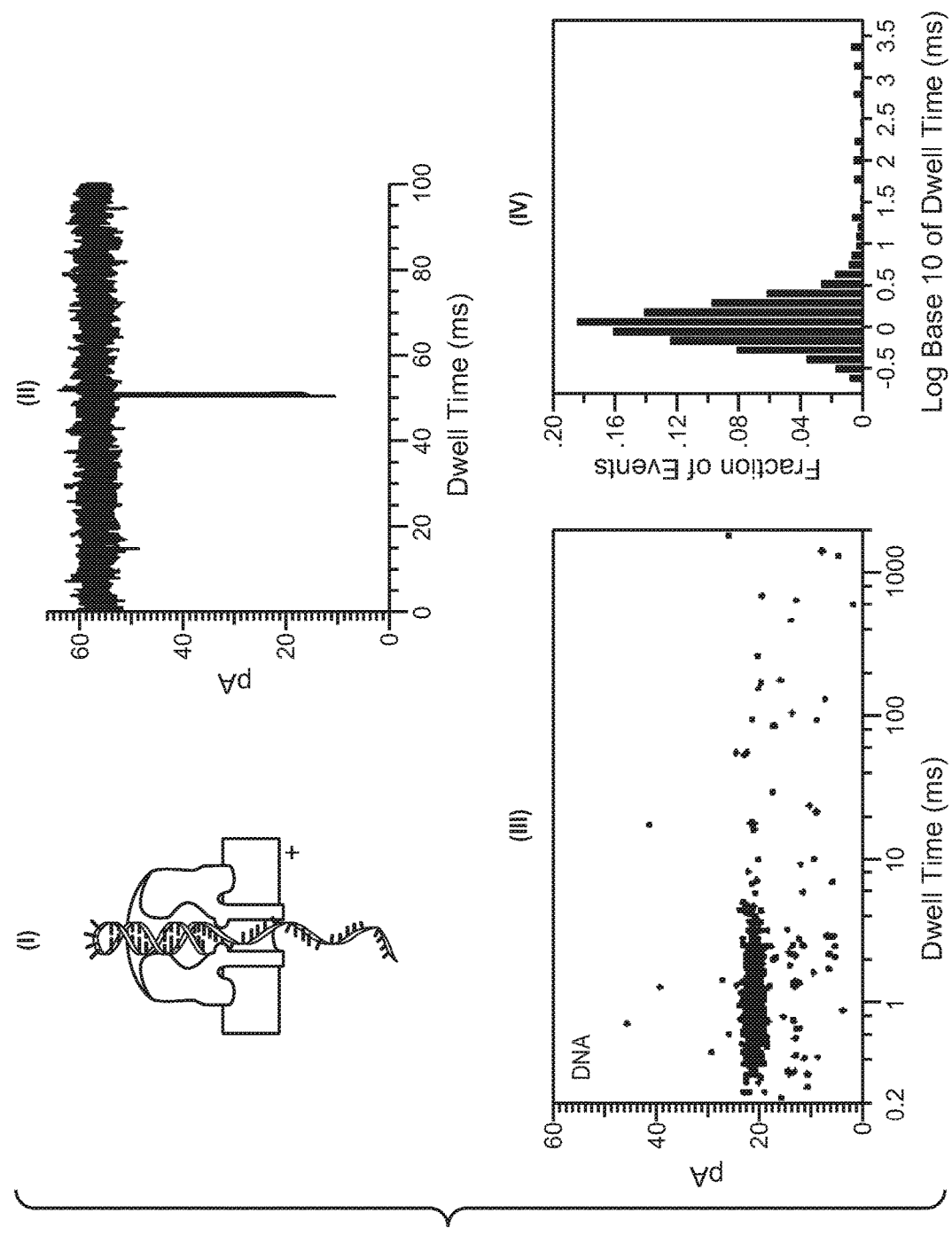
FIG. 14A-14C illustrates Distinguishing DNA, DNA/KF complexes, or DNA/KF/dNTP complexes in the nanopore device.

Previously (see Benner, et al. (2007) Nature Nanotechnology, 2: 718-724) we have explored the interaction of DNA with the Klenow fragment (KF) of *Escherichia coli* DNA polymerase I. In the absence of KF, capture and subsequent unzipping of 14 bphp at constant 180 mV reveals blockades with 20 pA mean amplitude and 1 msec median dwell time (FIG. 14A). Addition of 2 µM KF yielded a new population of events attributable to binary complexes (DNA/KF) with higher mean amplitude (23 pA), and resulted in an event plot (FIG. 14B(II)) with a longer dwell time (3 msec median of all events). Addition of 200 µM deoxyguanosine triphosphate (dGTP), the dNTP complementary to the DNA template base in the KF catalytic site, extended the dwell time of the new population to 133 msec median, attributable to a higher stability bond within ternary complexes (DNA/KF/dGTP).

Our tethered DNA configuration described in the next section leverages a significant structural feature exhibited by KF-bound DNA events (with or without the complementary dNTP, that is, binary or ternary complexes), now described. Closer investigation of the binary and ternary complex blockades revealed a two-step pattern in greater than 90% and 97% of the blockades, respectively. The first step has a 23 pA mean amplitude, followed by a brief (1 msec median dwell time) second step, referred to as the terminal step at 20 pA mean amplitude. It was demonstrated that the transition from step one to step two resulted in dissociation of KF (for binary and ternary complexes) from DNA, followed by hairpin dropping into the pore vestibule until translocation occurred. Thus, the terminal step kinetics are precisely the DNA duplex unzipping kinetics.

The consistent presence of the terminal step within enzyme-bound DNA events is mechanistically of importance to our invention. In particular, for an enzyme-bound DNA complex captured in the nanopore under a constant voltage, the terminal step makes it possible to detect in real-time that enzyme has dissociated from the DNA, on the basis of the change in amplitude (from 23 pA to 20 pA at 180 mV in our recent work with KF).

Example XI

Detection and Control of DNA and KF-bound DNA in a Nanopore

In this approach, the voltage control logic is programmed using a finite state machine (FSM) within the LabVIEW 8 software, and the FSM logic is implemented on a field-programmable gate array (FPGA) hardware system. Our first implementation of FSM/FPGA voltage control demonstrated efficient automated detection of individual ternary complexes, based on the characteristic 23 pA amplitude and a dwell time of at least 20 msec. For all events that remained within the threshold range of 21.2-26.8 pA for 20 ms, the voltage was reversed to expel the complex back into the cis chamber, rather than waiting (>100 msec median dwell time) for dissociation of enzyme and DNA translocation to the trans side. The control logic had the effect of concentrating the dwell time of the detected ternary complex events, from a median dwell time of 123 msec (235 msec interquartile range (IQR)) without FSM/FPGA control, to a median dwell time of 23 msec (0.3 msec IQR) with FSM/FPGA control. Since less than 2% of DNA and binary events were longer than 20 msec, the waiting period of 20 msec ensured that nearly all controlled events were ternary complexes.

In our second implementation of FSM/FPGA voltage control, we demonstrated efficient automated detection of individual DNA complexes (no KF enzyme present in cis-chamber), based on the characteristic 20 pA amplitude (Wilson et al. (2008) Rapid finite state machine control of individual DNA molecules in a nanopore. In International Conference on Biomedical Electronics and Devices (BIO-DEVICES), to appear, Madeira, Portugal). For all events that fell within a threshold range of 20±2.8 pA, the voltage was promptly reduced to extend the DNA dwell time. In a second experiment, for all DNA events that fell within a threshold around the 20 pA level, the voltage was promptly reversed to expel the DNA back into the cis chamber prior to translocation. Both implementations (detecting and reacting to enzyme-bound DNA events and detecting and reacting to enzyme-free DNA events) were foundational achievements, and prompted us to attempt to detect and discern between both types of events individually, and in real time.

Example XII

Equipment

A patch-clamp amplifier, Molecular Devices AxoPatch 200B, regulates the applied voltage and measures the ionic current through the channel. The data are recorded using the Molecular Devices Digidata 1440A digitizer, sampled at 50 kHz and low-pass filtered at 5 kHz with a four-pole Bessel filter. One of our stations uses a different patch clamp, the A-M Systems Model 2400.

Example XIII

Control Logic: Hardware and Software

The voltage control logic is programmed using a finite state machine (FSM) within the LabVIEW 8 software. The FSM logic is implemented on a field-programmable gate array (FPGA) hardware system, National Instruments PCI-7831R. An FPGA is a reconfigurable hardware platform that permits fast measurement and voltage reaction times (1 µsec output sample time). An FSM is a logic construct in which program execution is broken up into a series of individual states. Each state has a command associated with it, and transitions between states are a function of system measurements. Measurements of the pore current are processed and passed to the FSM as inputs. Changes in the FSM control logic are made as necessary, without the need to re-compile and re-route the design to run on the FPGA. This achieves a balance between speed and flexibility, by enabling the system to react to events on the order of a microsecond, while also allowing for the control logic to be reconfigured as necessary between experiments.

Example XIV

Filtering and Thresholding Ionic Current

Our control logic requires efficient detection of ionic current blockades (events) that result from DNA alone or KF-bound DNA. Further, the logic must be able to efficiently distinguish between these two event types. At 180 mV, mean amplitudes for DNA alone and KF-bound DNA are 20 pA and 23 pA, respectively; a difference of 3 pA. To distinguish DNA alone from KF-bound DNA events in real time, the incoming current signal on the FPGA is filtered and thresholded.

Threshold levels are determined a priori, by constant voltage experiments with the biological components to be detected in the cis chamber. In our experiments with KF, amplitude thresholds consistent with KF-bound or KF-free event amplitudes were identified at 180 mV and 150 mV. At 180 mV, for example, the threshold identified and used to detect DNA alone events was 20±2.8 pA; the threshold identified and used to detect KF-bound DNA events in was 24±2.8 pA. In our experiments to date, one or two thresholds have been implemented at a time. In future work, more than two thresholds may be utilized at the same time, to distinguish multiple macromolecular states that are known to differ based on the attenuated amplitude.

Filtering is used to mitigate noise. Since the ionic current peak-to-peak noise routinely exceeds 3 pA at 180 mV, DNA alone and KF-bound DNA events would not be reliably distinguishable by monitoring the raw current amplitude. By filtering the current amplitude, we have demonstrated detection of DNA alone events and KF-bound DNA events in real time. A windowed mean filter has been used in our experiments so far, including in our invention's initial demonstration shown in Section 2.3. Recently, a superior exponentially-weighted mean filter was identified and will be used in new experiments. Details on the two filters are given below.

Example XV

Moving Average Filter

Every 5.3 μsec, the FPGA samples the ionic current and computes a windowed mean amplitude, using a window size of 0.75 msec. If the mean enters a chosen threshold range, the FPGA detects entry and continues to monitor the mean, re-checking the threshold every 0.2 msec. If the mean remains within the threshold range for four consecutive checks, the FSM logic diagnoses the blockade as an event type known to be consistent with the chosen threshold.

In the absence of a change in voltage, the expected time delay between the start of an event and diagnosis of an event is 1.35 msec; 0.75 msec for the windowed mean to first enter the threshold, and 0.6 msec for three more confirmed tests. In practice, the diagnosis time ranges from 1.1 to 2.5 msec. The mean filter was implemented in our invention's initial demonstration (detailed below).

Example XVI

Exponentially-Weighted Moving Average Filter

Through post-experiment analysis, our mean filter was shown to falsely detect terminal steps within ternary events. Specifically, the FSM/FPGA was programmed to detect ternary level amplitudes, wait until the terminal step, and upon detection of the terminal step, reverse the voltage to expel the unbound DNA into the cis chamber. Examination of the data showed voltage reversal for many events in which no terminal step was clearly present, although the presence of terminal steps in ternary events is high (97%) with no voltage reversal.

To improve the FSM's robustness to false detections of terminal steps, an exponentially-weighted moving average (EWMA) filter is now being explored to replace the mean filter. The EWMA filter represents a digital implementation of an analog RC filter commonly used for signal smoothing in electrical engineering applications. The filter calculates a moving average that places exponentially less significance on past samples and allows the filtered signal to better track the real signal. EWMA filtering also performs signal smoothing more efficiently than a simple moving average due to its recursive implementation:

$$\bar{i}(t)=(1-\alpha)i(t)+\alpha\bar{i}(t-1), \quad (1)$$

where $i$ and $\bar{i}$ are unfiltered and filtered current signals, respectively, and $t$ is the sample number. Filtering the data from the terminal step detection experiments offline, with a=0.9, showed a substantial improvement in robustness to false positives over the mean filter. As with the mean filter, four consecutive threshold tests will be used for event diagnosis, waiting 0.2 msec between threshold tests.

In the absence of a change in voltage, the expected time delay between the start of an event and diagnosis of an event is 0.7 msec; 0.1 msec for the EWMA to first enter the threshold, and 0.6 msec for three more confirmed tests. More rigorous evaluation of EWMA detection times will be part of our ongoing work.

Example XVII

Time Scales for Changing the Voltage Field Force

When the magnitude of the voltage across the membrane changes, a capacitive transient is superimposed on the measured ionic current. The transient is present in all alpha-hemolysin nanopore studies that involve voltage change (see, for example, Bates et al. (2003) supra), and necessarily masks some information in the measured current for a defined and manageable segment of each event. In our invention, the transient implies that, when the control logic is programmed to diagnose an event type after a voltage change, the filtered current amplitude will not enter a chosen threshold(s) for event diagnosis until the transient has sufficiently settled.

The settling time for the transient is proportional to the net change in voltage. In the voltage control experiment, the changes in applied voltage are from 180 mV to −50 mV, and −50 mV to 180 mV. For a net change of 230 mV (absolute value), we observe that 98% of transients have sufficiently decayed for accurate thresholding after 2.5 msec. In our initial tethered DNA experiments, voltages changes were 200 mV and 170 mV (absolute value). Transients resulting from voltage changes are observable in FIGS. 17-18.

In the presence of a change in voltage, the time required for diagnosis of an event (as a DNA event or an enzyme-bound DNA event) is expected to match the voltage transient settling time. This is because the transient settling time is typically longer than the time required for the filtered amplitude to converge onto the measured ionic current signal. Thus, diagnosis time is expected to be at most 2.5 msec for voltage changes of 230 mV (absolute value), and less than 2.5 msec for smaller voltage changes.

Example XVIII

Tethered DNA Configuration

In our initial tethered DNA experiments, a single DNA 20 bphp was captured in the pore, tethered, and threaded back and forth through the pore under voltage control for repeated KF binding and unbinding to the ss-ds junction in the cis chamber. In the experiment, 1 μM 100mer DNA, 5 mM $MgCl_2$, 2 μM KF, and 200 μM of dGTP were present in the cis well of the pore. Thus, each event results from DNA alone or a ternary complex captured in the nanopore.

The DNA oligomer is designed for tethering. Specifically, the 3' end is formed into a 20 base pair hairpin, and 2 μM of 20 mer primer complementary to the 5' end is present in the trans chamber. Upon capture of the 5' end, voltage is reduced to hold the DNA in the pore, but not unzip the 3'-end hairpin in the vestibule (if an unbound DNA molecule was captured) or dissociate KF/dGTP from the ss-ds junction (if a ternary complex was captured). After a sufficient time period, the 20 mer primer anneals to the 5' end, creating a 20 mer duplex on the trans side of the pore. Details of our initial experiments are now provided.

Figure 15:
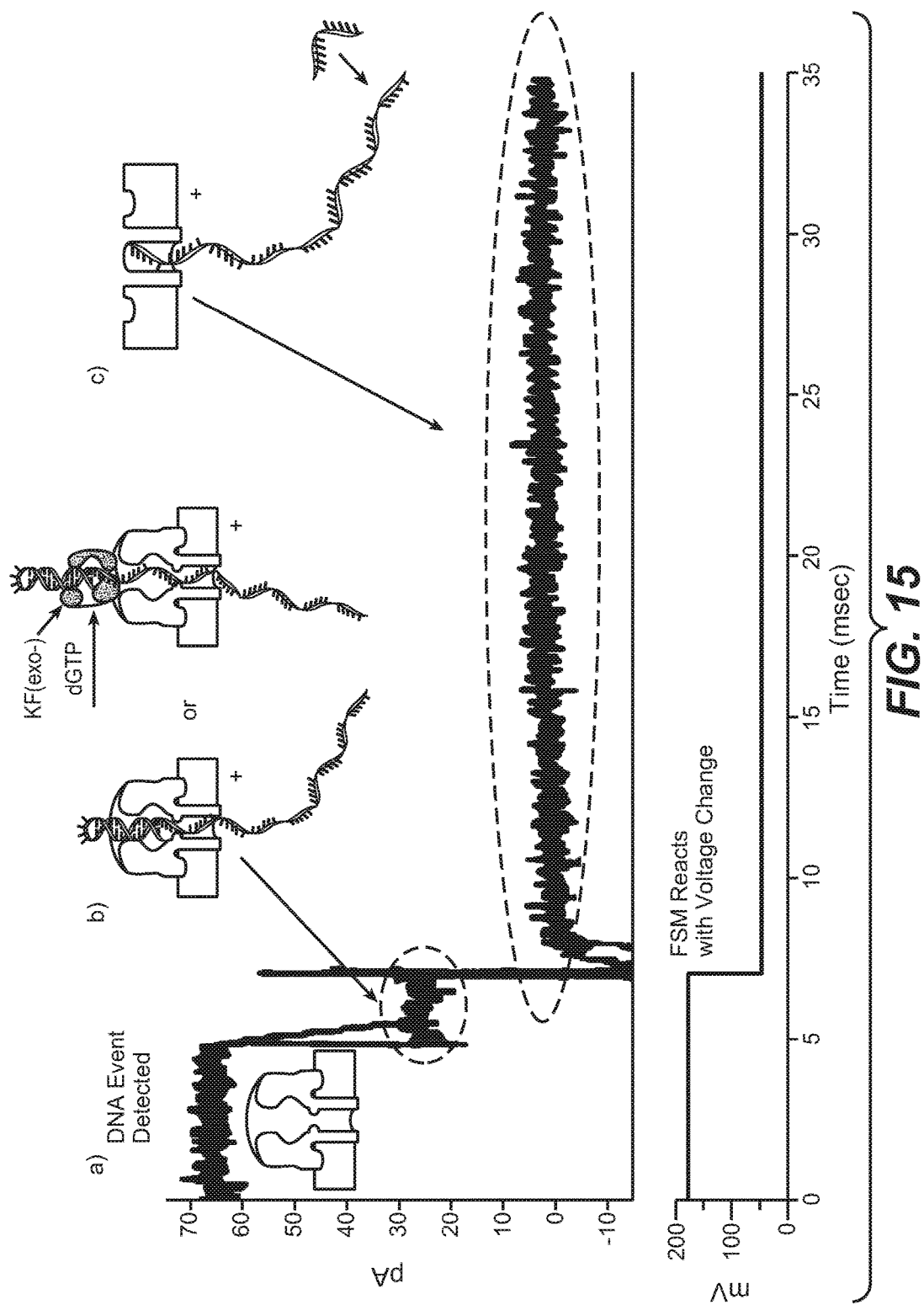
FIG. 15 illustrates tethering of a captured DNA oligomer by annealing a trans-side primer. a) The finite-state machine (FSM) monitors the open channel current for translocation events. b) Captured molecule causes the current to attenuate, and the FSM diagnoses an event (DNA or DNA/KF/dGTP) based on the threshold [15.75, 26.75] pA. c) Upon event diagnosis, the FSM reduces the applied voltage to 50 mV for 20 sec, during which time the 20 mer primer anneals to the 5' end. The graphic shows a close up of the lower half of nanopore, with the 5' end and 20 mer primer in the trans chamber.

In the experiment, 180 mV applied voltage was used to capture each DNA molecule in the pore with the 5' end translocating into the trans chamber. When a DNA event (threshold of [15.75, 21.25] pA) or a KF-bound DNA event (threshold of [21.25, 26.75] pA) was diagnosed using the mean filter, the FSM reduced the potential to 50 mV, to hold the molecule in the pore but not unzip the hairpin or dissociate KF/dGTP. The 50 mV hold voltage was applied for 20 sec, a period sufficient for the 20 mer primer to anneal to the 5' end of the DNA in the trans chamber. The initial tethering phase of a captured DNA molecule is shown in FIG. 15.

After 20 sec, the FSM reversed the voltage to −20 mV, forcing the DNA toward the cis side of the pore with enough force to abut the 5' duplex against the trans-side end of the channel, and dangle the ss-ds junction of the 3' end hairpin into the cis chamber. The −20 mV voltage was found to be small enough to not unzip the 5'-end primer duplex. The amount of time at the −20 mV voltage is referred to as the fishing time $t_{fish}$, measured in seconds. Application of −20 mV for tfish seconds is referred to as the fishing mode of the control logic.

After $t_{fish}$=5 seconds at −20 mV, the FSM changed the voltage to 180 mV, then monitored (thresholded) the mean filtered amplitude to diagnose the identity of the molecule in the pore as either DNA alone or enzyme-bound DNA. If unbound DNA was diagnosed ([15.75, 21.25] pA threshold), voltage was revered to −20 mV to restart the fishing mode. Otherwise, the FSM continued to monitor the filtered amplitude. Within a KF/dGTP-bound event, upon diagnosis of the terminal step ([15.75, 21.25] pA threshold), voltage was reversed to −20 mV to restart the fishing mode.

Figure 16:
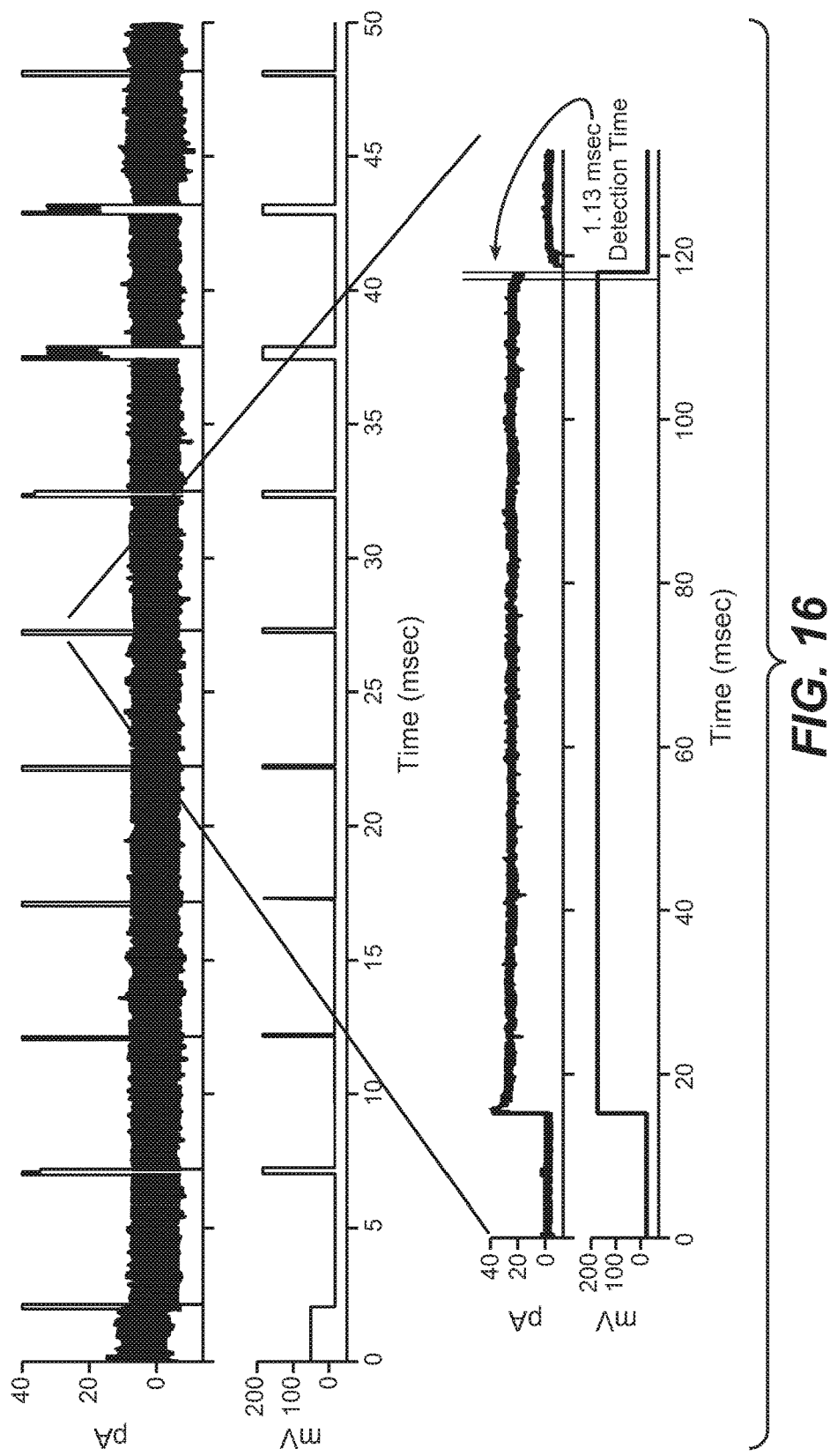
FIG. 16 illustrates a time course of ionic current signal in tethered DNA experiment. First 2 seconds shows the end of the 20 sec tethering waiting period (50 mV applied) for 5'-end primer to anneal in trans chamber. Fishing time of $t_{fish}$=5 seconds used, with nine probe events shown. Probe event number 5 is blown-up to show details of an enzyme-bound event, with terminal step and subsequent terminal step diagnosis after 1.13 msec. Since enzyme-bound events last ~100 msec, the control logic is primarily in fishing mode in this experiment.

Application of 180 mV until unbound DNA is diagnosed (by DNA alone or by reaching the terminal step of an enzyme-bound event) is referred to as the probing mode of the control logic. The first nine fish-then-probe actions within a tethered DNA experiment are displayed in FIG. 16. Once the DNA is tethered, and the FSM logic begins the fish-then-probe cycle, only the unbound DNA threshold is used for diagnosis, of unbound DNA or of a terminal step within and enzyme-bound DNA event. The FSM logic repeats the fishing mode then probing mode cycle until the tethered DNA molecule translocates through the pore, and the open channel current is detected. DNA translocates if the 3'-end hairpin is unzipped or if the 5'-end duplex is unzipped. We expect that DNA translocation is most likely to occur by unzipping the 3'-end hairpin, since unzipping at 180 mV can happen faster than DNA event diagnosis. The −20 mV voltage, on the other hand, is less likely to unzip the 5'-end duplex, even for fishing times on the order of minutes. Post experiment analysis can be used to determine the frequency of DNA translocation in probing mode versus fishing mode. When the tethered DNA translocates and current returns to the open channel value, the FSM resets and monitors the current for another event to tether a new DNA molecule.

Figure 17:
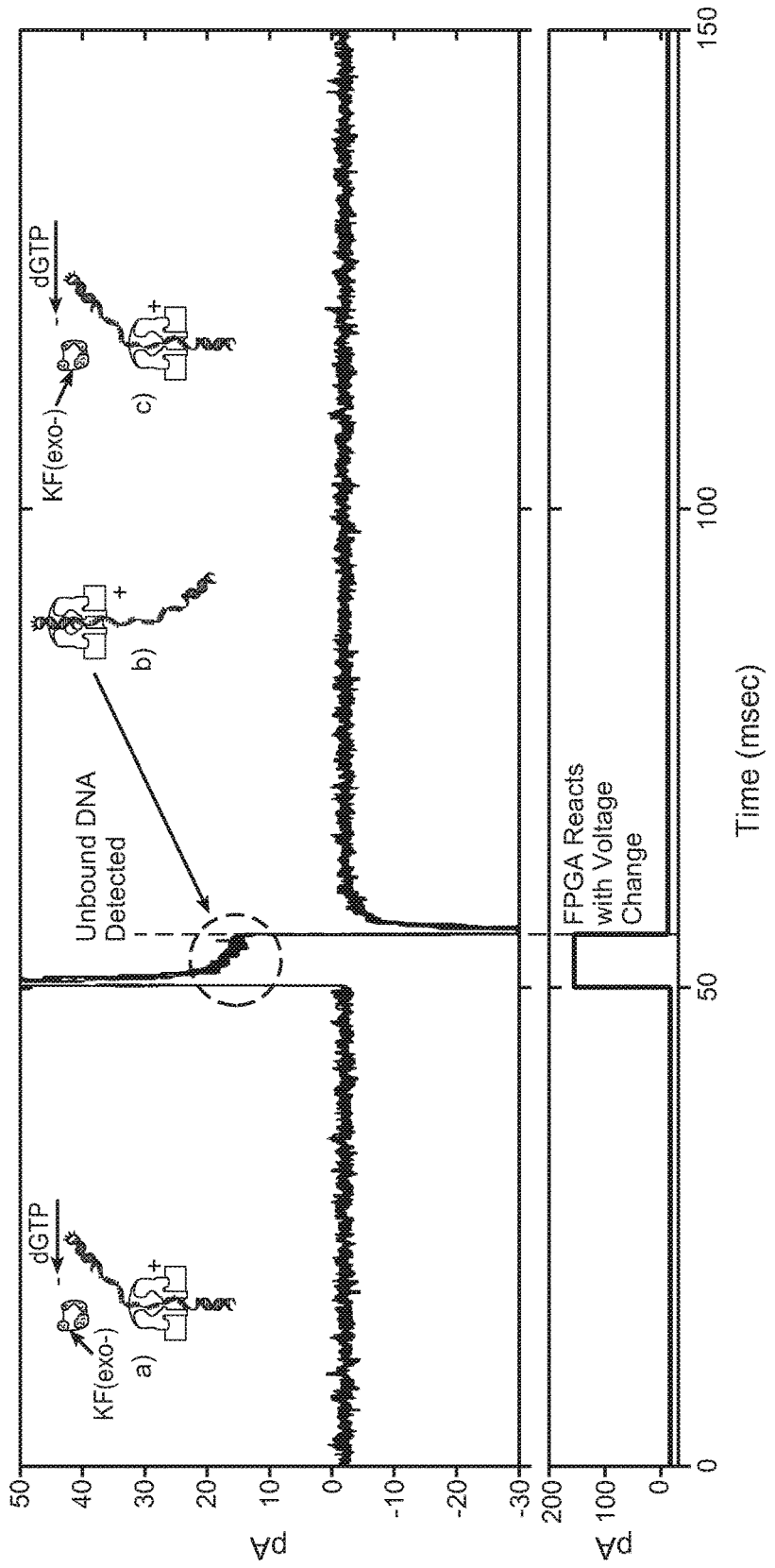
FIG. 17 illustrates fishing and probing of tethered DNA molecule in a nanopore. a) Fishing mode, with $t_{fish}$=0.521 sec. b) Probing mode, in which the FSM applies 150 mV until a DNA alone event is diagnosed with threshold [7.5, 15.5] pA. In the event shown, DNA alone is diagnosed as soon as the transient settles, with no enzyme bound to the DNA, and the fishing mode is restarted. c) Fishing mode.
Figure 18:
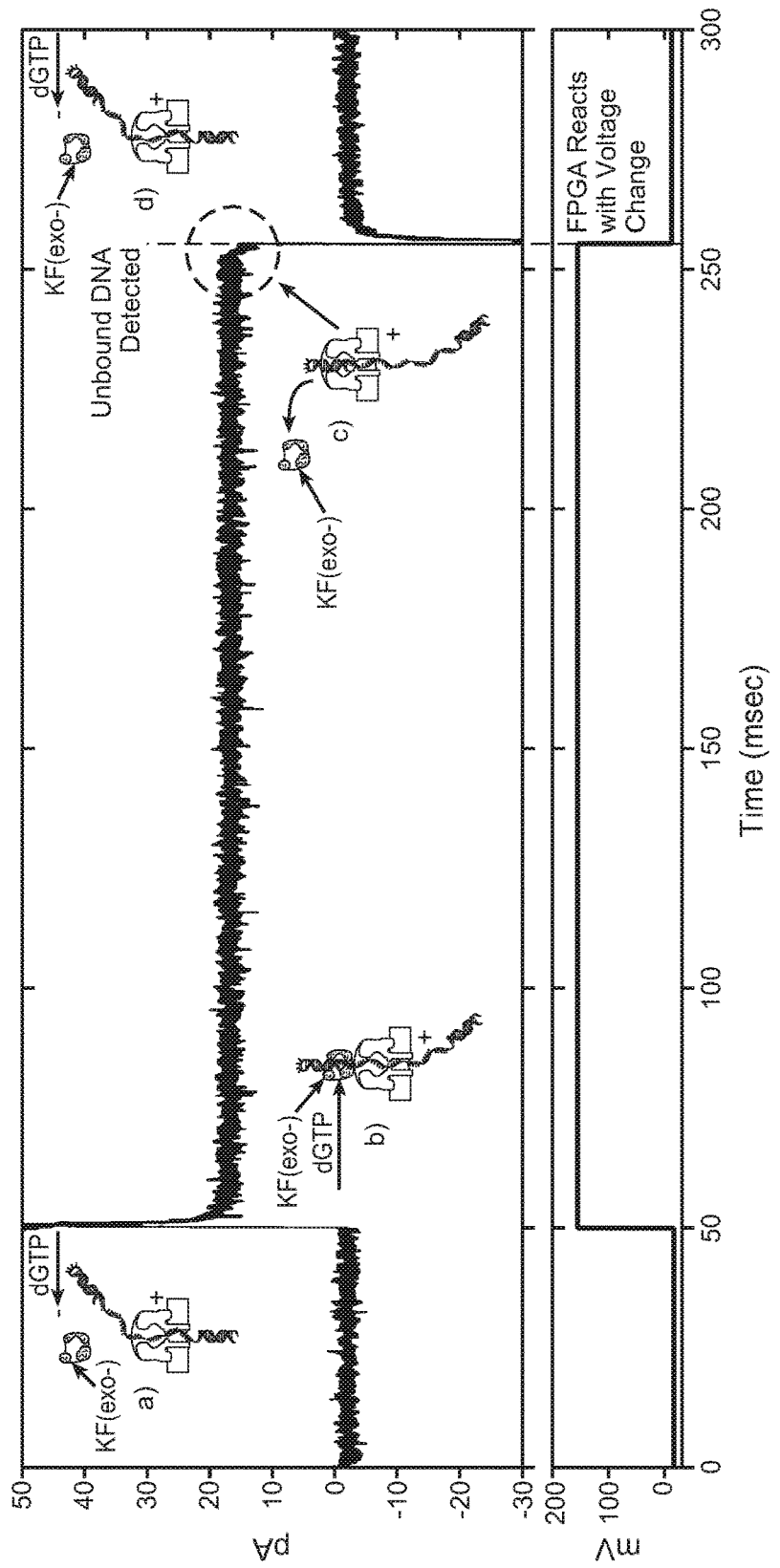
FIG. 18 illustrates another method for fishing and probing of tethered DNA molecule in a nanopore. a) Fishing mode, with $t_{fish}$=0.521 sec. b) Probing mode, in which the FSM applies 150 mV until a DNA alone event is diagnosed. In the event shown, enzyme-bound DNA is diagnosed, and the FSM continues to monitor the filtered amplitude. c) The terminal step is diagnosed, using the [7.5, 15.5] pA threshold, and the fishing phase is restarted. d) Fishing mode.
Figure 19A:
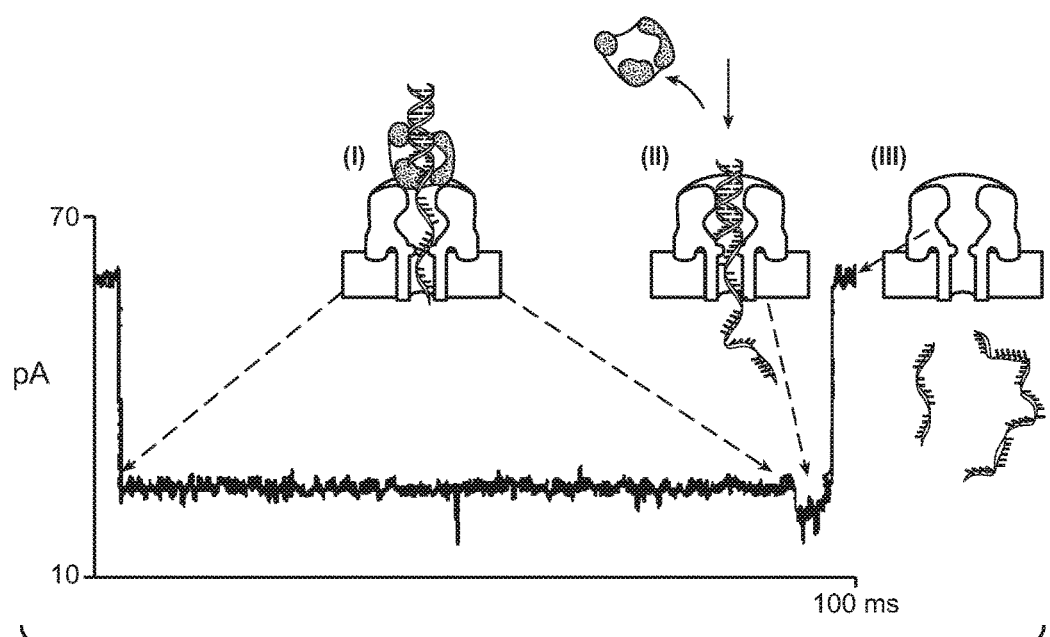
Figure 19F:
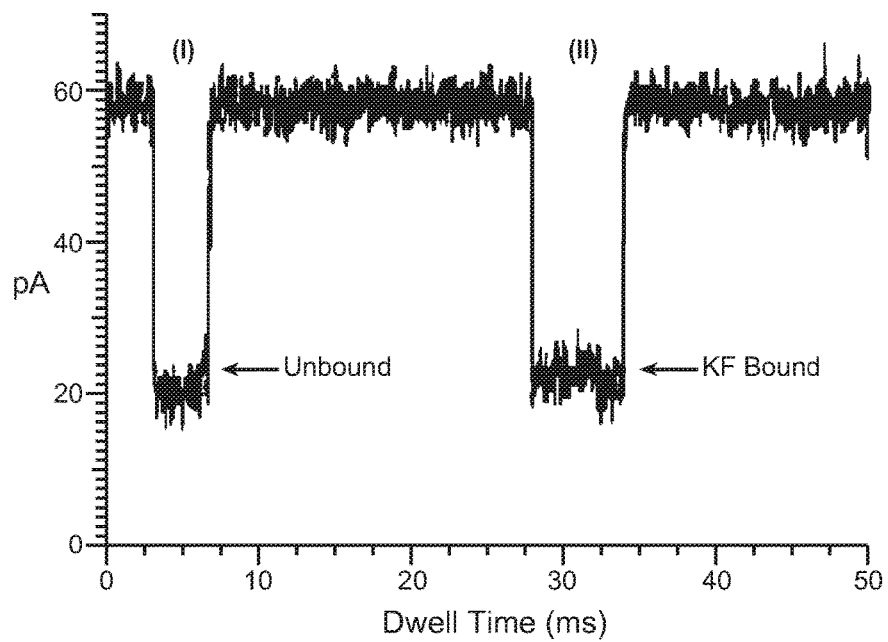
Figure 20A:
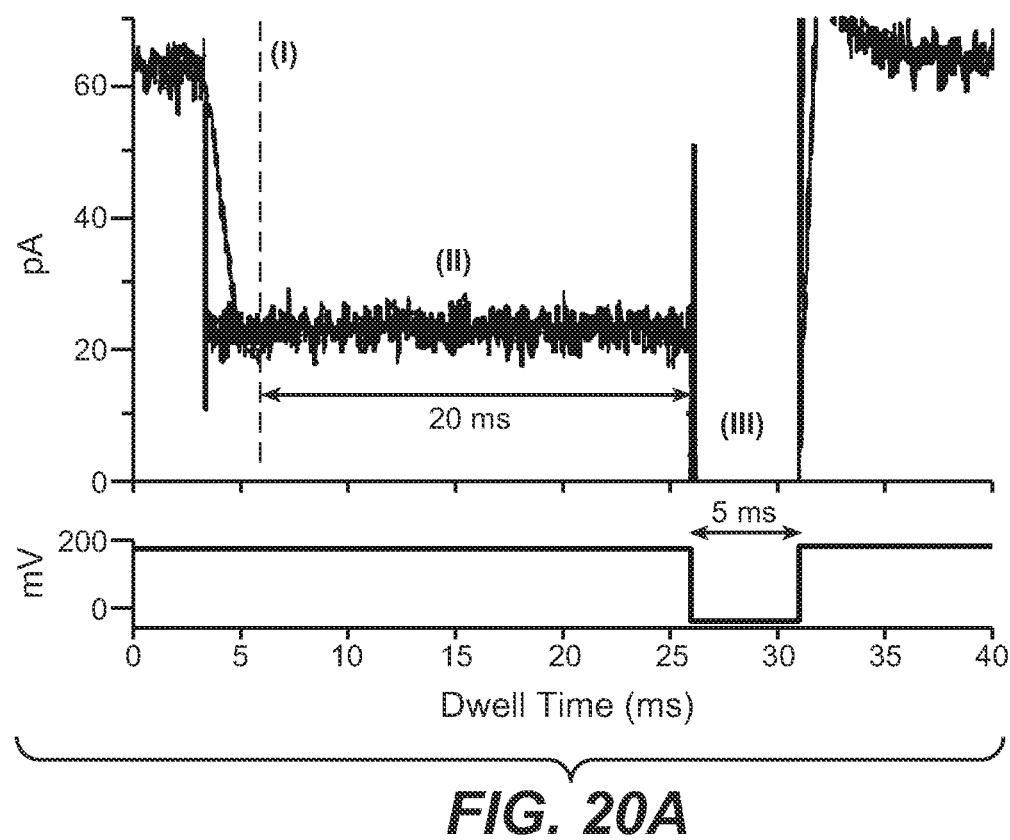
FIG. 20A-20B illustrates a representative ternary complex event under FPGA control.
Figure 20B:
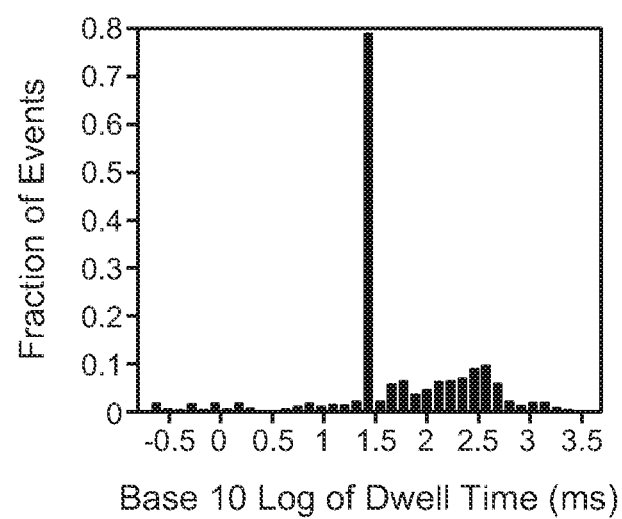

In a second experiment a lower capture and probing voltage of 150 mV was used, and a faster fishing time of $t_{fish}$=0.521 seconds was used. Based on experiments with DNA alone and DNA with KF and dGTP at constant 150 mV, the unbound DNA threshold was set to [7.5, 15.5] pA and the KF/dGTP-bound DNA threshold was set to [19, 27] pA. Fishing and probing modes are shown in FIG. 17, where probing reveals a DNA alone event. Fishing and probing modes are shown again in FIG. 18, where probing reveals an enzyme-bound DNA event. The FSM captured and tethered eight independent DNA molecules. In total, 337 enzyme-bound DNA events occurred in probing mode over a time period of 380 seconds. Analysis of the data shows the FSM/FPGA correctly diagnosed the terminal step in these events 72% of the time. In the remaining 28%, fishing was restarted before a terminal step actually occurred in the enzyme-bound DNA event (referred to as a false positive). Offline analysis showed that the EWMA filter resulted in zero false positives in this data. Online implementation of the EWMA filter in future tethered DNA experiments will be used to gauge and improve the robustness of the filter to false positives. An "unbound-DNA check" mechanism can be explored to rule out/minimize false positives. The mechanism works as follows: at the end of each probing mode, fish for a period too short to expose the ss-ds junction in the cis-chamber, then re-probe to ensure the DNA is unbound; if unbound, being fishing for period $t_{fish}$; if bound, wait until terminal step detected. Identification of the brief fishing period used to confirm that the DNA is unbound will be part of our ongoing work.

Example XIX

Rapid Detection and Control to Probe Individual DNA and Enzyme-Bound DNA Molecules in a Nanopore In the biological nanopore setup, a planar lipid bilayer is created across a 20 μm TELON aperture in a KCl solution. A single α-hemolysin protein channel is inserted into the planar lipid. The channel (pore) is 15 nm in length and varies in diameter. The cis-opening of the pore is 2.6 nm wide, opening to a 3.6 nm vestibule before narrowing to a limiting 1.5 nm width at the beginning of the stem. The remainder of the stem up to the trans-opening is 2 nm wide. The vestibule is large enough for double-stranded DNA (dsDNA) to enter, but the limiting stem is just wide enough for ssDNA to pass through. Across the bilayer, AgCl electrodes are used to apply a potential that produces an ionic current through the pore (FIG. 12). The field created by this voltage pulls the negatively charged phosphate backbone of the ssDNA or RNA through the pore, passing from the cis side to the trans side of the pore with the trans-side voltage positive. As molecules translocate, the pore becomes partially blocked by the translocating molecule, causing a momentary drop in current. These translocation events can be characterized by the amplitude of the blockade current and the time the molecule spends in the pore, defined as the dwell time. The DNA used in the experiments presented here are comprised of ssDNA and dsDNA segments. Specifically, for the non-FPGA experiments disclosed herein, a 14 base pair hairpin (14 bphp) 67 nucleotides in total length was used. For the rest of the experiments, a DNA oligomer that is 79 nucleotides total in length, with a 20 bphp was used. The hairpin was formed by folding the 3' end over itself, creating 14 or 20 base pairs. The hairpin is thus the double-stranded segment, with the single-stranded segment 35 nucleotides long for both the 14 and 20 bphp (4 unpaired bases in the doubled-stranded end loop). Upon capture of the ssDNA end, the hairpin enters the pore vestibule and remains until the hairpin is unzipped. A schematic of the nanopore system and an example 20 bphp translocation event is illustrated in FIG. 13.

Correlations between the ionic current amplitude and features of individual DNA or RNA molecules translocating through the pore has been shown through various assays using α-hemolysin nanopores. A near direct correlation between the number of molecules passing through the pore and the number of current drops has been demonstrated. Homopolymers of ssDNA and block copolymers of RNA are also distinguishable based on the measurable differences in the blockade current amplitude or kinetics. However, translocation rates are too fast (up to 2 nucleotides/μsec) for sequencing individual nucleotides in heterogeneous single-stranded polymers using existing biological nanopores. Here and in other studies, DNA with single and double stranded segments is used to increase the dwell time of nucleotides in the pore (0.5-5 msec, depending on applied voltage and dsDNA segment length). For example, blunt-ended hairpins, those with no single-stranded overhang, ranging from 3 to 9 bases long are used in Vercoutere et al (2001; Nat. Biotechnol, 19(3):248-252, and Vercoutere et al. (2003) Nucleic acids research, 31:1311-1318), where machine learning methods were applied to the extended dwell time events to identify (sequence) the terminal base pair made up of the 3' and 5' ends of the ssDNA.

Example XX

Voltage Control Using FSM/FPGA

The nanopore system is setup in a 0.3 mM KCl solution. A patch-clamp amplifier, Molecular Devices AxoPatch 200B, regulates the applied voltage and measures the ionic current through the channel. The data are recorded using the Molecular Devices Digidata 1440A digitizer, sampled at 50 kHz and low-pass filtered at 5 kHz with a four-pole Bessel filter.

The voltage control logic is programmed using a FSM within the LabVIEW 8 software. The FSM logic is implemented on a field-programmable gate array (FPGA) hardware system, National Instruments PCI-7831R. An FPGA is a reconfigurable hardware platform that permits fast measurement and voltage reaction times (1 μsec output sample time). An FSM is a logic construct where program execution is broken up into a series of individual states. Each state has a command associated with it, and transitions between states are a function of system measurements. Measurements of the pore current are processed and passed to the FSM as inputs. Changes in the FSM control logic are made as necessary, without the need to re-compile and re-route the design to run on the FPGA. This achieves a balance between speed and flexibility, by enabling the system to react to events on the order of a microsecond, while also allowing for the control logic to be reconfigured as necessary between experiments.

Example XXI

FSM Monitoring of Mean Filtered Current for DNA and Enzyme-bound DNA Event Diagnosis Blockade events, quantified by the blockage current and dwell time, can be detected and monitored in real time using the FSM/FPGA. A mean filter applied to the incoming current signal on the FPGA removes a large portion of the peak-to-peak noise. Specifically, every 5.3 μsec, the FPGA samples the ionic current and computes a windowed mean amplitude. The FPGA tests if the mean is within a pre-specified range and then continues to test the mean every 0.2 msec after initial detection. If the mean enters and remains within this range for four consecutive tests, the FSM logic diagnoses the blockade as a DNA hairpin event. The time delay between a DNA translocation event and diagnosis of a DNA translocation event is nominally 1.35 msec; 0.75 msec for the windowed mean to first enter the 17.2 to 22.8 pA range, and 0.6 msec for three more confirmed tests, and 0.65 ms of computational delay. The mean filtered current is used for DNA event diagnosis and triggers the transitions between states in the FSM control logic.

The FSM control logic has been used to discern between DNA alone or DNA/enzyme complex using the nanopore system. Additionally, enzyme dissociation from DNA can be detected and reacted to in real time using the FSM to detect the terminal steps present in the current signal. The ability to detect both DNA and DNA/enzyme complex in the pore can permit the real-time identification of the base at the junction between single-stranded and double-stranded DNA when KF is bound to a DNA hairpin and the correct nucleotide is present in the system, as detailed in this report.

Furthermore, the detection and control of single DNA hairpin molecules can be expanded to include repeated capture of KF using a single copy of DNA. One base can be identified when KF is pulled off a DNA hairpin using a nanopore. Repeated capture and dissociation of KF from the same copy of DNA can allow many bases to be sequenced provided a method for single-base ratcheting polymerase reaction is found. Current sequencing methods are limited to read lengths of around one kilobase (1000 base pairs identified), but a nanopore-based sequencing method has potential for much longer read lengths when compared to traditional bulk sequencing methods.

The bulk of the future work is dedicated to improving the detection robustness by increasing the signal-to-noise of the current signal through improved filtering and use of longer DNA hairpins. Also, a double-checking scheme to ensure the enzyme has dissociated will be implemented. Experiments that vary the concentration of KF and dNTP will also be performed to find the detection limit of different complexes.

Example XXII

Detection of Molecular Complexes

Figure 14B:
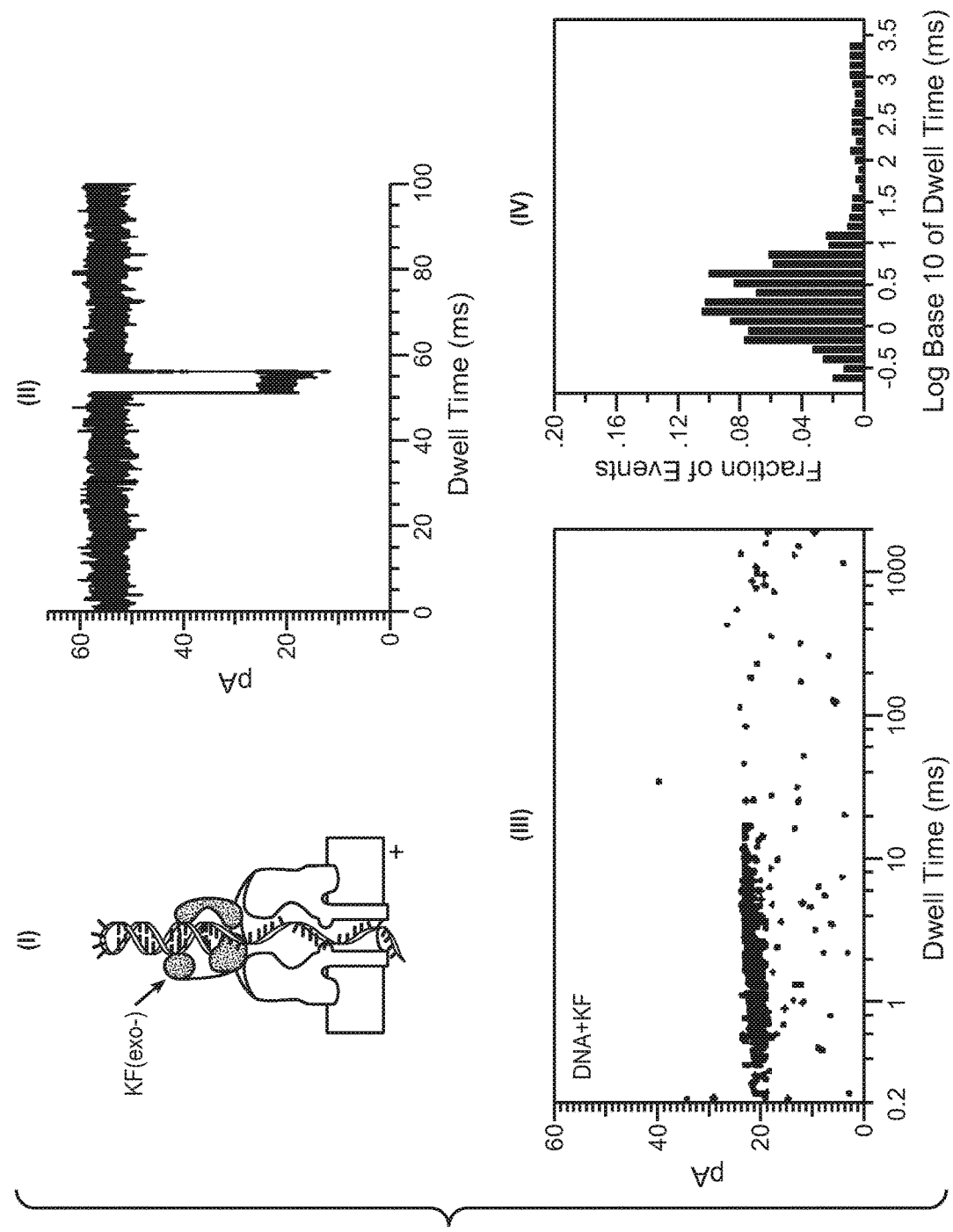
Figure 14C:
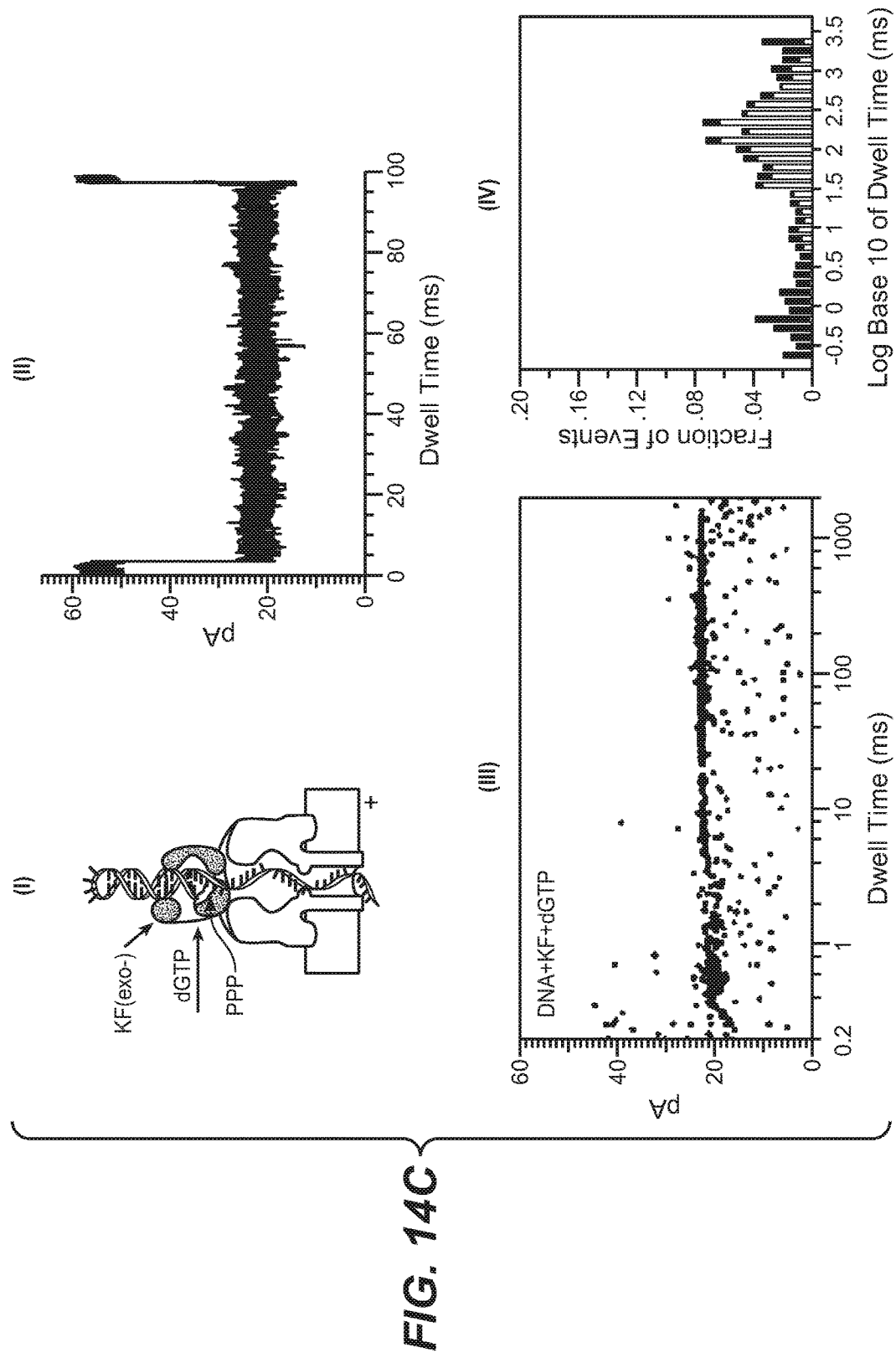

The interaction of DNA with Klenow fragment (KF) of *Escherichia coli* DNA polymerase I can be probed with the nanopore system. In the absence of KF, capture and subsequent unzipping of 20 bphp at constant 180 mV reveals current blockades with 20 pA mean amplitude and 4 msec median dwell time. Addition of KF and the dNTP complementary to the DNA template base in the KF catalytic site yielded a substantial increase in blockade dwell times (110 msec median lifetime for dGTP), attributable to ternary (DNA/KF/dGTP) complexes. Closer investigation of such blockades revealed a two-step pattern in greater than 97% of the blockades, the first step at 24 pA mean amplitude, and the second (terminal) step at 20 pA mean amplitude, lasting 4 ms consistent with the hairpin kinetics alone. It was demonstrated that the transition from step one to two resulted in dissociation of KF from DNA first, followed by the hairpin dropping into the pore vestibule until unzipping occurred. As an initial effort at voltage control of enzyme-bound DNA, efficient automated detection (<3 msec) of individual ternary complexes was demonstrated, based on the characteristic 24 pA amplitude and truncation of the blockade time by voltage reversal after 20 msec. The 20 msec cutoff was used because 60% of events are longer than 20 msec in the presence of the correct dNTP, while only 2% of events are longer than 20 msec and in the detection range absent the correct dNTP, showing that events longer than 20 msec usually correspond to ternary complex events (FIG. 14A-14C). Detection was based on the mechanism described in Section 1.2.2 for calculating the windowed mean using the previous 1.5 msec of signal and a detection range of 17.2 to 22.8 pA. The basis for choosing this range is that ~20 pA is the median amplitude for 14 and 20 bphp events at 180 mV as well as the terminal step (FIG. 19A-19F).

The ability to diagnose individual events in real time shows potential for extending this system to sequencing. A single long dwell time event (>20 msec) gives high probability of a ternary complex event. Based on the dNTP present in the system, the identity of the next base to be added can be identified, achieving single base sequencing. For multiple base reads, regulation of base polymerization is necessary to step along the addition of nucleotides. For every base added, enzyme-bound DNA present in the pore can be probed for the presence of ternary complex, confirming the correct dNTP is present for polymerization. In the experiments presented here, the dNTPs are di-deoxy terminated so polymerization is stalled, preventing more than a single base addition to the hairpin. This use of di-deoxy terminators is the foundation of most sequencing methods employed today.

Example XXIII

Control of Individual DNA Molecules

Rapid detection (<2 msec) is based on computing a filtered mean amplitude, based on the last 0.75 msec of the ionic current, in real time and monitoring the mean relative to an amplitude range consistent with DNA hairpin blockades (20±2.8 pA). Upon detection, two methods of voltage control were demonstrated.

In the first method, dwell time extension is achieved by prompt voltage reduction, with the reduced voltage applied until the hairpin unzips. A higher voltage for capture increases the number of molecules examined, and the reduced voltage post-capture increases the dwell time to, in principle, facilitate sequencing. In particular, extending the life of DNA hairpins in the pore increases the time within which a terminal base identification could be achieved using machine learning methods.

The second method reduces the voltage for a preset time (10 msec) and then reverses the voltage to expel the molecule prior to hairpin unzipping. This demonstrates control authority to aggregate the dwell times of hundreds of blockade events. Additionally, it complements previous work, confirming the ability to detect both DNA-enzyme blockades and DNA hairpin blockades. Confirmation of the ability to discern between each blockade type in real time is crucial to future work. Ultimately, nanopore-based characterization of enzyme dynamics will require direct detection and control of multiple DNA conformations relative to the enzyme, and direct control of enzyme-free DNA is a prerequisite toward developing this capability.

Direct control of ssDNA in a nanopore has been demonstrated, in which detection of DNA is based on monitoring the raw amplitude relative to a threshold level. Voltage level changes, comparable to those employed here, were commanded to explore the zero and low voltage effects on ssDNA-pore interactions. In contrast to thresholding the raw ionic current amplitude, the windowed amplitude mean calculation used here filters the current noise. Additionally, detection depends on the mean remaining within a preset amplitude range (<6 pA in spread) for multiple consecutive comparisons, resulting in fewer false detections than a single threshold comparison.

Example XXIV

Experiments and Results

A demonstration of direct FSM/FPGA control of single DNA molecules in a nanopore is now described. In a first experiment, the objective was to efficiently detect DNA hairpin events, one molecule at a time and increase the blockade dwell time by lowering the applied voltage from 180 mV to 150 mV upon detection. This is referred to as "dwell time extension control". After completing this objective, the aggregation of the extended blockade dwell times was sought by expelling the DNA using voltage reversal of −50 mV after 10 msec at 150 mV. This is referred to as "dwell time aggregation control". The motivation was to increase the nominal hairpin dwell time, but expel the molecule before unzipping the hairpin. A tighter distribution for the aggregated dwell time events, in contrast to the distribution of the extended dwell time events, will indicate that the objective has been met.

Figure 21A:
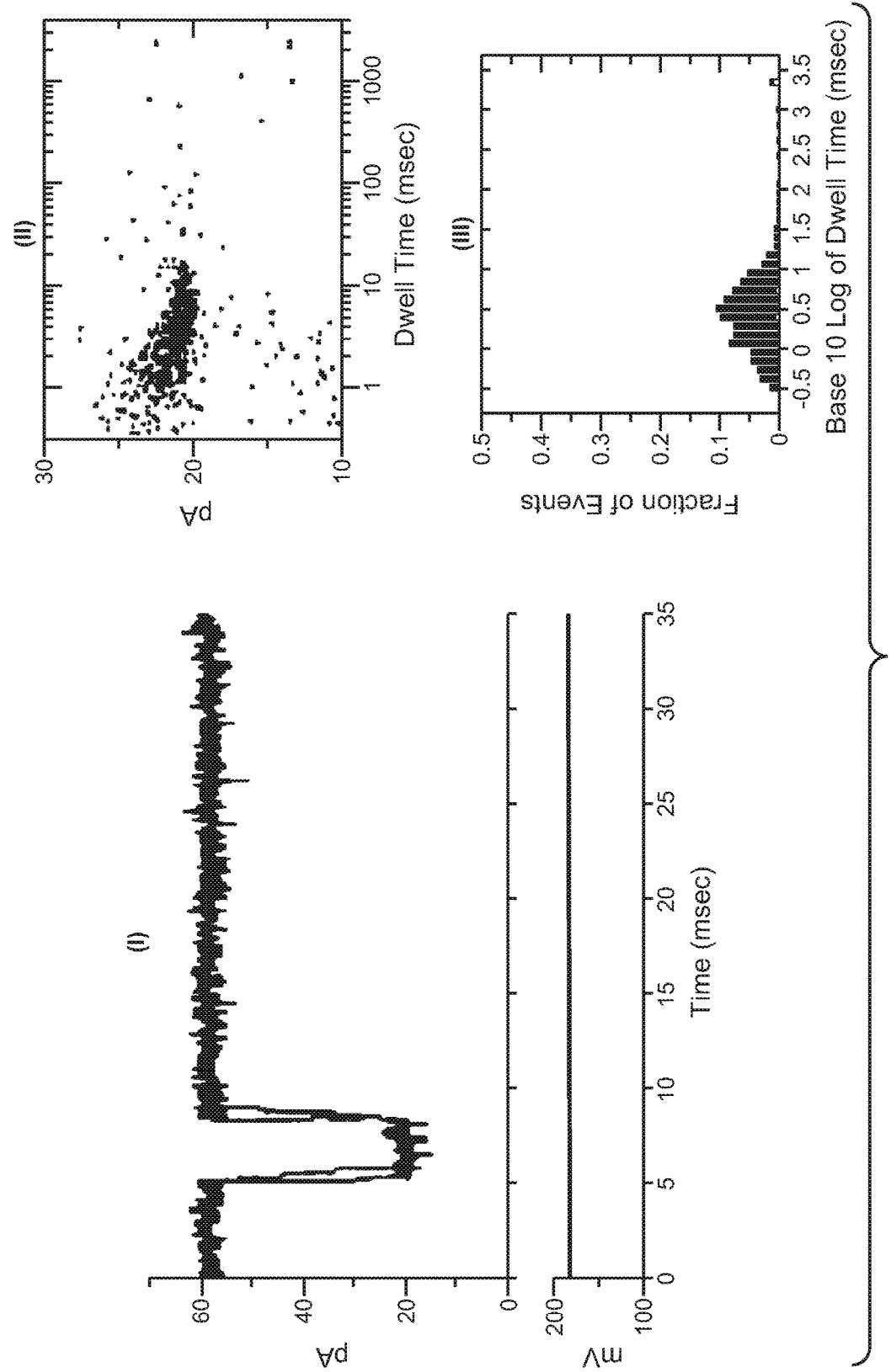
FIG. 21A-21C illustrates regulation of 20 base pair hairpin (bphp) dwell time using FSM control. In (I) for each of FIGS. 21A, 21B and 21C, the lighter current signals are low-pass filtered at 5 kHz, the darker signal is a mean filtered current, and the lower voltage signal is the commanded voltage. Typical events and corresponding voltage signals under constant 180 mV voltage (FIG. 21A), dwell time extension control (FIG. 21B), and dwell time aggregation control (FIG. 21C). (II) in each of FIGS. 21A, 21B and 21C gives an event plot of DNA events, showing average amplitude vs. dwell time for each event. (III) in each of FIGS. 21A, 21B and 21C gives probability histograms of the base 10 logarithm of dwell time for all events (filled bars), and for subset of events in range 13 to 18 pA (open bars).

A typical 20 bphp event at constant 180 mV voltage is shown in FIGS. 13 and 21A(I). The probability histogram of the base 10 logarithm of dwell time (FIG. 21A(III), solid bars) is unimodal, with median dwell time of 2.8 msec. The median amplitude of the event plot in FIG. 21A(II) is 20.9 pA with an interquartile range (IQR) of 1.7 pA. Only 6% of events are in the subset range of 13 to 18 pA (FIG. 21A(III), open bars). For the same experiment at constant 150 mV voltage (data not shown), the events cluster around a median amplitude of 14.7 pA and 87% of 150 mV events are in the 13 to 18 pA range. Thus, under extension and aggregation control for which the voltage is reduced to 150 mV for all detected events, a larger percentage of blockades should have a mean amplitude within the 13 to 18 pA range.

Example XXV

Figure 21B:
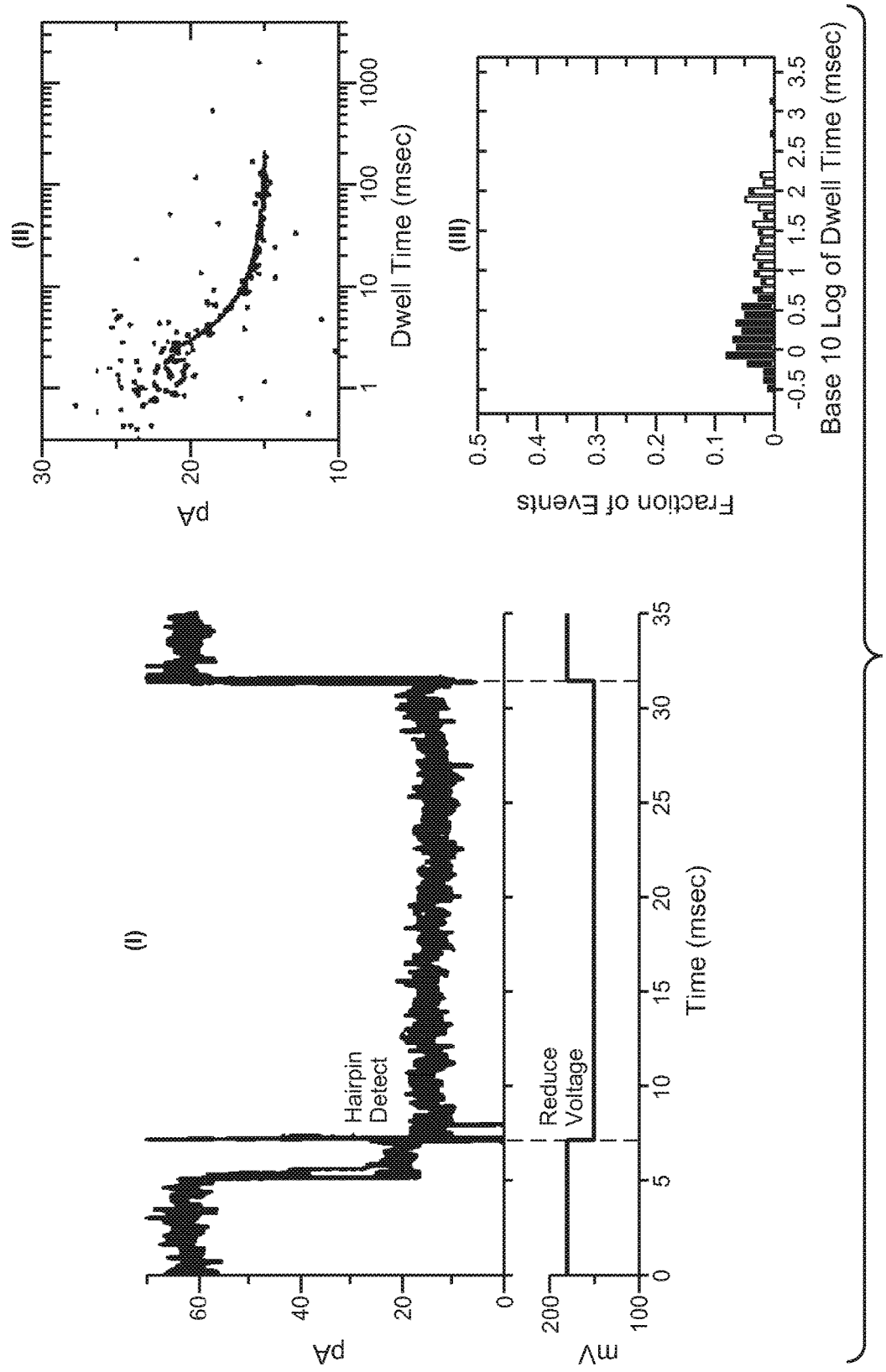

Dwell Time Extension Control (FIG. 21B)

Upon diagnosis of a DNA hairpin event using the mean filtered current, the command voltage is reduced to 150 mV until the hairpin unzips and the DNA translocates through the pore. Using 180 mV for capture results in more events than 150 mV, while reducing to 150 mV extends the life of the hairpin. Again, dwell time extension is useful for sequencing by machine learning methods. The extended time can also be used to increase the likelihood of correctly detecting DNA or DNA-enzyme configurations (states), by increasing the time during which the mean must reside within the amplitude threshold corresponding to each state. After each translocation, the FPGA resets the voltage to 180 mV. A representative event is shown in FIG. 21B(I). The event plot (FIG. 21B(II)) pattern shows that events faster than the nominal diagnosis time of ~1.4 msec are unaffected by extension control, and events with longer dwell times converge to the ~15 pA mean amplitude as expected. The concave trend is also consistent with the mean amplitude computation for each event. In particular, for an event at 21 pA for 1.4 msec and at 15 pA for x msec, an approximate event mean amplitude $\bar{I}$ is $$\bar{I} = \frac{1.4*21 + 15*x}{1.4+x}$$

When x≈24 msec, as in FIG. 21B(I), $\bar{I}$=15 pA. The fraction of events within the subset range 13 to 18 pA increased to 41% and is shown in the open bar histogram overlaid on the probability (filled bars) histogram (FIG. 21B(III)).

Example XXVI

Figure 21C:
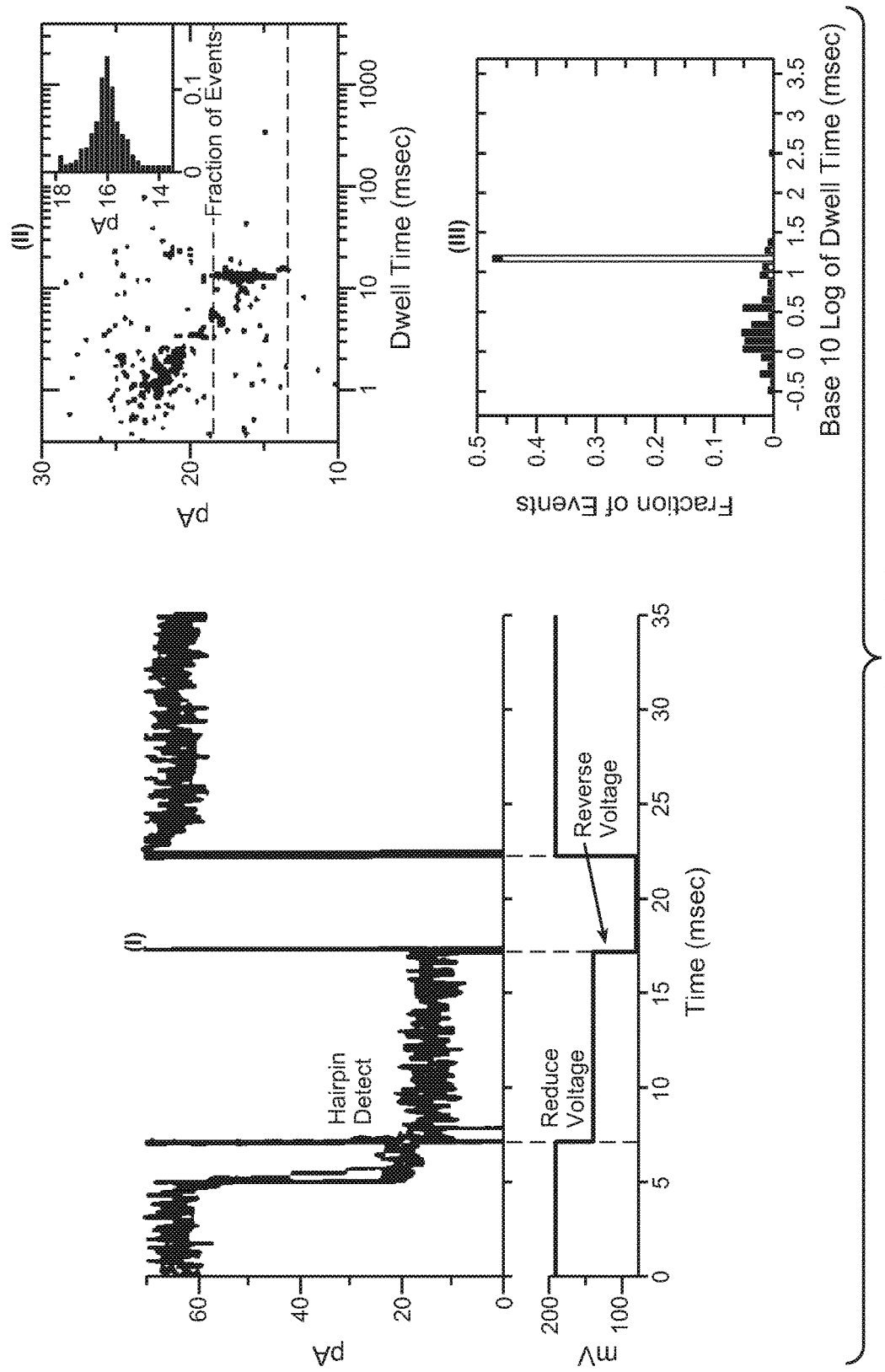

Dwell Time Aggregation Control (FIG. 21C)

The objective was to aggregate the dwell times of the extended events by applying 150 mV for 10 msec upon diagnosis of a hairpin event, followed by voltage reversal of −50 mV for 5 msec. The reversal time of 5 msec is known to sufficiently clear the DNA from the channel, prepping the pore for the next event. The aggregation control would imply a measure of control over the distribution of the events, in addition to control of the individual molecular events. A representative event is shown in FIG. 21C(I). As before, the event plot (FIG. 21C(II)) pattern shows that events faster than the nominal diagnosis time of ~1.4 msec are unaffected by aggregation control. Using the previous equation, for an event at 21 pA for 1.4 msec and at 15 pA for 10 msec, the approximate event mean amplitude is $\bar{I}$=16 pA. Within the subset range of 13 to 18 pA, the median is 16 pA with 0.7 pA IQR, precisely the approximate mean calculation. The fraction of events within the subset range 13 to 18 pA increased to 55%, shown in the open bar histogram overlaid on the filled bar probability histogram (FIG. 21C (III)). For the subset of events, a median dwell time of 12.4 msec is commensurate with a brief delay, required to diagnose hairpin state, plus 10 msec extension time. An IQR of 0.1 for the open bar subset histogram indicates that the aggregation objective has been achieved. Regarding the impact of control on the distribution of events, 43% of all events in FIG. 21C(II) fall within the dwell time range of 12-13 msec and the amplitude range of 13-18 pA.

Example XXVII

Tethered DNA

Preliminary experiments were run with KF bound to a 20 base pair DNA hairpin (20bphp). A single 20 bphp is threaded back and forth through the pore such that KF binds with the DNA multiple times. In this experiment, 1 μM 100mer ssDNA, 5 mM MgCl$_2$, 2 μM KF, and 200 μM of dGTP were present in the cis well of the pore. The ssDNA oligomer was designed such that a 20 mer hairpin forms on the 3' end. On the trans side, there was 2 μM of a 20 base pair (20mer) primer complementary to the sequence at the 5' end of the DNA hairpin in the cis side.

Figure 22A:
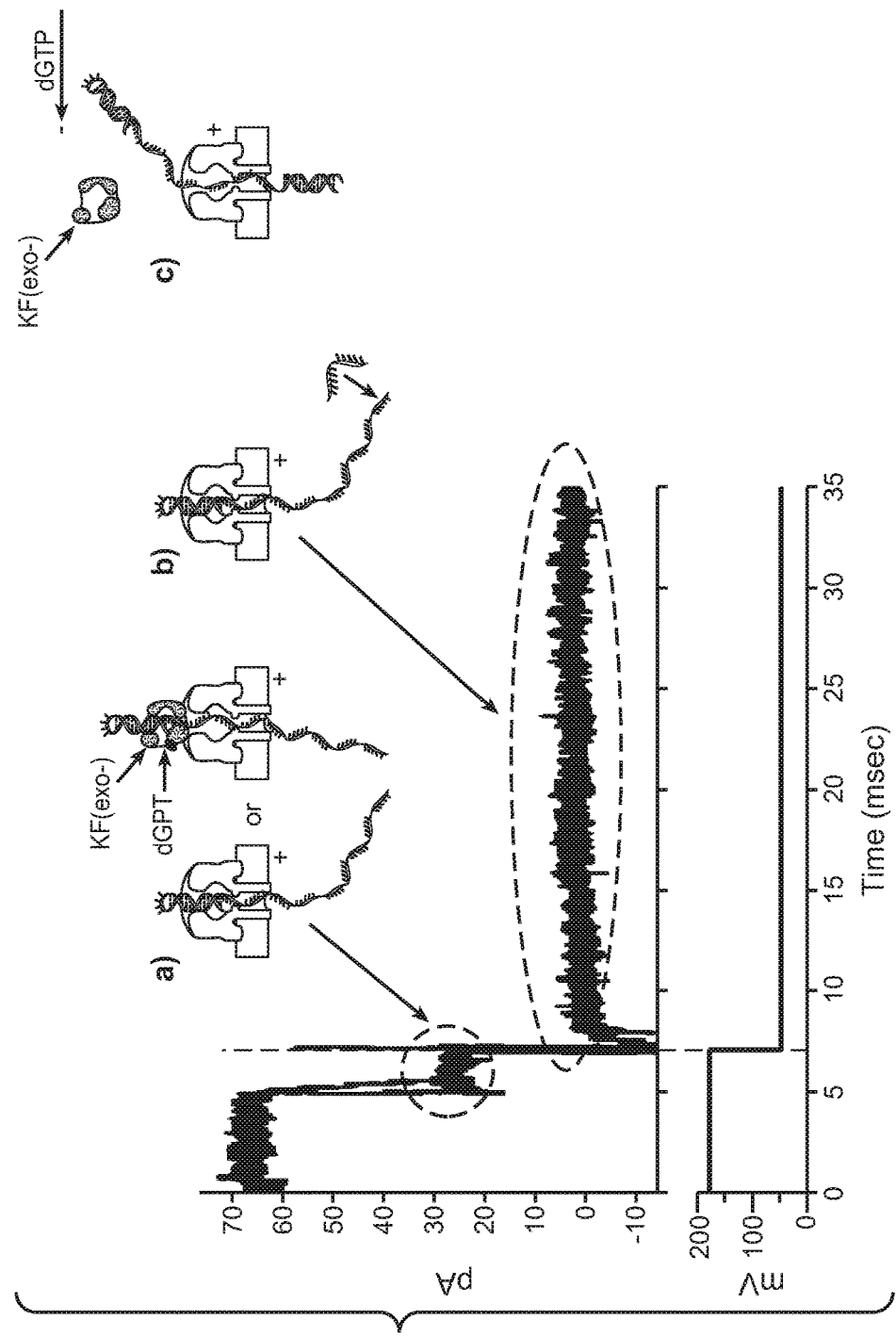
FIG. 22A-22B illustrates repeated KF binding events using a single polynucleotide oligomer.
Figure 22B:
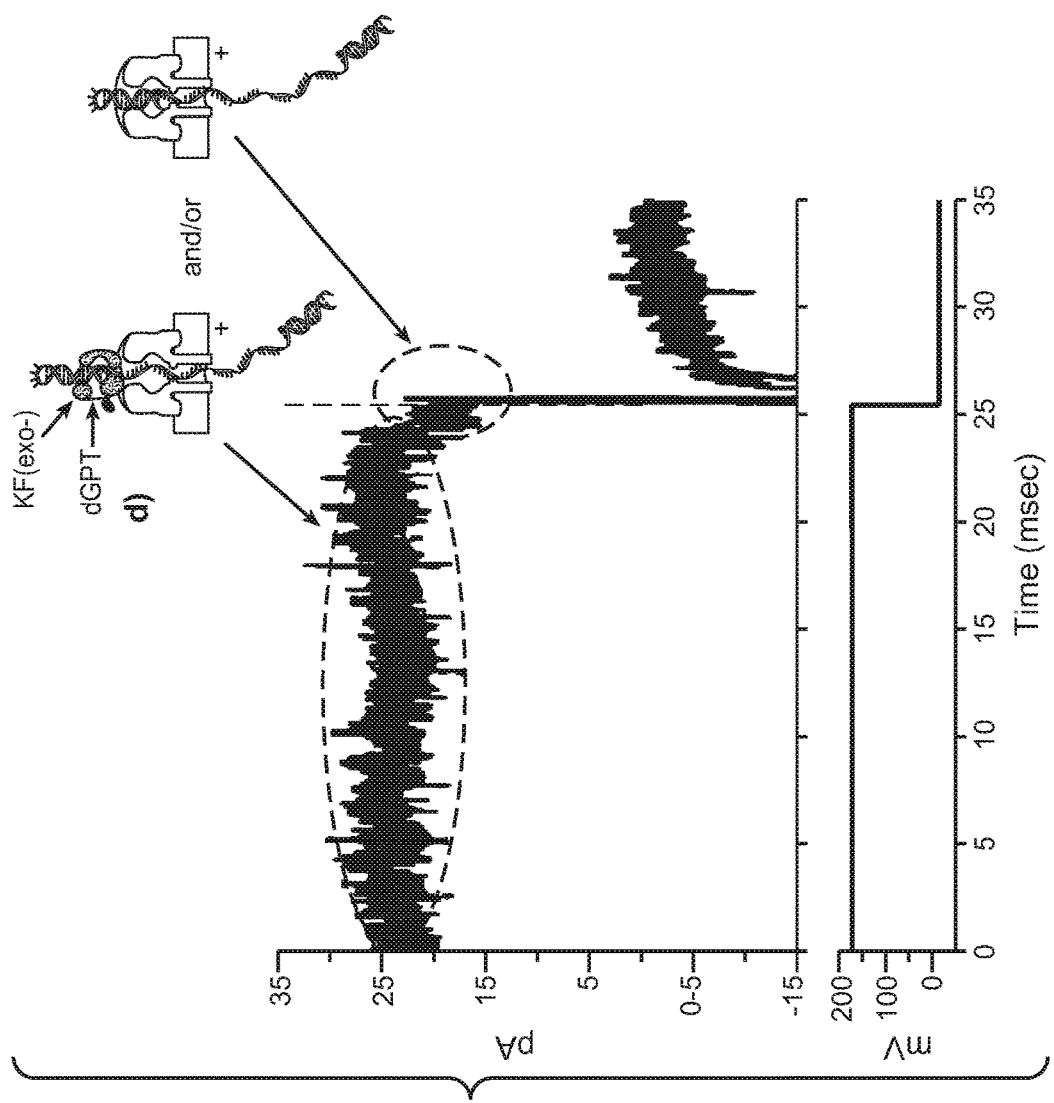

With voltage applied, DNA was drawn through the pore with the 5' end translocating first. When a 20 pA event characteristic of a ssDNA translocation event was detected, the FSM reduced the potential to 50 mV, a level sufficient enough to hold the molecule in the pore but not strong enough to shear the hairpin. If a 24 pA event characteristic of enzyme-bound DNA was detected, application of voltage was continued until the enzyme dissociated, leaving the bare DNA in the pore, at which point the voltage was reduced to 50 mV to hold the molecule in the pore. The molecule was held in the pore for 20 sec, a time found to be sufficient for the 20mer primer to anneal to the 5' end of the DNA at 2 μM primer concentration. With both ends of the DNA consisting of 20 mer double-stranded segments, the molecule was restrained from immediately translocating. After the primer annealing waiting time, the FSM reversed the voltage to −20 mV, pulling the DNA toward the cis side of the pore with enough force to dangle it in solution but not to shear the trans-side primer. The voltage stayed at −20 mV for 5 sec, after which the FSM changed the voltage to 180 mV to diagnose the identity of the molecule in the pore; either DNA alone, DNA/KF binary complex, or DNA/KF/dGTP ternary complex. If enzyme-bound, as presumed if ~24 pA is observed, the FSM monitored the current signal for the 20 pA terminal step, the point when KF has dissociated but before the DNA translocates, to reverse the voltage back to −20 mV to attempt to capture another KF. If the FSM failed to detect the DNA molecule before it translocated, the current returned to the open channel current of ~60 pA, and the FSM would monitor the current for another DNA translocation event and repeat the fishing process (FIG. 22A-22B). If no enzyme is captured during a particular fishing attempt, the FSM tried fishing again until enzyme capture did occur. For the data analyzed from this experiment, five DNA copies were captured and used to fish for KF. Long dwell time events (that is, events >20 msec) were recorded for 95.1% of fishing attempts though no analysis has been done to determine the number of KF dissociation events that were correctly reacted to by the FSM.

After performing the initial proof-of-concept experiments, a second run of fishing experiments were run that yielded better results. Using a fishing time of 0.521 seconds, the FSM captured eight copies of the same DNA hairpin and reacted to 337 potential KF dissociation events over a time period of 380 seconds. Post analysis of the data shows the FPGA correctly detected and reacted to an enzyme dissociation event for 71.86% of KF captures, for example, 74 of the 337 potential dissociation events were false positives.

Example XXVIII

Mitigating False-enzyme Dissociation Detection

In the data presented above, the dissociation of the enzyme is detected by mean filtering the nanopore current signal and checking to see if it is within a chosen amplitude range. This method of smoothing yielded a large number of false detections. As an improvement to this filtering scheme, an exponentially weighted moving average (EWMA) filter can replace the mean filter that the FPGA used. The EWMA filter is a digital implementation of an analog RC filter, commonly used for signal smoothing in electrical engineering applications. The filter calculates a moving average that places exponentially less significance on past samples. EWMA filtering also performs signal smoothing more efficiently than a simple moving average due to its recursive implementation. However, experimental testing still needs to be done to tune the filter for nanopore current signal analysis.

To more robustly detect enzyme dissociation events, a KF dissociation check needs to be implemented to ensure fishing is being done with bare DNA. When the FPGA detects KF dissociation, it will fish for a period of time sufficiently fast so KF will not bind and then it will check the DNA for the presence of enzyme. If only bare DNA is diagnosed (current is ~20 pA), then the enzyme has dissociated and the system can attempt to capture another enzyme. This check is important for performing experiments to collect information on repeat events. For the data to be valid and statistically accurate, each detected event must be a new enzyme binding event.

The majority of long dwell time events correspond to strong KF binding events, for example, the next dNTP to be added to the template strand is present in the nanopore system, when saturating levels of KF and the correct dNTP are present. Multiple long dwell time events in a row improve confidence in base identification because repeated sequential long dwell time events occur even less often when the correct dNTP to be added is absent than when it is present. Here is where KF fishing will show its utility. Separate work is being done to model the dwell time events as a Poisson process so a Phred quality score can be applied to a base identity diagnosis based on the number of repeated sequential long dwell time events. The Phred system is an accuracy metric used commonly in DNA sequencing. For example, a 90% accurate call would be a $Q_{10}$ on the Phred scale and a 99% accurate call would be $Q_{20}$. $Q_{20}$ is considered the standard level of quality in DNA sequencing at the time of writing.

Another method to improve the detectability of the current step at the end of enzyme events is to use a longer hairpin and run the experiments at a higher voltage. The signal-to-noise of the channel current will improve due to higher ion flow through the channel, making the terminal steps more prominent.

Example XXIX

Voltage Titration Experiments

A more quantitative connection between the amplitude and duration of the terminal step and the applied voltage may be made. The goals here are to reveal the repeatability of the terminal step and show how its structure is consistent with DNA alone at different voltages. An in-depth characterization of the terminal step allows for better control of the terminal step. Constant voltage experiments are run at four different voltages with DNA alone as well as DNA/KF/dNTP ternary complex, using saturating levels of each substrate (1 µM, 2 µM, and 200 µM respectively). Voltages are 220, 200, 180, and 160 mV. A 24 bphp is used rather than the 20 bphp used in the other tethered experiments to extend the dwell time at higher voltages. Higher voltages are run first to determine a practical upper limit for an applied voltage that yields detectable terminal step event durations (msec).

Example XXX

Terminal Step Control Experiments

As described above, it is necessary to show accurate detection and reaction to the terminal step. As stated earlier, 97% of enzyme-bound events showed the terminal step, therefore, this is the theoretical maximum detection rate. Detection and reaction to the terminal step will be shown by voltage reversal upon detection, aggregating the terminal step duration. A high probing voltage, as used above, gives more resolution between the bound and unbound current levels. Experiments are run with DNA alone as well as DNA/KF/dNTP ternary complex, using saturating levels of each substrate. Robustness to false positives may be shown by verifying accurate detection offline.

Example XXXI

Terminal Step Control Experiments: Tethered DNA Configuration with Fishing Time Titration A repeat of what was achieved above is performed but with tethered DNA. Titration of the fishing time is performed to reproduce the ratio of DNA alone events to ternary complex events comparable to those in the non-tethered DNA experiments. This information helps set limits on the fishing time to maintain representative sampling of the contents of the cis well. Experiments are run with DNA alone as well as DNA/KF/dNTP ternary complex; using saturating levels of each substrate.

Example XXXII

Fishing Titration Experiments

Titration of KF and dGTP are performed. The percentage of long events are recorded as a function of KF and dGTP concentration. Experiments are run at the same high capture voltage as above. The same concentration intervals for KF and dGTP as in the supplement of Benner et al (2007) Sequence specific detection of DNA polymerase binding using a nanopore-based state machine. Submitted to Nature Methods) are used: (KF=[0, 0.25, 0.5, 1.0, 2.0, 2.0, 2.0, 2.0, 2.0, 2.0, 2.0, 2.0] µM; dGTP=[0, 0, 0, 0, 0, 2.5, 7.5, 15, 30, 60, 120, 200] µM).

Example XXXIII

Other Enzyme Studies

The FPGA/FSM nanopore system can also be used for other enzyme studies. Applying voltage ramps upon capture of DNA/enzyme complexes can produce data to calculate bond energy landscapes using voltage force spectroscopy. Also, DNA's interaction with the pore can be characterized using feedback control of the applied voltage. Regulation of enzyme catalysis can be by achieved applying tension to DNA occupying the pore, counteracting the enzymes processive force.

Example XXXIV

Isolation of Genomic DNA

Blood samples (2-3 ml) are collected from patients via the pulmonary catheter and stored in EDTA-containing tubes at −80° C. until use. Genomic DNA is extracted from the blood samples using a DNA isolation kit according to the manufacturer's instruction (PUREGENE, Gentra Systems, Minneapolis Minn.). DNA purity is measured as the ratio of the absorbance at 260 and 280 nm (1 cm lightpath; $A_{260}/A_{280}$) measured with a Beckman spectrophotometer.

Example XXXV

Identification of SNPs

A region of a gene from a patient's DNA sample is amplified by PCR using the primers specifically designed for the region. The PCR products are sequenced using methods as disclosed above. SNPs identified in the sequence traces are verified using Phred/Phrap/Consed software and compared with known SNPs deposited in the NCBI SNP databank.

Example XXXVI cDNA Library Construction

A cDNA library is constructed using RNA isolated from mammalian tissue. The frozen tissue is homogenized and lysed using a POLYTRON homogenizer (Brinkmann Instruments, Westbury N.J.) in guanidinium isothiocyanate solution. The lysates are centrifuged over a 5.7 M CsCl cushion using a SW28 rotor in an L8-70M Ultracentrifuge (Beckman Coulter, Fullerton Calif.) for 18 hours at 25,000 rpm at ambient temperature. The RNA is extracted with acid phenol, pH 4.7, precipitated using 0.3 M sodium acetate and 2.5 volumes of ethanol, resuspended in RNAse-free water, and treated with DNAse at 37° C. RNA extraction and precipitation are repeated as before. The mRNA is isolated with the OLIGOTEX kit (Qiagen, Chatsworth Calif.) and used to construct the cDNA library.

The mRNA is handled according to the recommended protocols in the SUPERSCRIPT plasmid system (Invitrogen). The cDNAs are fractionated on a SEPHAROSE CL4B column (APB), and those cDNAs exceeding 400 bp are ligated into an expression plasmid. The plasmid is subsequently transformed into DH5 □a competent cells (Invitrogen).

Example XXXVII

Preparation and Sequencing of cDNAs

The cDNAs are prepared using a MICROLAB 2200 (Hamilton, Reno Nev.) in combination with DNA ENGINE thermal cyclers (MJ Research) and sequenced by the method of Sanger and Coulson (1975; J. Mol. Biol. 94: 441-448) using PRISM 377 or 373 DNA sequencing systems (ABI). Reading frame is determined using standard techniques.

The nucleotide sequences and/or amino acid sequences of the Sequence Listing are used to query sequences in the GenBank, SwissProt, BLOCKS, and Pima II databases. BLAST produced alignments of both nucleotide and amino acid sequences to determine sequence similarity. Because of the local nature of the alignments, BLAST is used in determining exact matches or in identifying homologs that may be of prokaryotic (bacterial) or eukaryotic (animal, fungal, or plant) origin. Other algorithms such as those of Smith et al. (1992; Protein Engineering 5:35-51) could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold is set at $10^{-25}$ for nucleotides and $10^{-10}$ for peptides.

Example XXXVIII

Extension of cDNAs

The cDNAs are extended using the cDNA clone and oligonucleotide primers. One primer is synthesized to initiate 5' extension of the known fragment, and the other, to initiate 3' extension of the known fragment. The initial primers are designed using primer analysis software to be about 22 to 30 nucleotides in length, to have a GC content of about 50% or more, and to anneal to the target sequence at temperatures of about 68° C. to about 72° C. Any stretch of nucleotides that would result in hairpin structures and primer-primer dimerizations is avoided.

Selected cDNA libraries are used as templates to extend the sequence. If extension is performed than one time, additional or nested sets of primers are designed. Preferred libraries have been size-selected to include larger cDNAs and random primed to contain more sequences with 5' or upstream regions of genes. Genomic libraries can be used to obtain regulatory elements extending into the 5' promoter binding region.

High fidelity amplification is obtained by PCR using methods such as that taught in U.S. Pat. No. 5,932,451. PCR is performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Invitrogen), and Pfu DNA polymerase (Stratagene), with the following parameters. The parameters for the cycles are 1: 94° C., three minutes; 2: 94° C., 15 seconds; 3: 60° C., one minute; 4: 68° C., two minutes; 5: 2, 3, and 4 repeated 20 times; 6: 68° C., five minutes; and 7: storage at 4° C. In the alternative, the parameters for primer pair T7 and SK+ (Stratagene) are as follows: 1: 94° C., three minutes; 2: 94° C., 15 seconds; 3: 57 C, one minute; 4: 68° C., two minutes; 5: 2, 3, and 4 repeated 20 times; 6: 68° C., five minutes; and 7: storage at 4° C.

The concentration of DNA in each well is determined by dispensing 100 ml PICOGREEN quantitation reagent (0.25% reagent in 1×TE, v/v; Molecular Probes) and 0.5 ml of undiluted PCR product into each well of an opaque fluorimeter plate (Corning Life Sciences, Acton Mass.) and allowing the DNA to bind to the reagent. The plate is scanned in a Fluoroskan II (Labsystems Oy, Helsinki, Finland) to measure the fluorescence of the sample and to quantify the concentration of DNA. A 5 ml to 10 ml aliquot of the reaction mixture is analyzed by electrophoresis on a 1% agarose minigel to determine which reactions are successful in extending the sequence.

The extended clones are desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences are separated on low concentration (0.6 to 0.8%) agarose gels, fragments are excised, and the agar is digested with AGARACE enzyme (Promega). Extended clones are religated using T4 DNA ligase (New England Biolabs) into pUC18 vector (APB), treated with Pfu DNA polymerase (Stratagene) to fill-in restriction site overhangs, and transfected into *E. coli* competent cells. Transformed cells are selected on antibiotic-containing media, and individual colonies are picked and cultured overnight at 37° C. in 384-well plates in LB/2× carbenicillin liquid media.

The cells are lysed, and DNA is amplified using primers, Taq DNA polymerase (APB) and Pfu DNA polymerase (Stratagene) with the following parameters: 1: 94° C., three minutes; 2: 94° C., 15 seconds; 3: 60° C., one minute; 4: 72° C., two minutes; 5: 2, 3, and 4 repeated 29 times; 6: 72° C., five minutes; and 7: storage at 4° C. DNA is quantified using PICOGREEN quantitation reagent (Molecular Probes) as described above. Samples with low DNA recoveries are reamplified using the conditions described above. Samples are diluted with 20% dimethylsulfoxide (DMSO; 1:2, v/v), and sequenced using DYENAMIC energy transfer sequencing primers and the DYENAMIC DIRECT cycle sequencing kit (APB) or the PRISM BIGDYE terminator cycle sequencing kit (ABI).

Example XXXIX

Extension of Polynucleotides

At least one of the polynucleotides used to assemble a polynucleotide is produced by extension of a cDNA clone using oligonucleotide primers. One primer is synthesized to initiate 5' extension of the known fragment, and the other, to initiate 3' extension. The initial primers are designed using OLIGO 4.06 primer analysis software (National Biosciences) to be about 22 to 30 nucleotides in length, to have a GC content of about 50%, and to anneal to the target sequence at temperatures of about 55° C. to about 68° C. Any fragment that would result in hairpin structures and primer-primer dimerizations is avoided. Selected human cDNA libraries are used to extend the molecule. If more than one extension is needed, additional or nested sets of primers are designed.

High fidelity amplification is obtained by performing PCR in 96-well plates using the DNA ENGINE thermal cycler (MJ Research). The reaction mix contains DNA template, 200 nmol of each primer, reaction buffer containing $Mg^{2+}$, $(NH_4)_2$ $SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair selected from the plasmid: Step 1: 94° C., 3 minutes; Step 2: 94° C., 15 seconds; Step 3: 60° C., 1 minute; Step 4: 68° C., 2 minutes; Step 5: Steps 2, 3 and 4 repeated 20 times; Step 6: 68° C., 5 minutes; Step 7: storage at 4° C. In the alternative, when using a sequence inserted into a plasmid vector, parameters for the primer pair, T7 and SK+(Stratagene), are as follows: Step 1: 94° C., 3 minutes; Step 2: 94° C., 15 seconds; Step 3: 57° C., 1 minutes; Step 4: 68° C., 2 minutes; Step 5: Steps 2, 3, and 4 repeated 20 times; Step 6: 68° C., 5 minutes; Step 7 storage at 4° C.

The concentration of DNA in each well is determined by dispensing 100 ml PICOGREEN quantitation reagent (0.25% (v/v); Molecular Probes) dissolved in 1xTE and 0.5 ml of undiluted PCR product into each well of an opaque fluorimeter plate (Corning Costar, Acton Mass.) and allowing the DNA to bind to the reagent. The plate is scanned in a Fluoroskan II (Labsystems Oy, Helsinki, Finland) to measure the fluorescence of the sample and to quantify the concentration of DNA. A 5 ml to 10 ml aliquot of the reaction mixture is analyzed by electrophoresis on a 1% agarose mini-gel to determine which reactions are successful in producing longer sequence.

The extended sequences are desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested fragments are separated on about 0.6-0.8% agarose gels, fragments are excised as visualized under UV light, and agar removed/digested with AGARACE (Promega). Extended fragments are religated using T4 DNA ligase (New England Biolabs) into pUC 18 vector (Amersham Pharmacia Biotech), treated with Pfu DNA polymerase (Stratagene) to fill-in restriction site overhangs, and transformed into competent E. coli cells. Transformed cells are selected on antibiotic-containing media, and individual colonies are picked and cultured overnight at 37° C. in 384-well plates in LB/2xcarbenicillin liquid media.

The cells are lysed, and DNA is amplified using Taq DNA polymerase (Amersham Pharmacia Biotech) and Pfu DNA polymerase (Stratagene) with the following parameters: Step 1: 94° C., 3 minutes; Step 2: 94° C., 15 seconds; Step 3: 60° C., 1 minutes; Step 4: 72° C., 2 minutes; Step 5: steps 2, 3, and 4 repeated 29 times; Step 6: 72° C., 5 minutes; Step 7: storage at 4° C. DNA is quantified by PICOGREEN reagent (Molecular Probes) as described above. Samples with low DNA recoveries are reamplified using the conditions described above. Samples are diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE terminator cycle sequencing ready reaction kit (PE Biosystems).

In like manner, the polynucleotides of other sequences are used to obtain regulatory sequences using the procedure above, oligonucleotides designed for outward extension, and a genomic DNA library.

Example XL

Labeling of Probes and Hybridization Analyses

Nucleic acids are isolated from a biological source and applied to a substrate for standard hybridization protocols by one of the following methods. A mixture of target nucleic acids, a restriction digest of genomic DNA, is fractionated by electrophoresis through an 0.7% agarose gel in 1xTAE [Tris-acetate-ethylenediamine tetraacetic acid (EDTA)] running buffer and transferred to a nylon membrane by capillary transfer using 20xsaline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEP-HACRYL-400 beads (Amersham Pharmacia Biotech). Purified target nucleic acids are robotically arrayed onto a glass microscope slide (Corning Science Products, Corning N.Y.). The slide is previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

cDNA probes are made from mRNA templates. Five micrograms of mRNA is mixed with 1 mg random primer (Life Technologies), incubated at 70° C. for 10 minutes, and lyophilized. The lyophilized sample is resuspended in 50 ml of 1xfirst strand buffer (cDNA Synthesis systems; Life Technologies) containing a dNTP mix, [a-$^{32}$ P]dCTP, dithiothreitol, and MMLV reverse transcriptase (Stratagene), and incubated at 42° C. for 1-2 hours. After incubation, the probe is diluted with 42 ml dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 MicroColumn (Amersham Pharmacia Biotech). Probes can be labeled with fluorescent markers, Cy3-dCTP or Cy5-dCTP (Amersham Pharmacia Biotech), in place of the radionucleotide, [$^{32}$P] dCTP.

Hybridization is carried out at 65° C. in a hybridization buffer containing 0.5 M sodium phosphate (pH 7.2), 7% SDS, and 1 mM EDTA. After the substrate is incubated in hybridization buffer at 65° C. for at least 2 hours, the buffer is replaced with 10 ml of fresh buffer containing the probes. After incubation at 65° C. for 18 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the substrate is examined by confocal laser microscopy, and images are collected and analyzed using gene expression analysis software.

Example XLI

Complementary Polynucleotides

Molecules complementary to the polynucleotide, or a fragment thereof, are used to detect, decrease, or inhibit gene expression. Although use of oligonucleotides comprising from about 15 to about 30 base pairs is described, the same procedure is used with larger or smaller fragments or their derivatives (for example, peptide nucleic acids, PNAs). Oligonucleotides are designed using OLIGO 4.06 primer analysis software (National Biosciences). To inhibit transcription by preventing a transcription factor binding to a promoter, a complementary oligonucleotide is designed to bind to the most unique 5' sequence, most preferably between about 500 to 10 nucleotides before the initiation codon of the open reading frame. To inhibit translation, a complementary oligonucleotide is designed to prevent ribosomal binding to the mRNA encoding the mammalian protein.

Example XLII

Production of Specific Antibodies

A conjugate comprising a complex of polynucleotide and a binding protein thereof is purified using polyacrylamide gel electrophoresis and used to immunize mice or rabbits. Antibodies are produced using the protocols below. Rabbits are immunized with the complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

Example XLIII

Screening Molecules for Specific Binding with the Polynucleotide or Protein Conjugate The polynucleotide, or fragments thereof, are labeled with $^{32}$P-dCTP, Cy3-dCTP, or Cy5-dCTP (Amersham Pharmacia Biotech), or with BIODIPY or FITC (Molecular Probes, Eugene Oreg.), respectively. Similarly, the conjugate comprising a complex of polynucleotide and a binding protein thereof can be labeled with radionucleide or fluorescent probes. Libraries of candidate molecules or compounds previously arranged on a substrate are incubated in the presence of labeled polynucleotide or protein. After incubation under conditions for either a polynucleotide or amino acid molecule, the substrate is washed, and any position on the substrate retaining label, which indicates specific binding or complex formation, is assayed, and the ligand is identified. Data obtained using different concentrations of the polynucleotide or protein are used to calculate affinity between the labeled polynucleotide or protein and the bound molecule.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method for analyzing a plurality of molecules, comprising:
    (a) forming a plurality of individually addressable nanopore devices on a chip, each individually addressable nanopore device of said plurality of individually addressable nanopore devices containing at least one nanopore formed in a membrane disposed adjacent to an electrode, each individually addressable nanopore device being addressable using row and column addressing;
    (b) directing a plurality of molecules to said individually addressable nanopore devices; and
    (c) analyzing, with the aid of a processor coupled to said chip, at least a portion of each of said molecules based on electrical signals received from said plurality of individually addressable nanopore devices.

2. The method of claim 1, each individually addressable nanopore device of said plurality of individually addressable nanopore devices including an electrical circuit including a plurality of components, wherein said plurality of components are controllable by using said row and column addressing.

3. The method of claim 1, wherein said plurality of molecules comprises a plurality of nucleic acid molecules.

4. The method of claim 1, wherein said electrode is adapted to supply an electrical stimulus across said membrane, wherein said electrical stimulus enables generation of said electrical signals upon molecular flow of said molecules or portion thereof.

5. The method of claim 1, wherein each individually addressable nanopore device is adapted to regulate molecular flow with the aid of an electrical stimulus applied to said individually addressable nanopore device.

6. A system for analyzing a plurality of molecules, comprising:
(a) a chip comprising a plurality of individually addressable nanopore devices, each individually addressable nanopore device of said plurality of individually addressable nanopore devices containing at least one nanopore formed in a membrane disposed adjacent to an electrode, each individually addressable nanopore device being addressable using row and column addressing; and
(b) a processor coupled to said chip, wherein said processor is programmed to aid in
analyzing at least a portion of each of said molecules based on electrical signals received from said plurality of individually addressable nanopore devices.

7. The system of claim 6, each individually addressable nanopore device of said plurality of individually addressable nanopore devices including an electrical circuit including a plurality of components, wherein said plurality of components are controllable by using said row and column addressing.

8. The system of claim 6, wherein said plurality of molecules comprises a plurality of nucleic acid molecules.

9. The system of claim 6, wherein said electrode is adapted to supply an electrical stimulus across said membrane, wherein said electrical stimulus enables generation of said electrical signals upon molecular flow of said molecules or portion thereof.

10. The system of claim 6, wherein each individually addressable nanopore device is adapted to regulate molecular flow with the aid of an electrical stimulus applied to said individually addressable nanopore device.

* * * * *